(12) United States Patent
Saimoto et al.

(10) Patent No.: US 9,440,913 B2
(45) Date of Patent: Sep. 13, 2016

(54) DIHYDROXYBENZENE DERIVATIVES AND ANTIPROTOZOAL AGENT COMPRISING SAME AS ACTIVE INGREDIENT

(75) Inventors: Hiroyuki Saimoto, Tottori (JP); Kiyoshi Kita, Tokyo (JP); Yoshisada Yabu, Aichi (JP); Masaichi Yamamoto, Tokyo (JP)

(73) Assignee: NAI INC., Minato-Ku, Tokyo (JP)

(*) Notice: Subject to any disclaimer, the term of this patent is extended or adjusted under 35 U.S.C. 154(b) by 564 days.

(21) Appl. No.: 13/882,647

(22) PCT Filed: Nov. 1, 2011

(86) PCT No.: PCT/JP2011/075216
§ 371 (c)(1),
(2), (4) Date: Jul. 15, 2013

(87) PCT Pub. No.: WO2012/060387
PCT Pub. Date: May 10, 2012

(65) Prior Publication Data
US 2013/0296422 A1    Nov. 7, 2013

(30) Foreign Application Priority Data
Nov. 1, 2010  (JP) .............................. 2010-258343

(51) Int. Cl.
| | | |
|---|---|---|
| *C07C 255/53* | (2006.01) |
| *C07C 47/27* | (2006.01) |
| *C07C 49/248* | (2006.01) |
| *C07C 59/90* | (2006.01) |
| *A61K 31/11* | (2006.01) |
| *A61K 31/12* | (2006.01) |
| *A61K 31/192* | (2006.01) |
| *A61K 31/216* | (2006.01) |
| *A61K 31/336* | (2006.01) |
| *A61K 31/351* | (2006.01) |
| *A61K 31/357* | (2006.01) |
| *A61P 33/00* | (2006.01) |
| *C07C 47/56* | (2006.01) |
| *C07C 59/74* | (2006.01) |
| *C07C 69/738* | (2006.01) |
| *A61K 45/06* | (2006.01) |
| *A61K 31/047* | (2006.01) |
| *C07C 47/575* | (2006.01) |
| *C07C 49/258* | (2006.01) |
| *C07C 49/835* | (2006.01) |
| *C07C 49/84* | (2006.01) |

(52) U.S. Cl.
CPC ........... *C07C 255/53* (2013.01); *A61K 31/047* (2013.01); *A61K 45/06* (2013.01); *C07C 47/27* (2013.01); *C07C 47/56* (2013.01); *C07C 47/575* (2013.01); *C07C 49/248* (2013.01); *C07C 49/258* (2013.01); *C07C 49/835* (2013.01); *C07C 49/84* (2013.01); *C07C 59/74* (2013.01); *C07C 59/90* (2013.01); *C07C 69/738* (2013.01)

(58) Field of Classification Search
CPC ..... C07C 69/738; C07C 47/56; C07C 47/27; C07C 47/575; C07C 49/84; C07C 49/258; C07C 49/835; C07C 59/74; C07C 59/90; C07C 255/53; A61K 45/06; A61K 31/47
USPC ................ 514/522, 545, 570, 678; 558/416; 560/53; 562/436; 568/308, 442
See application file for complete search history.

(56) References Cited

U.S. PATENT DOCUMENTS

| 3,546,073 A | 12/1970 | Evans et al. |
| 7,622,598 B2* | 11/2009 | Saimoto ................. C07C 47/56 549/475 |
| 2007/0208078 A1 | 9/2007 | Saimoto et al. |

FOREIGN PATENT DOCUMENTS

| EP | 1681280 A1 | 7/2006 |
| JP | 07278041 A | 10/1995 |

(Continued)

OTHER PUBLICATIONS

Blicke et al. "The Use of Substituted Phenols in the Mannich Reaction and the Dehalogenation of Aminomethylhalophenols" J. Org. Chem. 1959, 24, 1061-1069.*

(Continued)

*Primary Examiner* — Nyeemah A Grazier
*Assistant Examiner* — Amanda L Aguirre
(74) *Attorney, Agent, or Firm* — MacMillan, Sobanski & Todd, LLC

(57) ABSTRACT

Novel compounds below are useful for preventing or treating diseases caused by protozoans. At least one of a compound represented by Formula (I)

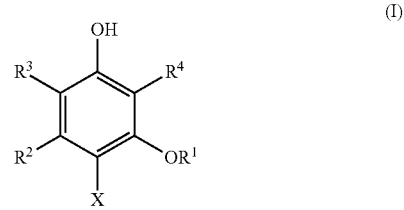

(wherein, X represents a hydrogen atom or a halogen atom; $R^1$ represents a hydrogen atom; $R^2$ represents a hydrogen atom or a $C_{1-7}$ alkyl group; $R^3$ represents —CHO, —C(=O)$R^5$, —COO$R^5$ (wherein $R^5$ represents a $C_{1-7}$ alkyl group), —CH$_2$OH or —COOH; and $R^4$ represents a $C_{1-16}$ alkyl group having one or more substituents on a terminal carbon atom and/or non-terminal carbon atom(s), a $C_{2-16}$ alkenyl group having one or more substituents on a terminal carbon atom and/or non-terminal carbon atom(s), or a $C_{2-16}$ alkynyl group having one or more substituents on a terminal carbon atom and/or non-terminal carbon atom(s)), an optical isomer thereof, and a pharmaceutically acceptable salt is used.

9 Claims, No Drawings

(56) References Cited

FOREIGN PATENT DOCUMENTS

| | | | |
|---|---|---|---|
| JP | 09165332 A | 6/1997 | |
| JP | 2004231601 A | 8/2004 | |
| JP | 2005112755 A | 4/2005 | |
| JP | 2005330265 A | 12/2005 | |
| JP | 2007204380 A | 8/2007 | |
| WO | 2005037759 A1 | 4/2005 | |
| WO | 2005037760 A1 | 4/2005 | |

OTHER PUBLICATIONS

Singh et al. "Chemistry and Biology of Cylindrols: Novel Inhibitors of Ras Farnesyl-Protein Transferasc from Cylindrocarpon lucidum" J. Org. Chem. 1996, 61(22), 7727-7737.*

Moores et al. "Sequence Dependence of Protein Isoprenylation" J. Biol. Chem. 1991, 266(22) 14603-14610.*

Mills, S. "Pharmaceutical excipients—an overview including considerations for paediatric dosing."Jun. 21-25, 2010 [online]: World Health Organization [retrieved on Aug. 31, 2015]. Retrieved from <http://apps.who.int/prequal/trainingresources/pq_pres/workshop_China2010/english/22/002-Excipients.pdf>.*

Furstner et al., "Total Synthesis of Cristatic Acid", Organic Letters, 2000, vol. 2, No. 16, pp. 2467-2470.

Hosono et al., "LL-Z1272α epoxide, a precursor of ascochlorin produced by a mutant of Ascochyta viciae", The Journal of Antibiotics, 2009, vol. 62, pp. 571-574.

Fournet et al., In vitro and in vivo leishmanicidal studies of Peperomia galioides (Piperaceae), Phytomedicine, 1996, vol. 3, No. 3, pp. 271-275.

Kosuge et al., Structures of Colletochlorin C, Colletorin a and Colletorin C from Colletotrichum nicotianae, Agricultural and Biological Chemistry, 1974, vol. 38, No. 6, p. 1265-1267.

Minagawa et al., An antibiotic, ascofuranone, specifically inhibits respiration and in vitro growth of long slender bloodstream forms of Trypanosoma brucei brucei, Molecular and Biochemical Parasitology, 1996, vol. 81, p. 127-136.

Singh et al., Chemistry and Biology of Cylindrois: Novel Inhibitors of Ras Farnesyl-Protein Transferase from Cylindrocarpon lucidum, Journal of Organic Chemistry, 1996, vol. 61, No. 22, p. 7727-7737.

Yabu et al., Oral and intraperitoneal treatment of Trypanosoma brucei brucei with a combination of ascofuranone and glycerol mice, Parasitology International, 1998, vol. 47, p. 131-137.

Zhang et al., Anti-inflammatory Sesquiterpenoids from a Sponge-Derived Fungus *Acremonium* sp., Journal of Natural Products, 2009, vol. 72, No. 2, p. 270-275.

* cited by examiner

DIHYDROXYBENZENE DERIVATIVES AND ANTIPROTOZOAL AGENT COMPRISING SAME AS ACTIVE INGREDIENT

TECHNICAL FIELD

This invention relates to novel halogen-containing dihydroxybenzene derivatives having an alkyl side chain, pharmaceutical compositions containing the same as active ingredients for the prevention or treatment of diseases caused by protozoans, such as *Trypanosoma* and *Cryptosporidium*, and use of these active ingredients in the manufacture of pharmaceutical compositions for the prevention or treatment of diseases caused by protozoans.

BACKGROUND ART

Trypanosomiasis is caused by Trypanosomatidae and 200,000 to 300,000 cases of trypanosomiasis are said to occur annually. The number of patients with African sleeping sickness cannot be determined due to low reliability of surveillance data at present. According to the WHO, at least 150,000 people died of the sickness in 1996 and 100,000 people or more have its aftereffects. Moreover, a disease called as nagana does more serious damage to domestic animals, with several hundred thousands of cattle which are to be protein sources for people lost annually to the disease. Furthermore, *Trypanosoma* has made it impossible to do livestock farming in savanna with an area of about 10,000,000 km² equal to that of the United States of America. As mentioned above, African sleeping sickness greatly has hampered health and economic development of African people. This is the reason why the WHO has described the sickness as one of infectious diseases to be controlled.

African sleeping sickness is a tsetse-fly-transmitted protozoal infection caused by *Trypanosoma* and the protozoan appears in the bloodstream in about 10 days after infection. At the initial phase of infection, the protozoan multiplies in the bloodstream and cause fever, malaise, headaches, aching muscles and joints, and itching to occur and progress. During the chromic phase of infection, the central nerve is affected to show symptoms such as mental confusion and generalized convulsion, and finally the infection causes lethargy, eventually leading to death.

Trypanosomiasis in domestic animals is an epidemic which is caused by the pathogens *Trypanosoma brucei brucei, T. evansi, T. congolense*, and *T. vivax* and affects domestic animals such as horses, cattle, pigs and dogs as well as mice, guinea pigs, and rabbits. Particularly cattle and horses are worst affected by the epidemic, which is almost fatal to cattle and horses, causing symptoms such as anemia, edema, and weakness and, in one month after infection, death.

Some pharmaceuticals such as pentamidine, melarsoprol, and eflornithine are used for treating trypanosomiasis and there was sentiment in the 1960s that it might possibly be eradicated. These pharmaceuticals are, however, old and have decreasing efficacy. Particularly, tolerance to melarsoprol as an arsenic-containing agent is a serious issue, and patients showing no effect of the agent are therefore in such a dire situation that those patients can do nothing but wait to die.

*Trypanosoma* primarily lives in the bloodstream of the human body. This energy metabolism in the blood stream form depends on the glycolytic pathway localized in the organelle, known as glycosome, characteristic of the protozoan while the so-called oxidative phosphorylation in mitochondria does not work. To efficiently drive this glycolytic pathway, the NADH generated has to be reoxidized. In this reoxidation, the glycerol-3-phosphate oxidation pathway in mitochondria plays an important role. The terminal oxidizing enzyme in this oxidation pathway functions as a quinol oxidase having a reduced ubiquinone as an electron donor, and has properties significantly different from those of cytochrome oxidase in an aerobic respiratory system present in the host. It is particularly noted that the terminal oxidase of the oxidation system is non-sensitive to the cyanide which rapidly inhibits the cytochrome oxidase in the host. Many researchers around Western countries have thus attempted to develop pharmaceuticals targeting this cyanide-insensitive oxidase only to fail to create effective ones having a highly selective toxicity.

Under these circumstances, the present inventors have discovered that isoprenoid based physiologically active substances, ascochlorin, ascofuranone and derivatives thereof, particularly ascofuranone specifically inhibits the glycerol-3-phosphate oxidation pathway in *Trypanosoma* at an extremely low concentration of the order of nM and filed a patent application (Japanese Patent Application Laid-Open Publication No. H09-165332). That is, the inhibitory effect of ascochlorin, ascofuranone, and derivatives thereof on the glycerol-3-phosphate-dependent respiration was examined in the mitochondrial specimen prepared by mechanically homogenizing the bodies of *T. brucei brucei* multiplied in the rat bloodstream with glass beads followed by differential centrifugation. Antimycin A3, myxothiazol, and stigmatellin, all of which are known as Q-cycle inhibitors, had absolute amounts of 50% inhibition of 48,600, 21,500, and 18,600 pmol/mg protein respectively, whereas ascofuranone showed the inhibitory effect at a concentration as extremely low as 25 pmol/mg protein.

With the aim of making ascofuranone in practical use, it was found that there was a need to discover a pharmaceutical which replace glycerol and exhibit an effect of the combined use in a small amount, and that use of an alkaloid compound having an indole skeleton belonging to the plant family Simaroubaceae with ascofuranone provided life-lengthening or curing effect in African sleeping sickness, and then a patent application was filed (Japanese Patent Application No. 2003-24643 (Japanese Patent Application Laid-Open Publication No. 2004-231601)). Moreover, the present applicant devised a novel phenol derivative that can be used as an antitrypanosoma preventing/treating agent (WO2005/037760).

Meanwhile, *Cryptosporidium parvum*, which causes cryptosporidiosis, is the 5 μm smallest, oval-shaped intestinal protozoan. This intestinal protozoan belongs to Sporozoa Coccidia, parasitizes inside the microvilli of the mucosal epithelial cells, and multiplies while repeating in turns asexual reproduction and sexual reproduction. Many of the oocysts formed in sexual reproduction are excreted in the faeces, which become sources of infection to other individuals. The pathological condition of cryptosporidiosis is as follows: the main symptom is severe watery diarrhea associated with abdominal pain from 4-5 days to about a week, and about half of the cases have vomiting and mild fever, and most cases have no rectal bleeding. For cryptosporidiosis patients with normal immune function, the diarrhea subsides in a week or two even without any treatment, while for immunodeficient cryptosporidiosis patients, who has poor antibody formation, the diarrhea is intractable, can become chronic and more severe as there is no effective therapy for such diarrhea.

It is said that the detection rate of *Cryptosporidium* oocysts from diarrheal stool is about 10% in Africa and Central and South America, 5% in the Asia-Pacific regional, 3.5% in Europe, and 1.6% in North America, and that hundreds of millions of people worldwide are infected with *Cryptosporidium* annually.

*Cryptosporidium* is a zoonotic pathogen that infects small intestinal epithelial cells and causes severe diarrhea. This is of interest as a pathogen causing emerging infectious diseases that cause mass water-borne infection, as well as pathogen causing endemic tropical diseases, or opportunistic pathogen in immunodeficient patients.

*Cryptosporidium*, which is a minute protozoan discovered in 1907, has not attracted medical attention due to its unclear pathogenicity. In 1976, this protozoan was reported to cause diarrhea to human, and in 1982 *C. parvum* was detected by the U.S. Centers for Disease Control and Prevention (CDC) from many AIDS patients complaining of severe diarrhea and abdominal pain. Since then, *Cryptosporidium* has attracted much attention.

If AIDS patients are infected with *C. parvum*, then repeated multiplication of *C. parvum* takes place in the intestinal mucosa of the host over one year and the outcome is debilitation and eventually death in many cases even though symptomatic therapy is given. If healthy individuals are infected by *C. parvum*, cryptosporidiosis is characterized by watery stool to mucous stool and loose stool with abdominal pain as its chief symptom although it lingers and becomes severe in some cases in infants and the elderly.

*Cryptosporidium* is widely prevalent among animals, for example, domestic animals such as cattle, pigs, and sheep as well as dogs, cats, and mice. Particularly, for calves, individuals less than one month old are likely to be infected by *Cryptosporidium* to develop cryptosporidiosis. The symptoms such as watery diarrhea along with abdominal pain, and fever persist for three days to about a week. Additionally, the symptoms are exacerbated by mixed infection with viruses, bacteria, and Coccidia.

Reports on cryptosporidiosis in animals have been made from researchers from different countries in the world and cattle worldwide were found to be contaminated by the present infection. Also, in North America, detailed data are available, indicating that 15 to 60% of calves in the United States of America and Canada are infected. In 1997, a nationalwide survey was also conducted in Japan, and the survey found that protozoans were observed in 2.14% of faeces for cattle, and 1.10% of faeces for pigs.

As described above, *Cryptosporidium* is parasitic in not only humans, but also in animals over a wide range, leading to considerable damage particularly to domestic animals.

Any therapeutic drug that is clearly effective against cryptosporidiosis has not been found yet. Immunologically normal people can be cured of their *Cryptosporidium* infection with their self-immunocompetence, whereas patients with an immunologic deficiency such as AIDS patients fail to be cured of their *Cryptosporidium* infection with their self-immunocompetence, and diarrhea caused by the present infection may be sometimes fatal. Therefore, there is a need for *Cryptosporidium*-cides or protozoacides.

At present, multidrug therapy combining antibacterial drugs such as *Lactobacillus* preparations, azithromycin (Zithromac®), clarithromycin (Clarith® and Klaricid®), and roxithromycin (Rulid®), has been used. The therapy has not been shown to be highly effective although some reports say that the therapy improves the diarrhea ("®" refers to registered trademark).

Under these circumstances, the present applicant has earlier proposed phenol derivatives useful as preventing or treating cryptosporidiosis preventing/treating agent (Japanese Patent Application Laid-Open Publication No. 2005-112755 (Japanese Patent No. 4553569)).

However, excellent compounds have not been virtually found that are effective at lower concentrations, can be synthesized more easily, and are safer than ascofuranone for the purpose of prevention and treatment of diseases including Trypanosomiasis and cryptosporidiosis induced by protozoans.

CITATION LIST

Patent Documents

Patent Document 1: Japanese Patent Application Laid-Open Publication No. 9-165332
Patent Document 2: Japanese Patent Application Laid-Open Publication No. 2004-231601
Patent Document 3: WO2005/037760
Patent Document 4: Japanese Patent Application Laid-Open Publication No. 2005-112755

Non Patent Documents

Non Patent Document 1: MOLECULAR AND BIOCHEMICAL PARASITOLOGY, 81:127-136. 1996
Non Patent Document 2: Parasitology International, 47:131-137. 1998

SUMMARY OF INVENTION

Technical Problem

An object of the present invention is to provide an excellent compound that is effective at lower concentrations, can be synthesized more easily, and is safer than ascofuranone for the purpose of prevention and treatment of diseases including Trypanosomiasis and cryptosporidiosis induced by protozoans.

Solution to Problem

The present inventors, who have diligently researched and studied in order to solve the problems described above, found that a dihydroxybenzene derivative having a certain side chain has an excellent antiprotozoal effect. The present invention has been completed on the basis of these findings.

The present invention provides a compound represented by Formula (I), an optical isomer thereof, and a pharmaceutically acceptable salt thereof:

[Formula 1]

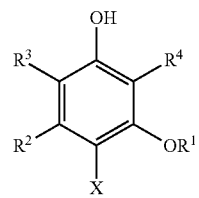

(I)

wherein,
X represents a hydrogen atom or a halogen atom;
$R^1$ represents a hydrogen atom;
$R^2$ represents a hydrogen atom or a $C_{1-7}$ alkyl group;

$R^3$ represents —CHO, —C(=O)$R^5$, —COO$R^5$ (wherein $R^5$ represents a $C_{1-7}$ alkyl group), —CH$_2$OH or —COOH;

$R^4$ represents a $C_{1-16}$ alkyl group having one or more substituents on a terminal carbon atom and/or non-terminal carbon atom(s), a $C_{2-16}$ alkenyl group having one or more substituents on a terminal carbon atom and/or non-terminal carbon atom(s), or a $C_{2-16}$ alkynyl group having one or more substituents on a terminal carbon atom and/or non-terminal carbon atom(s).

Also, the present invention provides a pharmaceutical composition comprising at least one of a compound represented by Formula (I), an optical isomer thereof, and a pharmaceutically acceptable salt thereof, and a pharmaceutically acceptable carrier.

Moreover, the present invention provides an agent for preventing and treating diseases caused by protozoans comprising at least one of a compound represented by Formula (I), an optical isomer thereof, and a pharmaceutically acceptable salt thereof, and a pharmaceutically acceptable carrier.

Furthermore, the present invention provides a compound represented by Formula (I), an optical isomer thereof, and a pharmaceutically acceptable salt thereof that are used for prevention and treatment of diseases caused by protozoans.

Furthermore, the present invention provides a kit comprising at least one of a compound represented by Formula (I), an optical isomer thereof, and a pharmaceutically acceptable salt thereof, and instructions for use.

Advantageous Effects of Invention

The compound represented by Formula (I) above has potent activity against *Trypanosoma, Cryptosporidium* and other protozoans, and are extremely useful for prevention and treatment of various diseases caused by protozoans.

DESCRIPTION OF EMBODIMENTS

The present invention will now be described in detail.

The term "halogen atom" as used herein refers to any of fluorine, chlorine, bromine and iodine atoms.

The term "$C_{1-7}$ alkyl group" as used herein refers to a linear or branched alkyl group having 1 to 7 carbon atoms and examples of such a group includes methyl, ethyl, n-propyl, i-propyl, n-butyl, i-butyl, s-butyl, t-butyl, n-pentyl, n-hexyl, and n-heptyl groups.

The term "$C_{1-16}$ alkyl group" as used herein refers to a linear or branched alkyl group having 1 to 16 carbon atoms and examples of such a group includes methyl, ethyl, n-propyl, i-propyl, n-butyl, i-butyl, s-butyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, and n-hexadecyl groups.

The term "$C_{2-16}$ alkenyl group" as used herein refers to a linear or branched group with one or more carbon-carbon double bonds, having 2 to 16 carbon atoms and examples of such a group includes vinyl, —CH$_2$—CH=C(CH$_3$)—(CH$_2$)$_2$—CH=C(CH$_3$)$_2$, —CH$_2$—CH=C(CH$_3$)—(CH$_2$)$_2$—CH=C(CH$_3$)—(CH$_2$)$_2$—CH=C(CH$_3$)$_2$, and —CH=C—CH$_2$—(CH$_2$)n-CH$_2$)$_2$—CH$_3$ (where n is an integer from 1 to 3).

The term "$C_{2-16}$ alkynyl group" as used herein refers to a linear or branched group having 2 to 16 carbon atoms, with one or more carbon-carbon triple bonds or with one triple bond and one or more carbon-carbon double bonds and examples of such a group includes, for example, ethynyl, 2-pentynyl, 2-hexynyl, 2-octynyl, and 7-methyl-6-octen-2-ynyl.

The term "$C_{1-16}$ alkyl group having one or more substituents on a terminal carbon atom" as used herein refers to a linear or branched alkyl group having 1 to 16 carbon atoms, which has one or more substituents on a carbon atom that is the most distal to the carbon atom of the alkyl group attached to a carbon atom of the benzene ring in a compound of Formula (I). Examples of the substituents include —COOH, —COORa (wherein Ra represents a $C_{1-7}$ alkyl group), —CHO, —COOCH$_2$CH(OH)CH$_2$OH, —COO—CH$_2$—Rb (wherein Rb represents a group formed by removing one hydrogen atom on a carbon atom of aromatic hydrocarbons, such as benzene, naphthalene, and anthracene), —O—CO-Rc (wherein Rc represents a $C_{1-7}$ alkyl group), —OH, —O-Rd (Rd represents a $C_{1-7}$ alkyl group), —O—CH$_2$—O—CH$_3$, —HET (HET represents a group formed by removing one hydrogen atom on a carbon or nitrogen atom of heterocyclic compounds (for example, pyridine, furan, thiophene, furanone, pyrane, pyranone, imidazole, 1,3-dioxolane, oxirane, and 3,3-dimethyloxirane)), and —O-HET (HET is defined as above).

The term "$C_{1-16}$ alkyl group having one or more substituents on non-terminal carbon atom(s)" as used herein refers to a linear or branched alkyl group having 1 to 16 carbon atoms, which has one or more substituents on carbon atom(s) other than a carbon atom that is the most distal to the carbon atom of the alkyl group attached to a carbon atom of the benzene ring in a compound of Formula (I). Examples of the substituents include —COOH, —COORa (wherein Ra represents a $C_{1-7}$ alkyl group), —CHO, —COOCH$_2$CH(OH)CH$_2$OH, —COO—CH$_2$—Rb (wherein Rb represents a group formed by removing one hydrogen atom on a carbon atom of aromatic hydrocarbons, such as benzene, naphthalene, and anthracene), —O—CO-Rc (wherein Rc represents a $C_{1-7}$ alkyl group), —OH, —O-Rd (Rd represents a $C_{1-7}$ alkyl group), —O—CH$_2$—O—CH$_3$, —HET (wherein HET represents a group formed by removing one hydrogen atom on a carbon or nitrogen atom of heterocyclic compounds (for example, pyridine, furan, thiophene, furanone, pyrane, pyranone, imidazole, 1,3-dioxolane, oxirane, and 3,3-dimethyloxirane)), and —O-HET (wherein HET is defined as above).

The term "$C_{2-16}$ alkenyl group having one or more substituents on a terminal carbon atom" as used herein refers to a linear or branched alkyl group having 2 to 16 carbon atoms, which has one or more substituents on a carbon atom that is the most distal to the carbon atom of the alkenyl group attached to a carbon atom of the benzene ring in a compound of Formula (I). The term "alkenyl" also includes alkenyl groups with two or more carbon-carbon double bonds. Examples of the substituents include —COOH, —COORa (wherein Ra represents a $C_{1-7}$ alkyl group), —CHO, —COOCH$_2$CH(OH)CH$_2$OH, —COO—CH$_2$—Rb (wherein Rb represents a group formed by removing one hydrogen atom on a carbon atom of aromatic hydrocarbons, such as benzene, naphthalene, and anthracene), —O—CO-Rc (wherein Rc represents a $C_{1-7}$ alkyl group), —OH, —O-Rd (Rd represents a $C_{1-7}$ alkyl group), —O—CH$_2$—O—CH$_3$, —HET (HET represents a group formed by removing one hydrogen atom on a carbon or nitrogen atom of heterocyclic compounds (for example, pyridine, furan, thiophene, furanone, pyrane, pyranone, imidazole, 1,3-dioxolane, oxirane, and 3,3-dimethyloxirane)), and —O-HET (HET is defined as above).

The term "$C_{2-16}$ alkenyl group having one or more substituents on a non-terminal carbon atom" as used herein refers to a linear or branched alkyl group having 2 to 16 carbon atoms, which has one or more substituents on carbon atom(s) other than a carbon atom that is the most distal to the carbon atom of the alkenyl group attached to a carbon atom of the benzene ring in a compound of Formula (I). The term "alkenyl" also includes alkenyl groups with two or more carbon-carbon double bonds. Examples of the substituents include —COOH, —COORa (wherein Ra represents a $C_{1-7}$ alkyl group), —CHO, —COOCH$_2$CH(OH)CH$_2$OH, —COO—CH$_2$—Rb (wherein Rb represents a group formed by removing one hydrogen atom on a carbon atom of aromatic hydrocarbons, such as benzene, naphthalene, and anthracene), —O—CO-Rc (wherein Rc represents a $C_{1-7}$ alkyl group), —OH, —O-Rd (Rd represents a $C_{1-7}$ alkyl group), —O—CH$_2$—O—CH$_3$, —HET (HET represents a group formed by removing one hydrogen atom on a carbon or nitrogen atom of heterocyclic compounds (for example, pyridine, furan, thiophene, furanone, pyrane, pyranone, imidazole, 1,3-dioxolane, oxirane, and 3,3-dimethyloxirane)), and —O-HET (HET is defined as above above).

The term "$C_{2-16}$ alkynyl group having one or more substituents on a terminal carbon atom" as used herein refers to a linear or branched alkyl group having 2 to 16 carbon atoms, which has one or more substituents on a carbon atom that is the most distal to the carbon atom of the alkynyl group attached to a carbon atom of the benzene ring in a compound of Formula (I). The term "alkynyl" also includes alkynyl groups with two or more carbon-carbon triple bonds. Examples of the substituents include —COOH, —COORa (wherein Ra represents a $C_{1-7}$ alkyl group), —CHO, —COOCH$_2$CH(OH)CH$_2$OH, —COO—CH$_2$—Rb (wherein Rb represents a group formed by removing one hydrogen atom on a carbon atom of aromatic hydrocarbons, such as benzene, naphthalene, and anthracene), —O—CO-Rc (wherein Rc represents a $C_{1-7}$ alkyl group), —OH, —O-Rd (Rd represents a $C_{1-7}$ alkyl group), —O—CH$_2$—O—CH$_3$, —HET (HET represents a group formed by removing one hydrogen atom on a carbon or nitrogen atom of heterocyclic compounds (for example, pyridine, furan, thiophene, furanone, pyrane, pyranone, imidazole, 1,3-dioxolane, oxirane, and 3,3-dimethyloxirane)), and —O-HET (HET is defined as above).

The term "$C_{2-16}$ alkynyl group having one or more substituents on a non-terminal carbon atom" as used herein refers to a linear or branched alkyl group having 2 to 16 carbon atoms, which has one or more substituents on carbon atom(s) other than a carbon atom that is the most distal to the carbon atom of the alkynyl group attached to a carbon atom of the benzene ring in a compound of Formula (I). The term "alkynyl" also includes alkynyl groups with two or more carbon-carbon triple bonds. Examples of the substituents include —COOH, —COORa (wherein Ra represents a $C_{1-7}$ alkyl group), —CHO, —COOCH$_2$CH(OH)CH$_2$OH, —COO—CH$_2$—Rb (wherein Rb represents a group formed by removing one hydrogen atom on a carbon atom of aromatic hydrocarbons, such as benzene, naphthalene, and anthracene), —O—CO-Rc (wherein Rc represents a $C_{1-7}$ alkyl group), —OH, —O-Rd (Rd represents a $C_{1-7}$ alkyl group), —O—CH$_2$—O—CH$_3$, —HET (HET represents a group formed by removing one hydrogen atom on a carbon or nitrogen atom of heterocyclic compounds (for example, pyridine, furan, thiophene, furanone, pyrane, pyranone, imidazole, 1,3-dioxolane, oxirane, and 3,3-dimethyloxirane)), and —O-HET (HET is defined as above above).

Some of the compounds of the present invention may have optical isomers, and all respective optical isomers and mixtures thereof are within the scope of the present invention. The pharmaceutical composition of the present invention may include any of racemates and optical isomers of the compounds of the present invention. The optical isomers can be obtained by resolution of the racemate by well-known methods including, for example, preferential crystallization, column chromatography using an optically active stationary phase and a method of preparing diastereomers.

Pharmaceutically acceptable salts of the compounds of the present invention or their optical isomers include, for example, the following salts.

Salts of the compounds of Formula (I) having a phenolic OH include sodium, potassium, lithium, and ammonium salts.

Salts of the compounds of Formula (I) wherein X represents COOH include sodium, potassium, lithium, and ammonium salts.

Carriers that are used in the pharmaceutical composition of the present invention can include any additives that are well-known in the art of formulation. Illustrative examples of such carriers include an excipient, a diluent, a humectant, a suspending agent, an emulsifier, a dispersant, an adjuvant, a sweetening agent, a colorant, a flavor, a buffering agent, an antiseptic, a preservative, a buffering agent, a binder and a stabilizer, and necessary carrier can be selected from the well-known carriers customarily used in accordance with the target dosage form. Examples of excipients or adjuvants include, for example, lactose, different types of starch (for example, corn starch), chitin, chitosan, glucose, sucrose, cellulose, methyl cellulose, carboxymethyl cellulose, magnesium stearate, lauryl sulfate salt, talc, plant oils (for example, soybean oil, groundnut oil, olive oil), and lecithin.

Furthermore, the pharmaceutical composition of the present invention may contain glycerol. The amount of glycerol added can be suitably adjusted if necessary.

The dosage of the respective compounds according to the present invention varies depending on the medical conditions and symptoms, and the compounds are preferably administered orally in an amount of 10 to 1,000 mg/Kg body weight since protozoans, such as *Trypanosoma* and *Cryptosporidium*, are parasitic in the intestinal tract. This can achieve the object of the present invention. When used as a pharmaceutical, the compound of the present invention is preferably formulated into tablets or capsules and dosage forms suitable for oral administration by neutralizing with alkali to dissolve in water or mixing with a suspending agent, an excipient or its adjuvant. Moreover, enteric coated tablets, which prevent the compound from decomposing in the stomach and deliver it to the intestine tract without its decomposition, are preferred. The enteric coated tablets can be produced using excipients or their adjuvants, including lactose, different types of starch, glucose, fructose, cellulose, methyl cellulose, carboxymethyl cellulose, magnesium stearate, lauryl sulfate salt, talc, plant oils, and lecithin.

A kit for preventing or treating diseases induced by protozoans, such as *Trypanosoma* and *Cryptosporidium*, includes at least one of a compound represented by Formula (I), an optical isomer thereof, and a pharmaceutically acceptable salt thereof, as well as instructions for use.

Different compounds of the present invention are synthesized by different methods. For more information, see the following examples.

EXAMPLES

Now, the present invention will be specifically illustrated with reference to the following examples, which do not limit the scope of the invention.

1. Derivatives 215-15-COOEt, 215-15-COO$^i$Pr, and 215-13-COOH

Scheme 1.

[Formula 2]

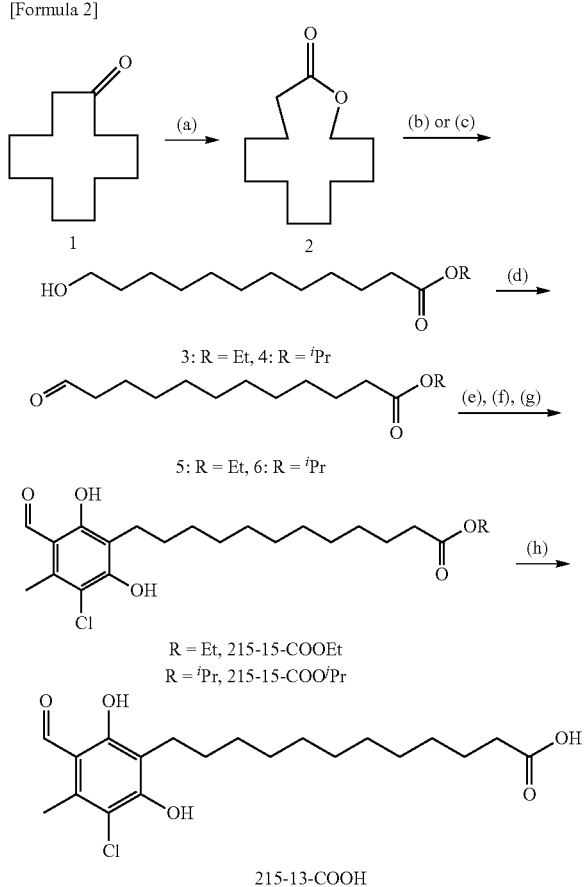

R = Et, 215-15-COOEt
R = $^i$Pr, 215-15-COO$^i$Pr 215-13-COOH

Reagents: (a) H$_2$O$_2$, maleic anhydride, Ac$_2$O, CHCl$_3$, (b) EtOH, H$_2$SO$_4$, (c) i) KOH, MeOH ii) $^i$PrOH, H$_2$SO$_4$, (d) DMSO, (COCl)$_2$, Et$_3$N, CHCl$_3$, (e) 112, KOH, CaCl$_2$, MeOH, (f) H$_3$PO$_4$, AcOH, (g) H$_2$, Pd—C, EtOAC, (h) NaOH, acetone/H$_2$O.

Ethyl 12-(3-chloro-5-formyl-2,6-dihydroxy-4-methylphenyl)dodecanoate (215-15-COOEt)

30% aqueous hydrogen peroxide (10 ml, 98 mmol) was added to a solution of acetic anhydride (12.5 ml, 132 mmol) in CHCl$_3$ (16 ml) at 0° C., and the mixture was stirred for one hour at the same temperature. Maleic anhydride (10.0 g, 102 mmol) was then added as a solid to the reaction mixture, which was allowed to warm to room temperature with stirring for 2 hours. The evolution of heat from the reaction solution was observed, and then cyclododecanone (Compound 1, 2.52 g, 13.8 mmol) was added as a solid to the reaction solution, which was stirred at 35° C. for 16 hours. The reaction solution was allowed to warm to room temperature, and then further cooled to 0° C. to precipitate maleic acid. The precipitated maleic acid was filtered off. The filtrate was washed with H$_2$O, and subsequently with an aqueous solution prepared so as to contain 10% KOH and 10% Na$_2$SO$_3$, and with saturated brine, followed by drying over Na$_2$SO$_4$ After evaporation of the solvent, the residue was loaded on column chromatography on silica gel (Hexane:EtOAc=1:1) to yield a crude product of Compound 2. This product was used directly in the next reaction without further purification.

Sulfuric acid (0.5 ml) was added to a solution of Compound 2 (crude 2.70 g) in EtOH (100 ml) at room temperature, and the mixture was stirred and heated at 70° C. for 17 hours. After the solvent was mostly evaporated, the residue was extracted with EtOAc. The organic layer was washed with a saturated aqueous NaHCO$_3$ solution then with a saturated aqueous NaCl solution, and was dried over Na$_2$SO$_4$. After evaporation of the solvent, the residue was purified by column chromatography on silica gel (Hexane:EtOAc=7:1 to 3:1) to yield the corresponding ethyl ester (Compound 3) (1.85 g, 55% for 2 steps).

[Formula 3]
$^1$H-NMR (400 MHz, CDCl$_3$) δ 4.14 (2H, q, J=7.3 Hz, CO$_2$CH$_2$CH$_3$), 3.64 (2H, t, J=6.4 Hz, CH$_2$OH), 2.26 (2H, t, J=7.5 Hz, CH$_2$CO$_2$Et), 1.71 (1H, br, OH), 1.68-1.53 (4H, m, CH$_2$CH$_2$OH & CH$_2$CH$_2$CO$_2$Et), 1.28 {14H, m, (CH$_2$)$_7$}, 1.26 (3H, t, J=7.3 Hz, CO$_2$CH$_2$CH$_3$).

Oxalyl chloride (1.16 ml, 13.5 mmol) was added to CHCl$_3$ (30 ml) at room temperature in a stream of argon, and the mixture was cooled to −55° C. DMSO (1.90 ml, 26.8 mmol) was added dropwise to the mixture. After 15 minutes stirring, a solution of Compound 3 (1.63 g, 6.67 mmol) in CHCl$_3$ (15 ml) was added dropwise to the reaction mixture with stirring for 3 more hours. After addition of Et$_3$N (5.6 ml, 40 mmol), the reaction mixture was stirred for 45 minutes with the reaction temperature allowed to rise to 0° C. The addition of H$_2$O quenched the reaction. The organic layer was separated, and the aqueous layer was extracted with EtOAc. The combined organic layer was washed with a saturated aqueous NH$_4$Cl solution then with a saturated aqueous NaCl solution, and was dried over Na$_2$SO$_4$. After evaporation of the solvent, the residue was purified by column chromatography on silica gel (Hexane:EtOAc=5:1) to yield a solid product. The obtained solid was further purified by recrystallization (Hexane:EtOAc=10:1) to yield the aldehyde (Compound 5) (1.53 g, 95%).

[Formula 4]
Mp. 60-61° C.
$^1$H-NMR (500 MHz, CDCl$_3$) δ 9.77 (1H, t, J=1.8 Hz, CHO), 4.12 (2H, q, J=7.1 Hz, CO$_2$CH$_2$CH$_3$), 2.42 (2H, dt, J=1.8, 7.3 Hz, CH$_2$CH$_2$CHO), 2.28 (2H, t, J=7.6 Hz, CH$_2$CO$_2$Et), 1.65-1.58 (4H, m, CH$_2$CH$_2$CHO and CH$_2$CH$_2$CO$_2$Et), 1.28 {12H, br, (CH$_2$)$_6$}, 1.25 (3H, t, J=7.1 Hz, CO$_2$CH$_2$CH$_3$).

CaCl$_2$.2H$_2$O (0.200 g, 1.360 mmol) was added to a solution of 3-Chloro-4,6-dihydroxy-2-methylbenzaldehyde (hereinafter, abbreviated to Compound 112, 0.285 g, 1.527 mmol) in MeOH (1.0 ml), and the mixture was cooled to 0° C. KOH (1.1 M in MeOH, 2.3 ml, 2.5 mmol) was added to this cooled mixture, which was stirred for 5 minutes. Then, a solution of Compound 5 (0.447 g, 1.844 mmol) in MeOH (1.0 ml) was added dropwise to the mixture, which was allowed to warm to room temperature with stirring for 16 hours. A 0.1 M aqueous KOH solution (10 ml) was added to the reaction solution, which was extracted with EtOAc three times. The combined organic layer was washed with a saturated aqueous NaCl solution, and was dried over Na$_2$SO$_4$. After evaporation of the solvent, the residue was purified by column chromatography on silica gel (Hexane:EtOAc=3:1) to yield the corresponding aldol adduct (0.145 g, 22%).

H$_3$PO$_4$ (0.06 ml) was added to a solution of the obtained secondary alcohol (0.075 g, 0.175 mmol) in AcOH (1.5 ml), and the mixture was stirred at 70° C. for 6 hours. The reaction solution was allowed to warm to room temperature, and then diluted with H$_2$O and EtOA. The organic layer was separated, and the aqueous layer was then extracted with EtOAc twice. The combined organic layer was washed with a saturated aqueous NaHCO$_3$ solution then with a saturated aqueous NaCl solution, and was dried over Na$_2$SO$_4$. After evaporation of the solvent, the residue was purified by column chromatography on silica gel (Hexane:EtOAc=5:1) to yield a solid product. The obtained solid was further purified by recrystallization (Hexane:EtOAc=10:1) to yield the corresponding olefin (0.048 g, 67%).

The obtained olefin (42 mg, 0.10 mmol) was dissolved in EtOAc (5 ml), and the solution was cooled to 0° C., followed by addition of a catalytic amount of Pd—C. This mixture was stirred for 2 hours under a hydrogen atmosphere. The Pd—C was filtered out, and the solvent was then evaporated. The residue was purified by column chromatography on silica gel (Hexane:EtOAc=4:1). The obtained solid was recrystallized from hexane to yield the target substance (19.5 mg, 47%).

[Formula 5]

Mp. 59-60° C.

$^1$H-NMR (400 MHz, CDCl$_3$) δ 12.65 (1H, s, Ar—O$\underline{H}$), 10.14 (1H, s, Ar—C$\underline{H}$O), 6.33 (1H, s, Ar—O$\underline{H}$), 4.12 (2H, q, J=7.2 Hz, CO$_2$CH$_2$C$\underline{H}_3$), 2.66 (2H, t, J=7.7 Hz, ArC$\underline{H}_2$), 2.61 (3H, s, Ar—C$\underline{H}_3$), 2.28 (2H, t, J=7.3 Hz, C$\underline{H}_2$CO$_2$Et), 1.63-1.56 (2H, m, C$\underline{H}_2$), 1.54-1.49 (2H, m, C$\underline{H}_2$), 1.38-1.24 {17H, m, (C$\underline{H}_2$)$_8$ & CO$_2$CH$_2$C$\underline{H}_2$}.

IR (KBr) 3348, 2930, 2853, 1736, 1610, 1452, 1416, 1377, 1327, 1279, 1240, 1167, 1128, 1020, 916, 860, 785, 708, 590 cm$^{-1}$.

HRMS (EI) calcd. For C$_{22}$H$_{33}$ClO$_5$: 412.2018. found 412.2032.

Isopropyl 12-(3-chloro-5-formyl-2,6-dihydroxy-4-methylphenyl)dodecanoate (215-15-COO$^i$Pr).

Compound 2 (crude, 5.418 g) was refluxed in KOH (1.5 M in MeOH, 40 ml, 60 mmol) for 3 hours. The reaction solution was allowed to warm to room temperature, and then poured into H$_2$O. This mixture was washed with EtOAc twice, and the aqueous layer was then acidified with 2 M HCl, and was extracted with EtOAc twice. The combined organic layer was washed with a saturated aqueous NaCl solution, and was dried over Na$_2$SO$_4$. After evaporation of the solvent, precipitated crude crystals were recrystallized from a mixed solvent of acetone:hexane=1:5 to yield the corresponding carboxylic acid (4.326 g, 72% for 2 steps).

[Formula 6]

Mp. 82-83° C.

$^1$H-NMR (400 MHz, CDCl$_3$) δ 3.65 (2H, t, J=6.6 Hz, C$\underline{H}_2$OH), 2.35 (2H, t, J=7.5 Hz, C$\underline{H}_2$CO$_2$H), 1.67-1.53 (4H, m, C$\underline{H}_2$CH$_2$OH and C$\underline{H}_2$CH$_2$CO$_2$Et), 1.28 {16H, br, CH$_2$O$\underline{H}$, COO$\underline{H}$ & (C$\underline{H}_2$)$_7$}.

H$_2$SO$_4$ (0.5 ml) was added to a solution of this carboxylic acid (0.803 g, 3.71 mmol) in $^i$PrOH (50 ml) at room temperature, and the mixture was stirred at 70° C. for 20 hours. The reaction solution was allowed to warm to room temperature, and then the solvent was evaporated to about half its volume. The residue was poured into H$_2$O. After extraction with EtOAc twice, the combined organic layer was washed with saturated aqueous NaCO$_3$ and a saturated aqueous NaCl solution, and was dried over Na$_2$SO$_4$. After evaporation of the solvent, the residue was purified by column chromatography on silica gel (Hexane:EtOAc=4:1 to 1:1) to prepare the corresponding isopropyl ester (Compound 4) (0.680 g, 71%).

[Formula 7]

$^1$H-NMR (400 MHz, CDCl$_3$) δ 5.00 {2H, sep, J=6.2 Hz, OC$\underline{H}$(CH$_3$)$_2$}, 3.64 (2H, t, J=5.9 Hz, C$\underline{H}_2$OH), 2.29 (2H, t, J=7.5 Hz, C$\underline{H}_2$CO$_2$Et), 1.68-1.53 (4H, m, C$\underline{H}_2$CH$_2$OH and C$\underline{H}_2$CH$_2$CO$_2$Et), 1.42 (1H, br, O$\underline{H}$), 1.27 {14H, m, (C$\underline{H}_2$)$_7$}, 1.22 {6H, d, J=6.2 Hz, OCH(C$\underline{H}_3$)$_2$}.

Then, the similar process gave the target product. 3% yield from Compound 4.

[Formula 8]

Mp. 56° C.

$^1$H-NMR (400 MHz, CDCl$_3$) δ 12.66 (1H, s, Ar—O$\underline{H}$), 10.14 (1H, s, Ar—C$\underline{H}$O), 6.33 (1H, s, Ar—O$\underline{H}$), 5.00 {1H, m, CO$_2$C$\underline{H}$(CH$_3$)$_2$}, 2.66 (2H, t, J=7.7 Hz, Ar—C$\underline{H}_2$), 2.61 (3H, s, Ar—C$\underline{H}_3$), 2.25 {2H, t, J=7.5 Hz, C$\underline{H}_2$CO$_2$ $^i$Pr}, 1.65-1.57 (2H, m, C$\underline{H}_2$), 1.54-1.48 (2H, m, C$\underline{H}_2$), 1.26 {14H, br, (C$\underline{H}_2$)$_7$}, 1.22 {6H, d, J=6.2 Hz, CH(C$\underline{H}_3$)$_2$}.

IR (KBr) 3287, 2922, 2845, 1703, 1616, 1456, 1421, 1377, 1279, 1248, 1196, 1105, 836, 631, 590 cm$^{-1}$.

HRMS (EI) Found: 426.2186. Calcd. for C$_{23}$H$_{35}$ClO$_5$: 426.2173.

12-(3-Chloro-5-formyl-2,6-dihydroxy-4-methylphenyl)dodecanoic acid (215-13-COOH)

NaOH (21 mg, 0.48 mmol) was added to a mixed solution of 215-15-COOEt (101 mg, 0.246 mmol) in acetone (1.3 ml)/H$_2$O (0.7 ml) at room temperature followed by stirring for 12 hours. After dilution of the reaction solution with EtOAc, the diluted solution was acidified with a 1 M aqueous HCl solution. After addition of a saturated aqueous NaCl solution, the organic layer was separated. The aqueous layer was then extracted with EtOAc twice, and the combined organic layer was dried over Na$_2$SO$_4$. After evaporation of the solvent, the residue was purified by column chromatography on silica gel (Hexane:EtOAc=2:1) to yield the target product.

[Formula 9]

Mp. 130-131° C.

$^1$H-NMR (400 MHz, CDCl$_3$) δ 12.66 (1H, s, Ar—O$\underline{H}$), 10.14 (1H, s, Ar—C$\underline{H}$O), 6.34 (1H, br, Ar—O$\underline{H}$), 2.66 (2H, t, J=7.7 Hz, Ar—C$\underline{H}_2$), 2.61 (3H, s, Ar—C$\underline{H}_3$), 2.35 (2H, t, J=7.3 Hz, C$\underline{H}_2$COOH), 1.65-1.46 (4H, m, C$\underline{H}_2$CH$_2$COOH & ArCH$_2$C$\underline{H}_2$), 1.35 {14H, br, (C$\underline{H}_2$)$_7$}.

IR (KBr) 3360, 2920, 2855, 1715, 1612, 1472, 1420, 1283, 1246, 1180, 1126, 937, 853, 785, 588 cm$^{-1}$.

HRMS (EI) Found: 384.1712. Calcd. for C$_{20}$H$_{29}$ClO$_5$: 384.1704.

2. Compound 215-13-COOEt

Scheme 2.

[Formula 10]

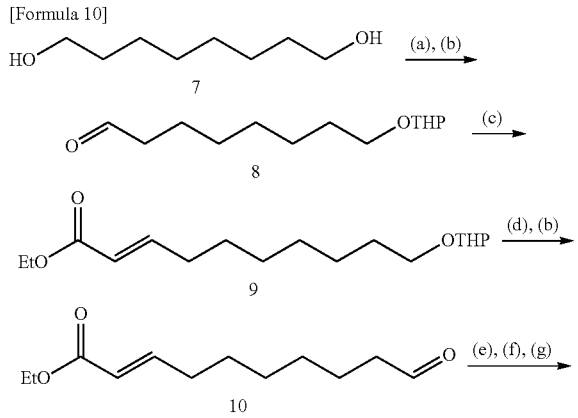

-continued

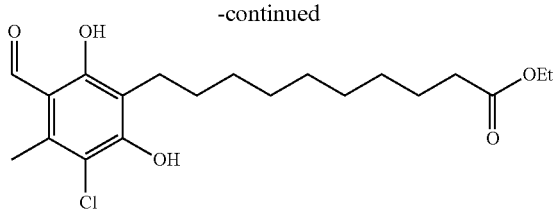

215-13-COOEt

Reagents: (a) DHP, PPTS, CHCl₃ (b) Swern oxidation (c) (EtO)₂P(O)CH₂CO₂Et, NaH, THF (d) PPTS, EtOH (e) 112, KOH, CaCl₂, MeOH (f) H₃PO₄, AcOH (g) H₂, Pd—C, EtOHC.

Ethyl 10-(3-chloro-5-formyl-2,6-dihydroxy-4-methylphenyl)decanoate (215-13-COOEt)

DHP (3.46 ml, 37.9 mmol) and a catalytic amount of PPTS were added to a solution of 1,8-octanediol (Compound 7, 5.85 g, 40.0 mmol) in CHCl₃ (100 ml) in a stream of argon at room temperature, and the mixture was stirred for 16 hours. The reaction solution was stirred for 5 minutes after addition of H₂O. The organic layer was separated, and the aqueous layer was extracted with EtOAc. The combined organic layer was washed with a saturated aqueous NaHCO₃ solution then with a saturated aqueous NaCl solution, and was dried over Na₂SO₄. After evaporation of the solvent, the residue was purified by column chromatography on silica gel (Hexane:EtOAc=3:1 to 2:1) to yield the corresponding THP ether (4.95 g, 54%).

DMSO (2.8 ml, 40 mmol) was added dropwise to a solution of oxalyl chloride (2.0 ml, 23 mmol) in CHCl₃ (50 ml) at −55° C. After 15 minutes, a solution of a primary alcohol (2.18 g, 9.46 mmol) in CHCl₃ (20 ml) was added dropwise to the mixture, which was stirred for 2 hours. This mixture was stirred for 45 minutes while being allowed to warm to 0° C. after Et₃N (8.0 ml, 58 mmol) was added dropwise to the mixture. H₂O was added to the reaction solution, and the organic layer was separated followed by extraction of the aqueous layer with EtOAc. The combined organic layer was washed with a saturated aqueous NaCl solution, and was dried over Na₂SO₄. After evaporation of the solvent, the residue was purified by column chromatography on silica gel (Hexane:EtOAc=5:1) to yield the aldehyde (Compound 8) (1.95 g, 90%).

[Formula 11]
¹H-NMR (400 MHz, CDCl₃) δ 9.77 (1H, t, J=1.8 Hz, CHO), 4.57 (1H, dd, J=2.6, 4.8 Hz, OCHO), 3.90-3.84 (1H, m, CH₂O), 3.73 (1H, td, J=6.8, 9.6 Hz, CH₂O), 3.53-3.48 (1H, m, CH₂O), 3.38 (1H, td, J=6.6, 9.5 Hz, CH₂O), 2.42 (2H, dt, J=1.8, 7.5 Hz, CH₂CHO), 1.87-1.78 (1H, m, OCHCH₂), 1.75-1.68 (1H, m, OCHCH₂), 1.67-1.49 (8H, m, 4×CH₂), 1.43-1.28 (6H, m, 3×CH₂).

Next, diethyl phosphonoacetic acid diethyl ether (1.45 ml, 7.25 mmol) was added to a suspension of NaH (50% purity, 0.378 g, 7.88 mmol) in THF (50 ml) in a stream of argon at 0° C., and the mixture was stirred for 1.5 hours. This reaction solution was cooled to −60° C., followed by dropwise addition of a solution of Compound 8 (1.44 g, 6.31 mmol) in THF (15 ml). After stirred for 30 minutes at the same temperature, the reaction solution was allowed to warm to room temperature, and stirred for 18 hours. This solution was again cooled to 0° C. H₂O was added in small portions to the cooled solution to decompose excess NaH, followed by addition of additional H₂O and extraction with Et₂O twice. The combined organic layer was washed with a saturated aqueous NaCl solution, and was dried over Na₂SO₄. After evaporation of the solvent, the residue was purified by column chromatography on silica gel (Hexane:EtOAc=7:1) to yield the corresponding ethyl ester (Compound 9) (1.62 g, 86%).

A catalytic amount of PPTS was added to a solution of the ester (Compound 9) (1.15 g, 3.85 mmol) in EtOH (30 ml) at room temperature, and the mixture was heated and stirred at 60° C. for 2.5 hours. After the solvent was mostly evaporated, the residue was dissolved in EtOAc. This solution was washed H₂O, a saturated aqueous NaHCO₃ solution, and a saturated aqueous NaCl solution in this order, and was dried over Na₂SO₄. After evaporation of the solvent, the residue was purified by column chromatography on silica gel (Hexane:EtOAc=7:1) to yield the corresponding primary alcohol (0.63 g, 76%).

[Formula 12]
¹H-NMR (500 MHz, CDCl₃) δ 6.96 (1H, dt, J=7.0, 15.6 Hz, CH=CHCO₂Et), 5.81 (1H, dt, J=1.5, 15.6 Hz, CH=CHCO₂Et), 4.18 (2H, q, J=7.1 Hz, CO₂CH₂CH₃), 3.64 (2H, t, J=6.5 Hz, CH₂CH₂OH), 2.19 (2H, ddt, J=1.4, 7.1, 7.6 Hz, CH₂CH=CH), 1.56 (2H, m, CH₂CH₂OH), 1.46 (2H, m, CH₂CH₂CH=CH), 1.37-1.31 {7H, m, (CH₂)₃ & OH}, 1.29 (3H, t, J=7.1 Hz, CO₂CH₂CH₃).

Subsequently, the resulting primary alcohol was converted into the corresponding aldehyde (10) through Swern oxidation (0.45 g, 72%).

[Formula 13]
¹H-NMR (400 MHz, CDCl₃) δ 9.77 (1H, s, CHO), 6.95 (1H, dt, J=7.0, 15.8 Hz, CH=CHCO₂Et), 5.81 (1H, dt, J=1.4, 15.8 Hz, CH=CHCO₂Et), 4.19 (2H, q, J=7.2 Hz, CO₂CH₂CH₃), 2.43 (2H, dt, J=1.8, 7.3 Hz, CH₂CHO), 2.20 (2H, ddt, J=1.4, 7.0, 7.3 Hz, CH₂CH=CH), 1.66-1.60 (2H, m, CH₂CH₂CHO), 1.49-1.42 (2H, m CH₂CH₂CH=CH), 1.36-1.32 {4H, m (CH₂)₂}, 1.29 (3H, t, J=7.2 Hz, CO₂CH₂CH₃).

Then, a similar methodology to that described above was employed to yield the target product (2% for 3 steps).

[Formula 14]
Mp. 45-46° C. ¹H-NMR (400 MHz, CDCl₃) δ 12.67 (1H, s, Ar—OH), 10.14 (1H, s, Ar—CHO), 6.39 (1H, s, Ar—OH), 4.12 (2H, q, J=7.3 Hz, CO₂CH₂CH₃), 2.66 (2H, t, J=7.7 Hz, ArCH₂), 2.60 (3H, s, Ar—CH₃), 2.28 (2H, t, J=7.3 Hz, CH₂CO₂Et), 1.63-1.56 (2H, m, CH₂), 1.54-1.48 (2H, m, CH₂), 1.31-1.23 {13H, m, (CH₂)₅ and CO₂CH₂CH₃}.

IR (KBr) 3452, 2922, 2853, 1736, 1637, 1468, 1421, 1377, 1327, 1286, 1248, 1175, 1119, 1084, 1018, 920, 843, 802, 726, 586 cm⁻¹. HRMS (EI) calcd. For C₂₀H₂₉ClO₅: 384.1704. found 384.1687.

3. Compounds 200-12-COOMe, 215-12-COOMe, 215-13-COOIPr, and 215-11-COOH

Scheme 3.

[Formula 15]

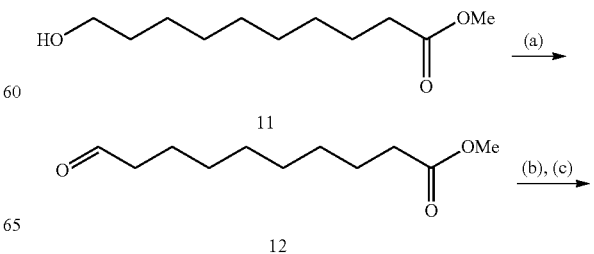

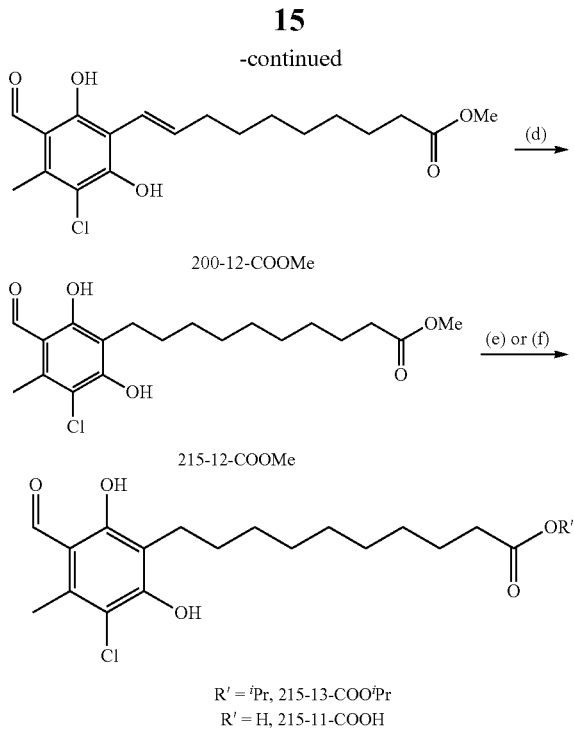

R' = iPr, 215-13-COOiPr
R' = H, 215-11-COOH

Reagents: (a) Swern oxidation (b) 112, KOH, CaCl₂, MeOH (c) H₃PO₄, AcOH (d) H₂, Pd—C, EtOAc (e) iPrOH, H₂SO₄ (f) NaOH, acetone/H₂O.

(E)-Methyl 10-(3-chloro-5-formyl-2,6-dihydroxy-4-methylphenyl)-10-decenoate (200-12-COOMe)

Commercially available methyl 10-hydroxydecanoate (Compound 11) was subjected to Swern oxidation to yield the aldehyde (Compound 12) (59% yield).

[Formula 16]

$^1$H-NMR (400 MHz, CDCl$_3$) δ 9.76 (1H, t, J=1.8 Hz, CHO), 3.67 (3H, s, CO$_2$CH$_3$), 2.42 (2H, dt, J=1.8, 7.3 Hz, CH$_2$CHO), 2.30 (2H, t, J=7.5 Hz, CH$_2$CO$_2$CH$_3$), 1.67-1.57 (4H, m, CH$_2$CH$_2$CHO & CH$_2$CH$_2$CO$_2$CH$_3$), 1.31 {8H, br, (CH$_2$)$_4$}.

Compound 11 was also subjected to aldol reaction with Compound 112 and dehydration under acidic conditions to yield the target product (36% for 2 steps).

[Formula 17]

Mp. 71-72° C.

$^1$H-NMR (400 MHz, CDCl$_3$) δ 13.05 (1H, s, Ar—OH), 10.14 (1H, s, Ar—CHO), 6.65 (1H, dt, J=6.8, 16.2 Hz, ArCH=CH), 6.63 (1H, s, Ar—OH), 6.50 (1H, d, J=16.2 Hz, ArCH=CH), 3.67 (3H, s, COOCH$_3$), 2.61 (3H, s, Ar—CH$_3$), 2.33-2.23 (4H, m, CH=CHCH$_2$ & CH$_2$COOMe), 1.67-1.59 (2H, m, CH$_2$), 1.50-1.45 (2H, m, CH$_2$), 1.34 {6H, br (CH$_2$)$_3$}.

IR (KBr) 3375, 2928, 2853, 1728, 1605, 1452, 1408, 1366, 1315, 1286, 1232, 1136, 1107, 980, 845, 802, 615, 592 cm$^{-1}$.

HRMS (EI) Found: 368.1377. Calcd. for C$_{19}$H$_{25}$O$_5$Cl (M$^+$), 368.1391. Anal. Found: C, 61.97; H, 6.86; Cl, 9.37%. Calcd. for C$_{19}$H$_{25}$O$_5$Cl: C, 61.87; H, 6.83; Cl, 9.61%.

Methyl 10-(3-chloro-5-formyl-2,6-dihydroxy-4-methylphenyl)decanoate (215-12-COOMe)

Compound 200-12-COOEt was catalytically reduced to yield the target product (79% yield).

[Formula 18]

Mp. 87-88° C.

$^1$H-NMR (400 MHz, CDCl$_3$) δ 12.65 (1H, s, Ar—OH), 10.14 (1H, s, Ar—CHO), 6.37 (1H, br, Ar—OH), 3.67 (3H, s, COOCH$_3$), 2.66 (2H, t, J=8.0 Hz, ArCH$_2$), 2.60 (3H, s, Ar—CH$_3$), 2.30 (2H, t, J=7.7 Hz, CH$_2$COOCH$_3$), 1.65-1.57 (2H, m, CH$_2$), 1.57-1.47 (2H, m, CH$_2$), 1.28 {10H, br, (CH$_2$)$_5$}. IR (KBr) 3358, 2928, 2853, 1736, 1611, 1421, 1250, 1171, 1132, 777, 590 cm$^{-1}$.

HRMS (EI) Found: 370.1533. Calcd. for C$_{19}$H$_{27}$ClO$_5$: 370.1547. Anal. Found: C, 61.41; H, 7.32; Cl, 9.43%. Calcd. for C, 61.53; H, 7.34; Cl, 9.67%.

Isopropyl 10-(3-chloro-2,6-dihydroxy-5-formyl-4-methylphenyl)decanoate (215-13-COOIPr)

H$_2$SO$_4$ (0.25 ml) was added to a solution of Compound 215-12-COOMe (114 mg, 0.307 mmol) in 2-propanol (25 ml), the mixture was refluxed for 18 hours. The reaction solution was allowed to warm to room temperature. The solvent was then evaporated, and the residue was extracted with EtOA twice. The combined organic layer was washed with a saturated aqueous NaHCO$_3$ solution then with a saturated aqueous NaCl solution, and was dried over anhydrous Na$_2$SO$_4$. After evaporation of the solvent, the residue was purified by column chromatography on silica gel (Hexane:EtOAc, 7:1) and recrystallization (Hexane:EtOAc=9:1) to yield the target product. The mother liquor was then concentrated, and the residue was purified by column chromatography on silica gel (Hexane:EtOAc=5:1) to yield an additional crop of the target product. Combined yield (83 mg, 68%).

[Formula 19]

Mp. 49° C.

$^1$H-NMR (400 MHz, CDCl$_3$) δ 12.66 (1H, s, Ar—OH), 10.14 (1H, s, Ar—CHO), 6.37 (1H, s, Ar—OH), 5.00 {1H, septet, J=6.2 Hz, CO$_2$CH(CH$_3$)$_2$}, 2.66 (2H, t, J=7.7 Hz, Ar—CH$_2$), 2.60 (3H, s, Ar—CH$_3$), 2.25 {2H, t, J=7.5 Hz, CH$_2$CO$_2$ $^i$Pr}, 1.64-1.57 (2H, m, CH$_2$), 1.54-1.48 (2H, m, CH$_2$), 1.28 {10H, br, (CH$_2$)$_5$}, 1.23 {6H, d, J=6.2 Hz, CH(CH$_3$)$_2$}.

IR (KBr) 3271, 2916, 2845, 1703, 1610, 1468, 1412, 1366, 1325, 1286, 1251, 1217, 1109, 826, 631, 590 cm$^{-1}$.

HRMS (EI) Found: 398.1841. Calcd. for C$_{21}$H$_{31}$ClO$_5$: 398.1860.

10-(3-Chloro-5-formyl-2,6-dihydroxy-4-methylphenyl)decanoic acid (215-11-COOH)

Compound 215-12-COOMe was hydrolyzed by the method above to yield the target product (89% yield).

[Formula 20]

Mp. 154-156° C.

$^1$H-NMR (400 MHz, CDCl$_3$) δ 12.66 (1H, s, Ar—OH), 10.14 (1H, s, Ar—CHO), 6.34 (1H, br, Ar—OH), 2.66 (2H, t, J=7.7 Hz, ArCH$_2$), 2.61 (3H, s, Ar—CH$_3$), 2.35 (2H, t, J=7.5 Hz, CH$_2$COOH), 1.67-1.47 (4H, m, CH$_2$CH$_2$COOH & ArCH$_2$CH$_2$), 1.35 {10H, br, (CH$_2$)$_5$}.

IR (KBr) 3360, 2920, 2853, 1715, 1614, 1470, 1418, 1371, 1236, 1184, 1126, 934, 847, 773, 588 cm$^{-1}$.

HRMS (EI) Found: 356.1408. Calcd. for C$_{18}$H$_{25}$ClO$_5$: 356.1391.

4. Compounds 215-13-COOtBu, 501-16-G, 502-16-G, and 500-15-G

Scheme 4.

[Formula 21]

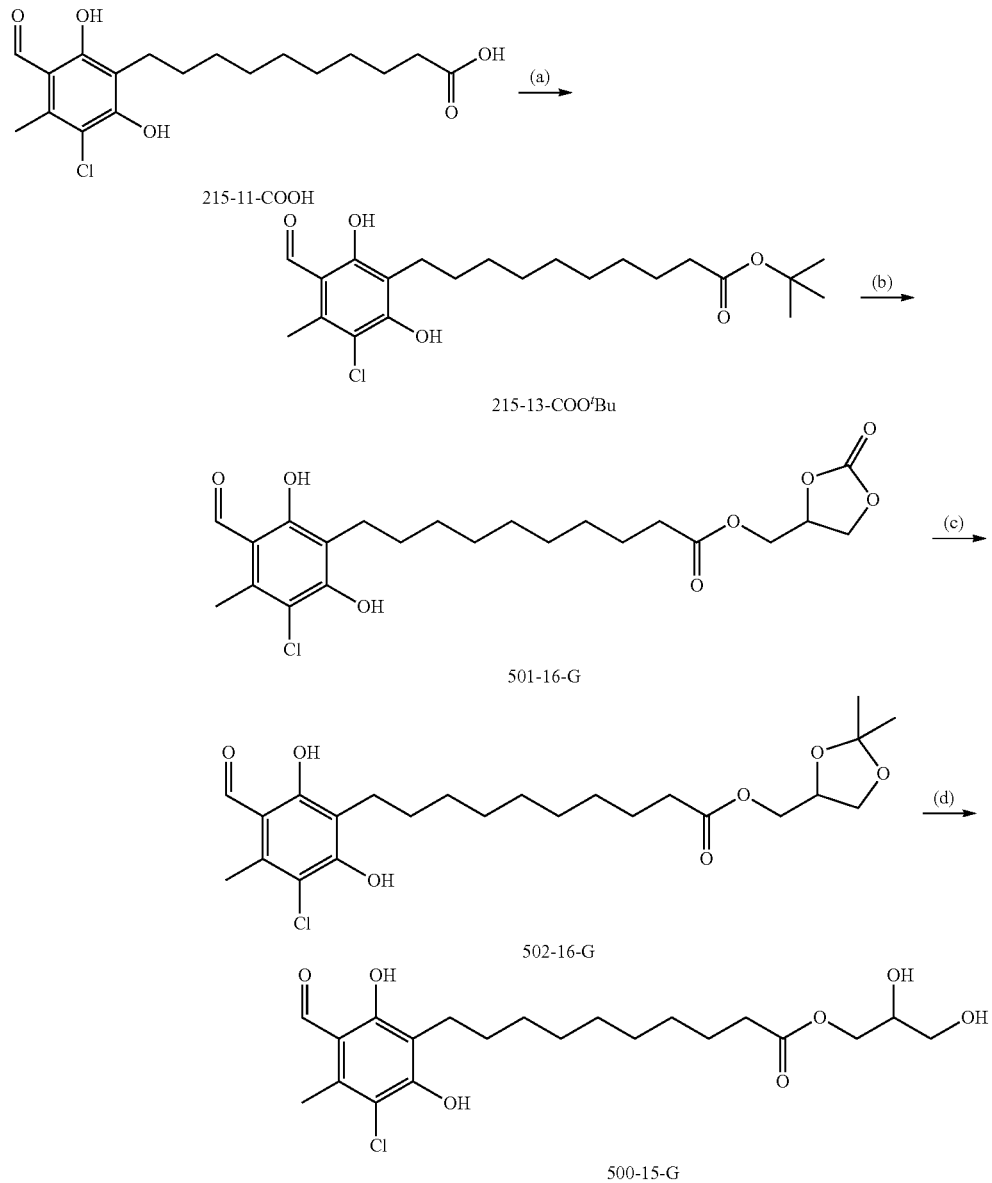

Reagents and conditions: (a) tBuOH, TFAA, toluene (b) 2,2-Dimethyl-1,3-dioxolane-4-methanol, DCC, DMAP, THF (c) Glycerol 1,2-carbonate, DCC, DMAP, THF (d) PPTS, MeOH tert-Butyl 10-(3-chloro-2,6-dihydroxy-5-formyl-4-methylphenyl)decanoate (215-13-COOtBu)

TFAA (0.20 ml, 1.4 mmol) was added to a suspension of Compound 215-11-COOH (144 mg, 0.403 mmol) in toluene (5 ml) at 0° C., and the mixture was allowed to warm to room temperature with stirring for 30 minutes. After checking for complete dissolution of the raw material, the mixture was again cooled to 0° C. tBuOH (0.40 ml, 4.2 mmol) was added to the cooled mixture, which was allowed to warm to room temperature with stirring for 15 hours. A saturated aqueous NaHCO$_3$ solution was added to the reaction solution, which was extracted with EtOAc twice after stirring for 5 minutes. The combined organic layer was washed with a saturated aqueous NaCl solution, and was dried over anhydrous Na$_2$SO$_4$. After evaporation of the solvent, the residue was purified by column chromatography on silica gel (Hexane:EtOAc=7:1 to 4:1) followed by PTLC (Hexane:EtOAc=7:1) to yield the target product (28 mg, 17%).

[Formula 22]

$^1$H-NMR (400 MHz, CDCl$_3$) δ 12.65 (1H, s, Ar—OH̲), 10.14 (1H, s, Ar—CH̲O), 6.40 (1H, br, Ar—OH̲), 2.66 (2H, t, J=7.5 Hz, Ar—CH̲$_2$), 2.60 (3H, s, Ar—CH̲$_3$), 2.20 {2H, t, J=7.5 Hz, CH̲$_2$CO$_2^t$Bu}, 1.62-1.48 (4H, m, CH̲$_2$CH$_2$CO$_2^t$Bu & ArCH$_2$CH̲$_2$), 1.44 {9H, s, (CH̲$_3$)$_3$}, 1.29 {10H, br, (CH̲$_2$)$_5$}.

IR (KBr) 3287, 2922, 2845, 1732, 1616, 1452, 1425, 1366, 1290, 1248, 1213, 1161, 1126, 934, 795, 716, 630, 590, 530 cm$^{-1}$.

1,3 Dioxolane-2-oxo-4-methyl 10-(3-chloro-5-formyl-2,6-dihydroxy-4-methylphenyl)decanoate (501-16-G)

2,2-dimethyl-1,3-dioxolanee-4-methanol (98% purity, 0.25 ml, 2.0 mmol), DMAP (62 mg, 0.51 mmol), and DCC (130 mg, 0.630 mmol) were added to a solution of Compound 215-11-COOH (184 mg, 0.516 mmol) in THF (30 ml) at room temperature followed by stirring for 7 hours. The reaction solution was diluted with a phosphate buffer (pH 6.98) and EtOAc, and was filtered through celite, and the organic layer of the filtrate was separated. The aqueous layer was extracted with EtOAc twice, and the combined organic layer was washed with a saturated aqueous NaCl solution, and was dried over anhydrous Na2SO4. After evaporation of the solvent, the residue was purified by column chromatography on silica gel (Hexane:EtOAc=2:1 to 1:1) followed by PTLC (toluene:EtOAc=9:1). After evaporation of the solvent, the crude product was again purified by column chromatography on silica gel (Hexane:EtOAc=2:1 to 3:2) to yield the target product (78 mg, 33%).

[Formula 23]
Mp. 70-72° C.
$^1$H-NMR (400 MHz, CDCl$_3$) δ 12.65 (1H, s, Ar—O$\underline{H}$), 10.13 (1H, s, Ar—C$\underline{H}$O), 6.49 (1H, br, Ar—O$\underline{H}$), 4.93 {1H, m, CO$_2$CH$_2$C$\underline{H}$OC(O)OCH$_2$}, 4.56 {1H, dd, J=8.4, 8.8 Hz, CO$_2$C$\underline{H}_2$CHOC(O)OCH$_2$}, 4.37 {1H, dd, J=3.3, 12.6 Hz, CO$_2$CH$_2$CHOC(O)OC$\underline{H}_2$}, 4.31 {1H, dd, J=5.8, 8.8 Hz, CO$_2$C$\underline{H}_2$CHOC(O)OCH$_2$}, 4.26 {1H, dd, J=4.2, 12.6 Hz, CO$_2$CH$_2$CHOC(O)OC$\underline{H}_2$}, 2.66 (2H, t, J=7.7 Hz, Ar—C$\underline{H}_2$), 2.60 (3H, s, Ar—C$\underline{H}_3$), 2.37 {2H, t, J=7.5 Hz, CH$_2$C$\underline{H}_2$C(O)O}, 1.65-1.58 (2H, m, C$\underline{H}_2$), 1.55-1.48 (2H, m, C$\underline{H}_2$), 1.29 {10H, br, (C$\underline{H}_2$)$_5$}.
$^{13}$C-NMR (100 MHz, CDCl$_3$) δ 193.24, 173.27, 162.37, 156.26, 154.36, 137.27, 115.68, 113.41, 113.06, 73.75, 66.96, 62.78, 33.83, 29.41, 29.23, 29.18, 29.05, 28.94, 28.25, 24.66, 22.77, 14.40.
IR (KBr) 3362, 2922, 2853, 1788, 1736, 1620, 1599, 1468, 1416, 1398, 1283, 1248, 1165, 1136, 1092, 1040, 878, 752, 586 cm$^{-1}$.
HRMS (EI) Found: 456.1546. Calcd. for C$_{22}$H$_{29}$ClO$_8$: 456.1551.

2,2-Dimethyl-1,3-dioxolanee-4-methyl 10-(3-chloro-5-formyl-2,6-dihydroxy-4-methylphenyl)decanoate (502-16-G)

Esterification was conducted in a similar manner to yield the target product (28% yield).

[Formula 24]
Mp. 55-56° C.
$^1$H-NMR (400 MHz, CDCl$_3$) δ 12.65 (1H, s, Ar—O$\underline{H}$), 10.14 (1H, s, Ar—C$\underline{H}$O), 6.38 (1H, br, Ar—O$\underline{H}$), 4.32 {1H, m, C$\underline{H}$OC(CH$_3$)$_2$OCH$_2$—}, 4.17 {1H, dd, J=4.8, 11.7 Hz, C(O)OC$\underline{H}_2$CH}, 4.11-4.06 {2H, m, CHOC(CH$_3$)$_2$OC$\underline{H}_2$— & C(O)OC$\underline{H}_2$CH}, 3.74 {1H, dd, J=6.2, 8.4 Hz, CHOC(CH$_3$)$_2$OC$\underline{H}_2$}, 2.66 (2H, t, J=7.7 Hz, Ar—C$\underline{H}_2$), 2.60 (3H, s, Ar—C$\underline{H}_3$), 2.33 {2H, t, J=7.7 Hz, CH$_2$C$\underline{H}_2$C(O)O}, 1.65-1.58 (2H, m, C$\underline{H}_2$), 1.54-1.48 (2H, m, C$\underline{H}_2$), 1.43 (3H, s, C$\underline{H}_3$), 1.39 (3H, s, C$\underline{H}_3$), 1.28 {10H, br, (C$\underline{H}_2$)$_5$}.
$^{13}$C-NMR (100 MHz, CDCl$_3$) δ 193.26, 173.69, 162.42, 156.20, 137.24, 115.74, 113.47, 113.04, 109.81, 73.60, 66.35, 64.50, 34.10, 29.47, 29.27, 29.25, 29.14, 29.03, 28.29, 26.67, 25.38, 24.82, 22.82, 14.44.
IR (KBr) 3265, 2922, 2853, 1745, 1620, 1526, 1460, 1425, 1369, 1331, 1244, 1219, 1171, 1132, 1092, 1045, 1007, 980, 932, 851, 795, 712, 625, 596, 534 cm$^{-1}$.
HRMS (EI) Found: 470.2047. Calcd. for C$_{24}$H$_{35}$ClO$_7$: 470.2071.

1-Glyceryl 10-(3-chloro-2,6-dihydroxy-5-formyl-4-methylphenyl)decanoate (500-15-G)

PPTS (10 mg, 40 mmol) was added to a solution of Compound 502-16-G (77 mg, 0.16 mmol) in MeOH (5 ml) at room temperature, and the mixture was stirred at 50° C. for 20 hours. The reaction solution was allowed to warm to room temperature, and then the solvent was evaporated. The residue was purified by column chromatography on silica gel (Hexane:EtOAc=2:1 to EtOAc only) to yield the target product (11 mg, 16%). Also, the methyl ester (Compound 215-12-CO2Me) was produced as a byproduct (10 mg, 17%).

[Formula 25]
$^1$H-NMR (400 MHz, CDCl$_3$) δ 12.64 (1H, s, Ar—O$\underline{H}$), 10.13 (1H, s, Ar—C$\underline{H}$O), 6.62 (1H, br, Ar—O$\underline{H}$), 4.21 {1H, dd, J=4.8, 11.7 Hz, C(O)OC$\underline{H}_2$CH(OH)CH$_2$OH}, 4.15 {1H, dd, J=6.2, 11.7 Hz, C(O)OC$\underline{H}_2$CH(OH)CH$_2$OH}, 3.94 {1H, m, C(O)OCH$_2$C$\underline{H}$(OH)CH$_2$OH}, 3.71 {1H, dd, J=3.6, 11.4 Hz, C(O)OCH$_2$CH(OH)C$\underline{H}_2$OH}, 3.61 {1H, dd, J=5.9, 11.4 Hz, C(O)OCH$_2$CH(OH)C$\underline{H}_2$OH}, 2.98 (1H, br, O$\underline{H}$), 2.65 (2H, t, J=7.5 Hz, Ar—C$\underline{H}_2$), 2.60 (3H, s, Ar—C$\underline{H}_3$), 2.35 {2H, t, J=7.7 Hz, CH$_2$C$\underline{H}_2$C(O)O—}, 2.07 (1H, br, O$\underline{H}$), 1.66-1.58 (2H, m, C$\underline{H}_2$), 1.55-1.49 (2H, m, C$\underline{H}_2$), 1.28 {10H, br, (C$\underline{H}_2$)$_5$}.
IR (KBr) 3314, 2930, 2853, 1740, 1599, 1558, 1468, 1425, 1383, 1335, 1279, 1252, 1182, 1126, 1057, 928, 795, 743, 712, 625, 592, 534 cm$^{-1}$.
HRMS (EI) Found: 430.1783. Calcd. for C$_{21}$H$_{31}$ClO$_7$: 430.1758.

5. Compounds 215-11-COOEt, 215-9-COOH, and 215-18-Anthra

Scheme 5.

[Formula 26]

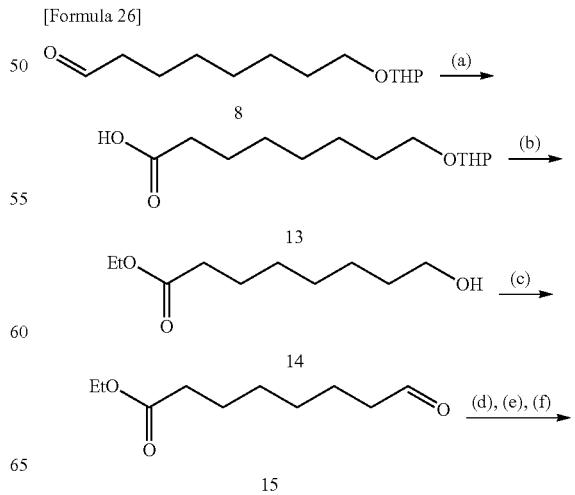

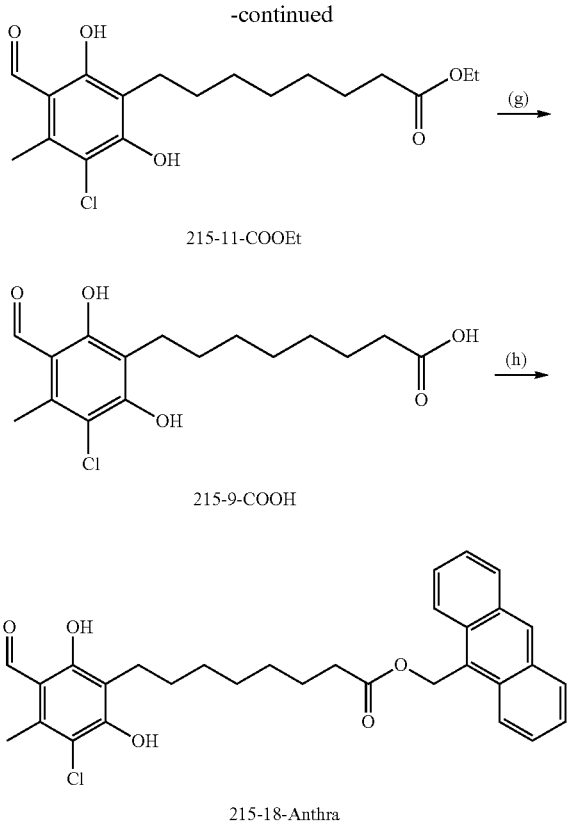

215-11-COOEt 215-9-COOH 215-18-Anthra

Reagents: (a) NaClO₂, H₂O₂, NaH₂PO₄, CH₃CN/H₂O (b) EtOH, H₂SO₄ (c) Swern oxidation (d) 112, KOH, CaCl₂, MeOH (e) H₃PO₄, AcOH (f) H₂, Pd—C, EtOAc (g) NaOH, acetone/H₂O (h) 9-Anthracenemethanol, DCC, DMAP, THF.

Ethyl 8-(3-chloro-5-formyl-2,6-dihydroxy-4-methylphenyl)octanoate (215-11-COOEt)

A solution of $NaH_2PO_4 \cdot 2H_2O$ (3.312 g, 21.23 mmol) in $H_2O$ (10 ml) was added to a solution of the aldehyde (Compound 8, 1.950 g, 8.541 mmol) in MeCN (40 ml) at −15° C., and the mixture was stirred for 10 minutes. $H_2O_2$ (30% in $H_2O$, 7.8 ml, 76 mmol) and 5 minutes later $NaClO_2$ (79% purity, 1.311 g, 11.45 mmol) were added to this mixture, which was stirred for one more hour. A 20% aqueous $Na_2SO_3$ solution was added to the reaction solution, and the mixture was stirred for 10 minutes and poured into a 1 M HCl solution. This mixture was extracted with EtOAc three times, and the combined organic layer was washed with a saturated aqueous NaCl solution, and was dried over $Na_2SO_4$. After evaporation of the solvent, the residue was purified by column chromatography on silica gel (Hexane:EtOAc=4:1 to 2:1) to yield a carboxylic acid (Compound 13) (0.850 g, 41%).

$H_2SO_4$ (0.5 ml) was added to a solution of Compound 13 (0.453 g, 1.984 mmol) in EtOH (20 ml), and the mixture was stirred at 60° C. for 15 hours. After evaporation of the solvent, the mixture was diluted with EtOAc. This diluted mixture was washed with a saturated aqueous $NaHCO_3$ solution then with a saturated aqueous NaCl solution, and was dried over $Na_2SO_4$. After evaporation of the solvent, the residue was purified by column chromatography on silica gel (Hexane:EtOAc=2:1) to yield the corresponding ethyl ester (Compound 14) (0.224 g, 60%).

[Formula 27]

$^1$H-NMR (400 MHz, $CDCl_3$) δ 4.12 (2H, q, J=7.0 Hz, OC$\underline{H}_2CH_3$), 3.64 (2H, dd, J=6.6, 7.3 Hz, C$\underline{H}_2$OH), 2.29 (2H, t, J=7.7 Hz, C$\underline{H}_2CO_2$Et), 1.66-1.53 (5H, m, C$\underline{H}_2$CH$_2$OH, C$\underline{H}_2$CH$_2$CO$_2$Et, and O$\underline{H}$), 1.34 {6H, m, (C$\underline{H}_2$)$_3$}, 1.26 (3H, t, J=7.0 Hz, OCH$_2$C$\underline{H}_3$).

Subsequently, the target product was synthesized by the method described above (2% yield from Compound 14).

[Formula 28]

Mp 54-55° C.

$^1$H-NMR (400 MHz, $CDCl_3$) δ 12.66 (1H, s, Ar—O$\underline{H}$), 10.14 (1H, s, Ar—C$\underline{H}$O), 6.34 (1H, s, Ar—O$\underline{H}$), 4.11 (2H, q, J=7.3 Hz, CO$_2$C$\underline{H}_2$CH$_3$), 2.66 (2H, t, J=7.5 Hz, Ar—C$\underline{H}_2$), 2.61 (3H, s, Ar—C$\underline{H}_3$), 2.28 (2H, t, J=7.3 Hz, C$\underline{H}_2$CO$_2$Et) 1.65-1.49 (4H, m, ArCH$_2$C$\underline{H}_2$ & C$\underline{H}_2$CH$_2$CO$_2$Et), 1.34 {6H, br, (C$\underline{H}_2$)$_3$} 1.26 (3H, t, J=7.3 Hz, CO$_2$CH$_2$C$\underline{H}_2$).

IR (KBr) 3321, 2930, 2847, 1728, 1612, 1421, 1285, 1244, 1140, 783, 590 cm$^{-1}$.

HRMS (EI) Found: 356.1381. Calcd. for $C_{18}H_{25}ClO_5$: 356.1391.

8-(3-Chloro-5-formyl-2,6-dihydroxy-4-methylphenyl)octanoic acid (215-9-COOH)

Compound 215-11-COOEt was hydrolyzed by the method above to yield the target product (66% yield).

[Formula 29]

Mp. 149-150° C.

$^1$H-NMR (400 MHz, $CDCl_3$) δ 12.66 (1H, s, Ar—O$\underline{H}$), 10.14 (1H, s, Ar—C$\underline{H}$O), 6.33 (1H, br, Ar—O$\underline{H}$), 2.66 (2H, t, J=7.7 Hz, ArC$\underline{H}_2$), 2.61 (3H, s, Ar—C$\underline{H}_3$), 2.35 (2H, t, J=7.7 Hz, C$\underline{H}_2$COOH), 1.68-1.48 (4H, m, C$\underline{H}_2$CH$_2$COOH & ArCH$_2$C$\underline{H}_2$), 1.35 {6H, br, (C$\underline{H}_2$)$_3$}.

IR (KBr) 3350, 2930, 2850, 1710, 1620, 1420, 1370, 1280, 1245, 1135, 1120, 940, 775, 590 cm$^{-1}$.

HRMS (EI) Found: 328.1057. Calcd. for $C_{16}H_{21}ClO_5$: 328.1078.

9-Anthryl 8-(3-chloro-5-formyl-2,6-dihydroxy-4-methylphenyl)octanate (215-18-Anthra)

Compound 215-9-COOH was esterified by the method above to yield the target product (53% yield).

[Formula 30]

Mp. 150-151° C.

$^1$H-NMR (400 MHz, $CDCl_3$) δ 12.64 (1H, s, Ar—O$\underline{H}$), 10.13 (1H, s, Ar—C$\underline{H}$O), 8.51 (1H, s, Ar—$\underline{H}$), 8.33 (2H, d, J=8.8 Hz, Ar—$\underline{H}$), 8.03 (2H, d, J=8.4 Hz, Ar—H), 7.57 (2H, t, J=7.7 Hz, Ar—$\underline{H}$), 7.49 (2H, t, J=7.4 Hz, Ar—$\underline{H}$), 6.29 (1H, s, Ar—O$\underline{H}$), 6.15 (2H, s, CO$_2$C$\underline{H}_2$Ar), 2.62 (2H, t, J=7.3 Hz, Ar—C$\underline{H}_2$), 2.60 (3H, s, Ar—C$\underline{H}_3$), 2.32 {2H, t, J=7.5 Hz, C$\underline{H}_2$CO$_2$CH$_2$Ar}, 1.62-1.55 (2H, m, C$\underline{H}_2$), 1.50-1.42 (2H, m, C$\underline{H}_2$), 1.27 {6H, br, (C$\underline{H}_2$)$_3$}.

IR (KBr) 3356, 2916, 2853, 1717, 1634, 1468, 1421, 1391, 1373, 1296, 1252, 1182, 1126, 1094, 949, 889, 795, 733, 638, 590 cm$^{-1}$.

HRMS (EI) Found: 518.1859. Calcd. for $C_{31}H_{31}ClO_5$: 518.1860.

6. Compounds 217 and 224, and known natural products Colletorin B (Compound 216), Colletochlorin B, and LL-Z1272α (Compound 280-12)

Scheme 6.

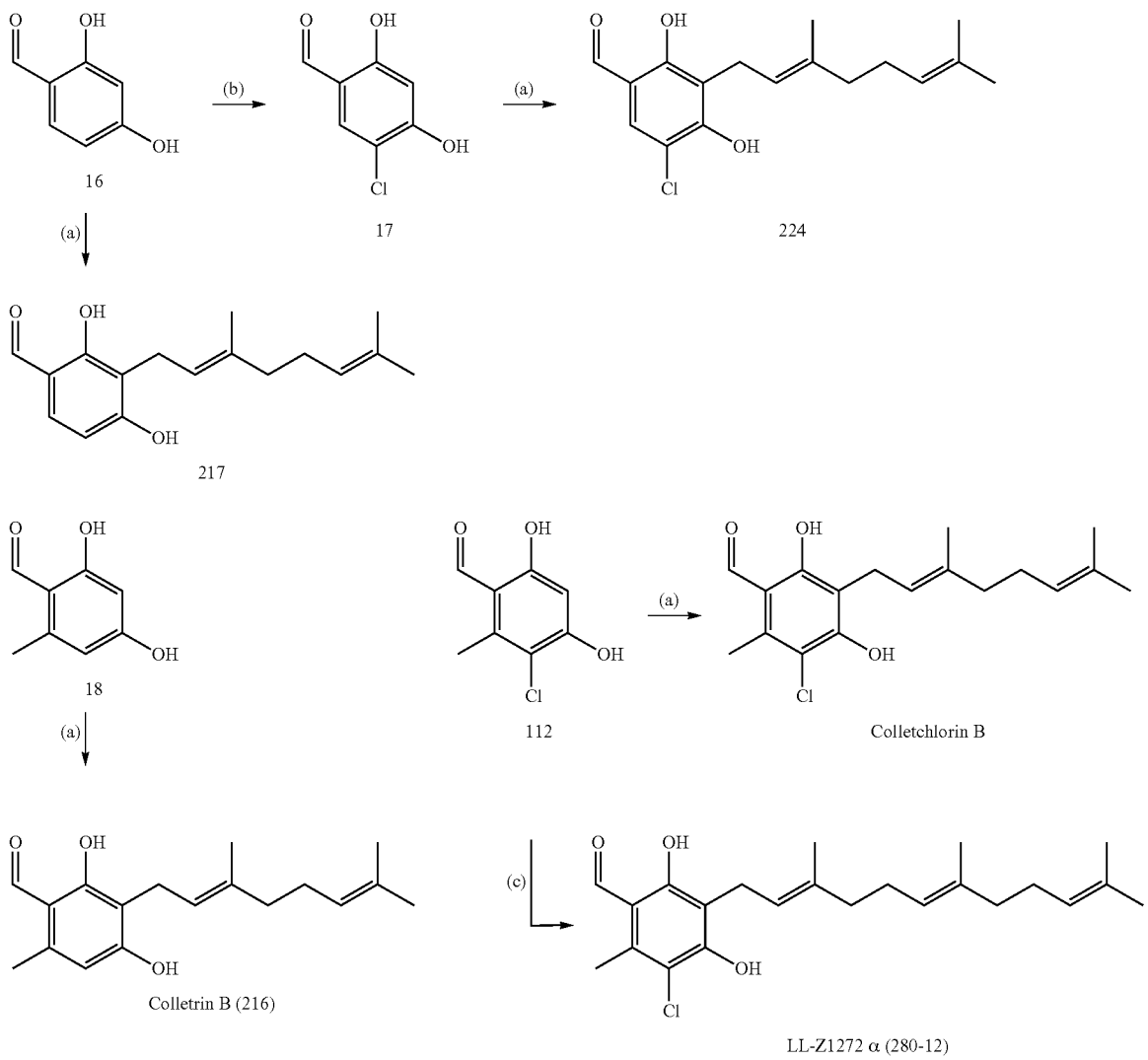

Reagents: (a) Geranyl bromide, KOH, CaCl$_2$, MeOH, (b) NCS, AcOH (c) Farnesyl bromide, KOH, CaCl$_2$, MeOH Typical Experimental Method for Introducing an Allylic Side Chain into the Aromatic Moiety A solution of the corresponding side chain bromide (1.2 eq.) in MeOH and CaCl$_2$.2H$_2$O (0.75 eq.) were added to a solution of a resorcinol derivative (1.0 eq.) in KOH (1.0 M in MeOH, 1.5 eq.) with cooling (at −40 to 0° C.), and the mixture was stirred (for 8 to 24 hours). The reaction solution was diluted with EtOAc, and was filtered through celite. The filtrate was then poured into a 0.1 M aqueous KOH solution, and the organic layer was separated. The aqueous layer was further extracted with EtOAc twice, and the combined organic layer was then washed with a saturated aqueous NaCl solution, and was dried over Na$_2$SO$_4$. After evaporation of the solvent, the residue was purified by column chromatography on silica gel or recrystallization to yield the corresponding alkylated compound. In addition, the aqueous layer was acidified with a 2 M aqueous HCl solution, and was extracted with EtOAc twice to recover the unreacted resorcinol derivative.

Typical Experimental Method for Chlorinating the Aromatic Moiety

NCS (1.1 eq.) was added to a solution of a resorcinol derivative (1.0 eq.) in acetic acid at room temperature, and the mixture was heated (at 80 to 100° C.) and stirred (for 14 to 24 hours). The reaction solution was allowed to warm to room temperature, and then poured into H$_2$O, and was extracted with EtOAc. Additionally the aqueous layer was extracted with EtOAc, and the combined organic layer was then washed with a saturated aqueous NaHCO$_3$ solution three times and a saturated aqueous NaCl solution once, and was dried over Na$_2$SO$_4$. After evaporation of the solvent, the residue was purified by column chromatography on silica gel or recrystallization to yield the corresponding chlorinated compound.

(E)-2,4-Dihydroxy-3-(3,7-dimethyl-2,6-octadienyl)benzaldehyde (Compound 217)

[Formula 32]

Mp 85° C.

$^1$H-NMR (400 MHz, CDCl$_3$) δ 11.79 (1H, s, Ar—OH), 9.69 (1H, s, Ar—CHO), 7.32 (1H, d, J=8.6 Hz, Ar—H), 6.48 (1H, d, J=8.6 Hz, Ar—H), 6.21 (1H, s, Ar—OH), 5.27 (1H, t, J=7.0 Hz, ArCH$_2$CH=C), 5.05 {1H, m, CH=C(CH$_3$)$_2$}, 3.45 (2H, d, J=7.0 Hz, ArCH$_2$), 2.16-2.05 (4H, m, CH$_2$CH$_2$), 1.82 (3H, s CH$_3$), 1.68 (3H, s CH$_3$).

IR (KBr) 3145, 2922, 1620, 1487, 1443, 1383, 1313, 1248, 1213, 1150, 1059, 787, 718, 642, 530 cm$^{-1}$.

Anal. Found: C, 74.41; H, 8.14%. Calcd for C$_{17}$H$_{22}$O$_3$: C, 74.42; H, 8.08%.

(E)-5-Chloro-2,4-dihydroxy-3-(3,7-dimethyl-2,6-octadienyl)benzaldehyde (Compound 224)

[Formula 33]

Mp 94-95° C.

$^1$H-NMR (500 MHz, CDCl$_3$) δ 11.53 (1H, s, Ar—OH), 9.67 (1H, s, Ar—CHO), 7.40 (1H, s, Ar—H), 6.33 (1H, s, Ar—OH), 5.23 {1H, t, J=7.3 Hz, ArCH$_2$CH=C), 5.05 {1H, t, J=7.0 Hz, CH=C(CH$_3$)$_2$}, 3.44 (2H, d, J=7.3 Hz, ArCH$_2$CH), 2.10-2.04 (2H, m, CH$_2$), 2.02-1.98 (2H, m, CH$_2$), 1.80 (3H, s, CH$_3$), 1.65 (3H, s, CH$_3$), 1.57 (3H, s, CH$_3$).

IR (KBr) 3231, 2916, 1628, 1576, 1464, 1425, 1387, 1331, 1275, 1240. 1202, 1157, 1088, 912, 876, 750, 715, 604 cm$^{-1}$.

HRMS (MI) Found: 308.1173. Calcd for C$_{17}$H$_{21}$O$_3$Cl: 308.1179.

(E)-2,4-Dihydroxy-3-(3,7-dimethyl-2,6-octadienyl)-6-methylbenzaldehyde (Compound 216, a known natural product Colletorin B)

[Formula 34]

Mp 120-121° C.

$^1$H-NMR (500 MHz, CDCl$_3$) δ 12.78 (1H, s, Ar—OH), 10.08 (1H, s, Ar—CHO), 6.21 (1H, s, Ar—H), 6.15 (1H, s, Ar—OH), 5.26 (1H, t, J=7.1 Hz, ArCH$_2$CH=C), 5.04 {1H, t, J=6.8 Hz, CH=C(CH$_3$)$_2$}, 3.41 (2H, d, J=7.1 Hz, ArCH$_2$CH), 2.50 (3H, s, Ar—CH$_3$), 2.14-2.05 (4H, m, CH$_2$CH$_2$), 1.81 (3H, s, CH$_3$), 1.68 (3H, s, CH$_3$), 1.59 (3H, s, CH$_3$).

IR (KBr) 3132, 2908, 1610, 1491, 1435, 1327, 1254, 1217, 1171, 1101, 1003, 829, 750, 644, 569 cm$^{-1}$.

(E)-3-Chloro-4,6-dihydroxy-5-(3,7-dimethyl-2,6-octadienyl)-2-methylbenzaldehyde (a known natural product Colletochlorin B)

[Formula 35]

44% yield $^1$H-NMR (500 MHz, CDCl$_3$) δ 12.70 (1H, s, Ar—OH), 10.14 (1H, s, Ar—CHO), 6.42 (1H, s, Ar—OH), 5.22 (1H, t, J=6.9 Hz, ArCH$_2$CH=C), 5.06 {1H, t, J=6.6 Hz, CH=C(CH$_3$)$_2$}, 3.40 (2H, d, J=6.9 Hz, ArCH$_2$CH), 2.61 (3H, s, Ar—CH$_3$), 2.08-2.03 (2H, m, CH$_2$), 2.01-1.96 (2H, m, CH$_2$), 1.78 (3H, s, CH$_3$), 1.64 (3H, s, CH$_3$), 1.56 (3H, s, CH$_3$).

(E,E)-3-Chloro-4,6-dihydroxy 5-(3,7,11-trimethyl-2,6,10-dodecathenyl)-2-methylbenzaldehyde (Compound 280-12, a known natural product LL-Z1272α)

[Formula 36]

Mp 72-73° C.

$^1$H-NMR (400 MHz, CDCl$_3$) δ 12.69 (1H, s, Ar—OH), 10.14 (1H, s, Ar—CHO), 6.41 (1H, s, Ar—OH), 5.22 (1H, t, J=7.3 Hz, ArCH$_2$CH=C), 5.06 (2H, t, J=7.0 Hz, 2×CH=C), 3.40 (2H, d, J=7.4 Hz, ArCH$_2$CH), 2.60 (3H, s, Ar—CH$_3$), 2.07 (2H, t, J=7.3 Hz, CH$_2$), 1.99 (4H, t, J=7.3 Hz, 2×CH$_2$), 1.92 (2H, t, J=7.5 Hz, CH$_2$), 1.79 (3H, s, CH$_3$), 1.64 (3H, s, CH$_3$), 1.58 (3H, s, CH$_3$), 1.56 (3H, s, CH$_3$).

IR (KBr) 3256, 2967, 2913, 2853, 1613, 1452, 1424, 1373, 1281, 1229, 1163, 1109, 961, 905, 876, 786, 713, 633, 592, 569 cm$^{-1}$.

Scheme 6-2.

[Formula 37]

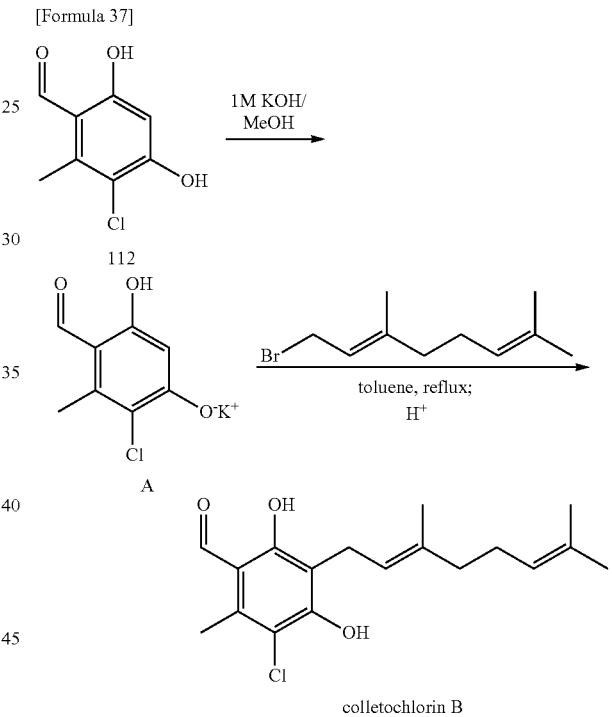

colletochlorin B

With the method described in the document (Tetrahedron, 1988, 44, 41-48) applied, a 1 M KOH/MeOH solution (5 mL) was added to Compound 112 (0.93 g, 5.0 mmol), and the mixture was stirred for 12 hours. The resulting precipitate was washed with MeOH (50 mL), and then filtered off, and dehydrated azeotropically with toluene to yield Compound A quantitatively. Subsequently, Compound A (72 mg, 0.32 mmol) was added to a solution of geranyl bromide (43 mg, 0.2 mmol) in toluene (2 mL), and the mixture was heated to reflux for 18 hours. Upon completion of the reaction, a 1 M aqueous HCl solution (5 mL) was added to the mixture. The organic layer was separated, and the aqueous layer was extracted with EtOAc. The combined organic layer was washed with saturated brine, and then dried over Na$_2$SO$_4$. After evaporation of EtOAc, the resulting product was purified by column chromatography on silica gel (Hexane/AcOEt=20/1) to yield the known natural product Colletochlorin B (44 mg, 68% yield).

7. Compounds 161, 157, 146, and 152

Scheme 7.

[Formula 38]

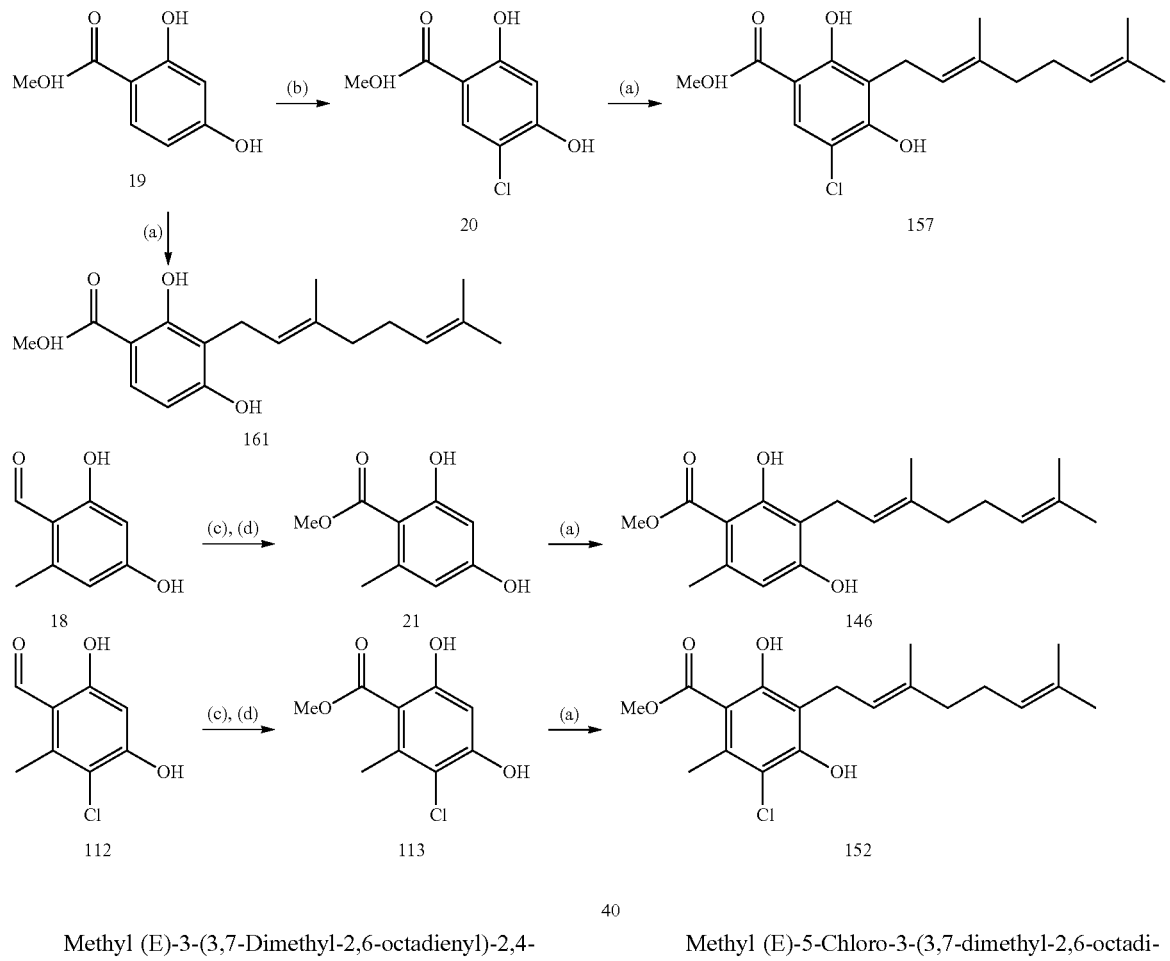

Methyl (E)-3-(3,7-Dimethyl-2,6-octadienyl)-2,4-dihydroxybenzoate (Compound 161)

[Formula 39]
Mp 62° C.
$^1$H-NMR (400 MHz, CDCl$_3$) δ 11.31 (1H, s, Ar—O$\underline{H}$), 7.63 (1H, d, J=8.6 Hz, Ar—$\underline{H}$), 6.37 (1H, d, J=8.6 Hz, Ar—$\underline{H}$), 5.93 (1H, s, Ar—O$\underline{H}$), 5.27 (1H, t, J=7.0 Hz, ArCH$_2$C$\underline{H}$=C), 5.05 {1H, m, C$\underline{H}$=C(CH$_3$)$_2$}, 3.91 (1H, s, CO$_2$C$\underline{H}_3$), 3.46 (2H, d, J=7.0 Hz, ArC$\underline{H}_2$), 2.14-2.04 (4H, m, C$\underline{H}_2$C$\underline{H}_2$), 1.82 (3H, s C$\underline{H}_3$), 1.67 (3H, s C$\underline{H}_3$), 1.59 (3H, s C$\underline{H}_3$).
IR (KBr) 3462, 2916, 1645, 1498, 1439, 1387, 1344, 1296, 1201, 1147, 1049, 783, 731, 631, 561 cm$^{-1}$.
Anal. Found: C, 70.74; H, 7.70%. Calcd for C$_{18}$H$_{24}$O$_4$: C, 71.03; H, 7.95%.

Methyl 5-chloro-2,4-dihydroxybenzoate (Compound 20)

[Formula 40]
39% yield.
$^1$H-NMR (400 MHz, CDCl$_3$) δ 10.84 (1H, s, Ar—O$\underline{H}$), 7.83 (1H, s, Ar—$\underline{H}$), 6.62 (1H, s, Ar—$\underline{H}$), 5.92 (1H, br, Ar—O$\underline{H}$), 3.93 (3H, s, CO$_2$C$\underline{H}_3$).

Methyl (E)-5-Chloro-3-(3,7-dimethyl-2,6-octadienyl)-2,4-dihydroxybenzoate (Compound 157)

[Formula 41]
Mp 71° C.
$^1$H-NMR (400 MHz, CDCl$_3$) δ 11.11 (1H, s, Ar—O$\underline{H}$), 7.72 (1H, s, Ar—$\underline{H}$), 6.10 (1H, s, Ar—OH), 5.23 (1H, t, J=7.2 Hz, ArCH$_2$C$\underline{H}$=C), 5.06 {1H, m, C$\underline{H}$=C(CH$_3$)$_2$}, 3.92 (3H, s, CO$_2$C$\underline{H}_3$), 3.43 (2H, d, J=7.2 Hz, Ar—C$\underline{H}_2$), 2.10-2.00 (2H, m, C$\underline{H}_2$), 2.01-1.95 (2H, m, C$\underline{H}_2$), 1.80 (3H, s, C$\underline{H}_3$), 1.65 (3H, s, C$\underline{H}_3$), 1.57 (3H, s, C$\underline{H}_3$).
HRMS (EI) Found: 338.1277. Calcd. for C$_{18}$H$_{23}$O$_4$Cl: M$^+$, 338.1285.

Methyl 2,4-dihydroxy-6-methylbenzoate (Compound 21)

Compound 21 was prepared from the corresponding benzaldehyde (Compound 18) though oxidation and esterification (52% from Compound 18). (For detailed experimental procedures, see the section of Compound 113.)

[Formula 42]
$^1$H NMR (400 MHz, CDCl$_3$) δ 11.78 (1H, s, Ar—O$\underline{H}$), 6.28 (1H, d, J=2.6 Hz, Ar—$\underline{H}$), 6.23 (1H, d, J=2.6 Hz, Ar—$\underline{H}$), 5.25 (1H, br, Ar—O$\underline{H}$), 3.93 (3H, s, CO$_2$C$\underline{H}_3$), 2.49 (3H, s, Ar—C$\underline{H}_3$).

Methyl (E)-3-(3,7-Dimethyl-2,6-octadienyl)-2,4-dihydroxy-6-methylbenzoate (Compound 146)

[Formula 43]
Mp 46-47° C.
$^1$H-NMR (400 MHz, CDCl$_3$) δ 12.12 (1H, s, Ar—OH), 6.23 (1H, s, Ar—H), 5.84 (1H, s, Ar—OH), 5.23 (1H, t, J=7.1 Hz, ArCH$_2$CH=C), 5.06 {1H, m, CH=C(CH$_3$)$_2$}, 3.92 (3H, s, CO$_2$CH$_3$), 3.43 (2H, d, J=7.0 Hz, Ar—CH$_2$), 2.15-2.04 (4H, m, CH$_2$CH$_2$), 1.81 (3H, s, CH$_3$), 1.67 (3H, s, CH$_3$), 1.59 (3H, s, CH$_3$).

IR (KBr) 3391, 2922, 2853, 1651, 1620, 1499, 1447, 1412, 1383, 1321, 1273, 1200, 1157, 1092, 1011, 984, 920, 878, 833, 812, 746, 718, 625, 604, 579 cm$^{-1}$.

Methyl 3-chloro-4,6-dihydroxy-2-methylbenzoate (Compound 113)

H$_2$O (5 ml) was added to a solution of Compound 112 (0.505 g, 2.706 mmol) in DMSO (10 ml), and the mixture was cooled to 0° C. Subsequently NaH$_2$PO$_4$.2H$_2$O (1.113 g, 7.134 mmol) and 5 minutes later NaClO$_2$ (79% purity 0.719 g, 6.28 mmol) each were added as a solid to the mixture. The mixture was allowed to warm to room temperature with stirring for 15 hours. The reaction solution was diluted with EtOAc. A saturated aqueous NaHCO$_3$ solution was then added to the diluted mixture, and the organic layer was separated. A saturated aqueous NaHCO$_3$ solution was again added to the organic layer, which was separated. The combined aqueous layer was acidified with a 2 M aqueous HCl solution, and then extracted with EtOAc three times. The combined organic layer was washed with a saturated aqueous NaCl solution, and was dried over Na$_2$SO$_4$. After evaporation of the solvent, the residue was loaded on column chromatography on silica gel (Hexane:EtOAc=2:1 to 1:2), followed by recrystallization from a mixed solvent in Hexane:EtOAc=3:1 to yield the corresponding carboxylic acid (0.410 g, 76%).

MeOH (0.085 ml, 2.1 mmol) was added to a solution of Ph$_3$P (0.560 g, 2.14 mmol) in THF (4 ml) under Ar at room temperature, and the mixture was cooled to 0° C. DEAD (40% in toluene, 0.5 ml, 2.1 mmol) was added to this cooled mixture, which was stirred for one hour. The carboxylic acid (0.339 g, 1.67 mmol) was then added as a solid to the mixture, which was stirred at 0° C. for 1.5 hours. H$_2$O and EtOAc were added to the reaction solution, which was stirred for 5 minutes. The organic layer was then separated, and the aqueous layer was extracted with EtOAc twice. The combined organic layer was washed with a saturated aqueous NaHCO$_3$ solution twice then with a saturated aqueous NaCl solution once, and was dried over Na$_2$SO$_4$. The solvent was evaporated, and the residue was loaded on column chromatography on silica gel (Hexane:EtOAc=2:1), and was recrystallized from a mixed solvent of Hexane:EtOAc=10:1 to yield the target product. The mother liquor was then concentrated, and then purified by column chromatography on silica gel (Hexane:EtOAc=7:1) to yield an additional crop of the target product (Combined yield, 0.286 g, 79%).

[Formula 44]
$^1$H-NMR (400 MHz, CDCl$_3$) δ 11.42 (1H, s, Ar—OH), 6.54 (1H, s, Ar—H), 6.06 (1H, s, Ar—OH), 3.95 (3H, s, CO$_2$CH$_3$), 2.63 (3H, s, Ar—H).

Methyl (E)-3-Chloro-4,6-dihydroxy-5-(3,7-dimethyl-2,6-octadienyl)-2-methylbenzoate (Compound 152)

[Formula 45]
$^1$H-NMR (500 MHz, CDCl$_3$) δ 11.65 (1H, s, Ar—OH), 6.20 (1H, s, Ar—OH), 5.23 (1H, t, J=7.1 Hz, ArCH$_2$CH=C), 5.06 {1H, t, J=6.9 Hz, CH=C(CH$_3$)$_2$}, 3.94 (3H, s, CO$_2$CH$_3$), 3.44 (2H, d, J=7.1 Hz, ArCH$_2$CH), 2.59 (3H, s, Ar—CH$_3$), 2.09-2.03 (2H, m, CH$_2$), 2.00-1.96 (2H, m, CH$_2$), 1.79 (3H, s, CH$_3$), 1.65 (3H, s, CH$_3$), 1.57 (3H, s, CH$_3$).

IR (KBr) 3508, 2935, 1655, 1603, 1464, 1439, 1415, 1383, 1313, 1292, 1258. 1202, 1196, 1161, 1088, 978, 799, 700 cm$^{-1}$.

HRMS (MI) Found: m/z, 338.1277. Calcd for C$_{18}$H$_{23}$O$_4$Cl: M$^+$, 338.1285.

8. Compounds 184, 177, 183, 173, and 282-12

Scheme 8.

[Formula 46]

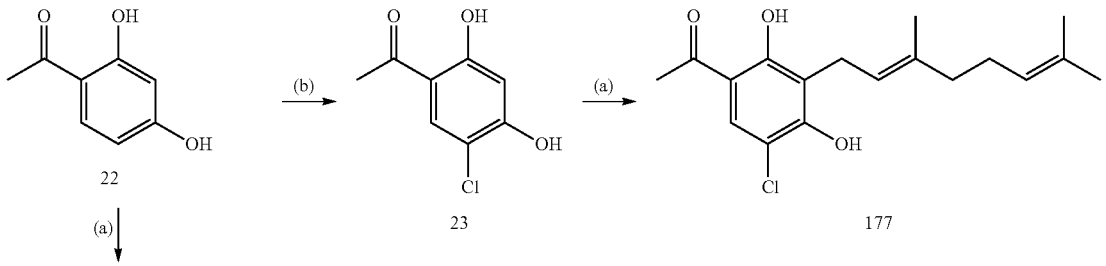

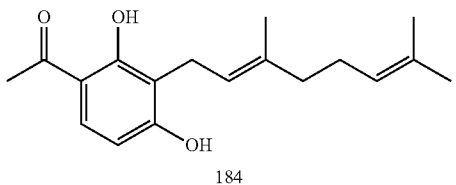

184

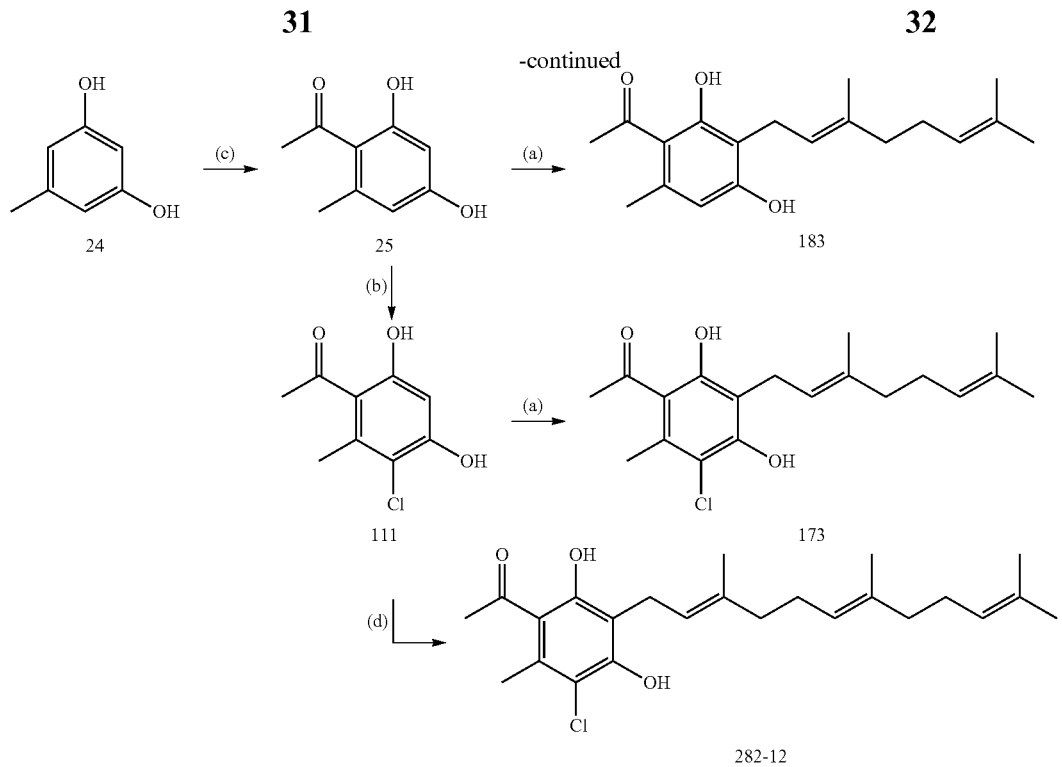

Reagents: (a) Geranyl bromide, KOH, CaCl₂ 2H₂O, MeOH (b) NCS, AcOH (c) AcOH,BF₃—Et₂O (d) Farnesyl bromide, KOH, CaCl₂ 2H₂O, MeOH.

(E)-3-(3,7-Dimethyl-2,6-octadienyl)-2,4-dihydroxyacetophenone (Compound 184)

[Formula 47]
Mp 134-135° C.
¹H-NMR (400 MHz, CDCl₃) δ 13.13 (1H, s, Ar—OH), 7.54 (1H, d, J=8.8 Hz, Ar—H), 6.39 (1H, d, J=8.8 Hz, Ar—H), 6.11 (1H, s, Ar—OH), 5.27 (1H, t, J=7.0 Hz, ArCH₂CH=C), 5.05 {1H, m, CH₂CH=C(CH₃)₂}, 3.46 (2H, d, J=7.0 Hz, ArCH₂), 2.57 (3H, s, CH₃C=O), 2.15-2.05 (4H, m, CH₂CH₂), 1.82 (3H, s, CH₃), 1.68 (3H, s, CH₃), 1.59 (3H, s, CH₃).
IR (KBr) 3161, 2964, 2916, 1624, 1589, 1499, 1456, 1379, 1317, 1279, 1223, 1163, 1055, 791, 721, 613, 567 cm⁻¹.

5-Chloro-2,4-dihydroxyacetophenone (Compound 23)

[Formula 48]
66% yield.
¹H-NMR (400 MHz, CDCl₃) δ 12.48 (1H, s, Ar—OH), 7.71 (1H, s, Ar—H), 6.60 (1H, s, Ar—H), 6.16 (1H, s, Ar—OH), 2.57 (3H, s, ArCOCH₃).

(E)-5-Chloro-3-(3,7-dimethyl-2,6-octadienyl)-2,4-dihydroxyacetophenone (Compound 177)

[Formula 49]
Mp 109-110° C.
¹H-NMR (500 MHz, CDCl₃) δ 12.83 (1H, s, Ar—OH), 7.60 (1H, s, Ar—H), 6.21 (1H, s, Ar—OH), 5.23 (1H, t, J=7.1 Hz, ArCH₂CH=C), 5.05 {1H, t, J=7.7 Hz, CH=C(CH₃)₂}, 3.43 (2H, d, J=7.1 Hz, ArCH₂), 2.56 (3H, s, CH₃C=O), 2.09-2.04 (2H, m, CH₂), 2.00-1.97 (2H, C H₂), 1.79 (3H, s, CH₃), 1.65 (3H, s, CH₃), 1.57 (3H, s, CH₃).

IR (KBr) 3271, 2921, 1628, 1469, 1425, 1373, 1300, 1240, 1209, 1163, 1062, 907, 787 cm⁻¹.

HRMS (MI) Found: m/z, 322.1353. Calcd for C₁₈H₂₃O₃Cl: M⁺, 322.1336.

3-Chloro-4,6-dihydroxy-2-methylacetophenone (Compound 111)

BF₃.OEt₂ (2.6 ml, 21 mmol) was added to a solution of orcinol (1.269 g, 10.22 mmol) in AcOH (4.0 ml, 70 mmol) at room temperature, and the mixture was heated and stirred at 80° C. for 18 hours. The reaction solution was allowed to warm to room temperature, and then diluted with EtOAc, and poured into H₂O. The organic layer was separated, and the aqueous layer was then extracted with EtOAc. The combined organic layer was washed with a saturated aqueous NaHCO₃ solution three times and a saturated aqueous NaCl solution once, and was dried over Na₂SO₄. Crude crystals formed after evaporation of the solvent was recrystallized from a mixed solvent of Hexane:EtOAc=1:3 to yield C-acetylated compound (Compound 25). The mother liquor was concentrated and loaded on column chromatography on silica gel (Hexane:EtOAc=3:2). Only the fractions containing Compound 25 were collected, and purified by recrystallization from the same solvent (Combined yield 65%).

[Formula 50]
¹H-NMR (400 MHz, CDCl₃) δ 13.44 (1H, s, Ar—OH), 6.26 (1H, d, J=2.6 Hz, Ar—H), 6.24 (1H, d, J=2.6 Hz Ar—H), 5.43 (1H, s, Ar—OH), 2.63 (3H, s, Ar—CH₃), 2.56 (3H, s, ArCOCH₃).

Compound 25 was chlorinated with NCS in AcOH to yield the target product (See the typical procedure, 65% yield).

[Formula 51]
¹H-NMR (400 MHz, CDCl₃) δ 12.37 (1H, s, Ar—OH), 6.52 (1H, s, Ar—H), 6.09 (1H, s, Ar—OH), 2.63 (6H, br, Ar—CH₃ & ArCOCH₃).

(E)-3-(3,7-Dimethyl-2,6-octadienyl)-2,4-dihydroxy-6-methylacetophenone (Compound 183)

[Formula 52]
Mp 102° C.
¹H-NMR (500 MHz, CDCl₃) δ 13.91 (1H, s, Ar—OH), 6.23 (1H, s, Ar—H), 5.98 (1H, s, Ar—OH), 5.27 (1H, t, J=6.8 Hz, ArCH₂CH=C), 5.05 {1H, t, J=6.2 Hz, CH=C(CH₃)₂}, 3.43 (2H, d, J=7.1 Hz, Ar—CH₂), 2.62 (3H, s, Ar—CH₃), 2.53 (3H, s, CH₃C=O), 2.14-2.04 (4H, m, CH₂CH₂), 1.84 (3H, s, CH₃), 1.68 (3H, s, CH₃), 1.59 (3H, s, CH₃).
IR (KBr) 3175, 2964, 2922, 1568, 1439, 1362, 1258, 1223, 1171, 1094, 1011, 986, 829, 791, 608, 575 cm⁻¹.
Anal. found: C, 75.22; H, 8.69%. Calcd. for C₁₉H₂₆O₃: C, 75.46; H, 8.67%.

(E)-3-Chloro-4,6-dihydroxy-5-(3,7-dimethyl-2,6-octadienyl)-2-methylacetophenone (Compound 173)

[Formula 53]
Mp 57-58° C.
¹H-NMR (400 MHz, CDCl₃) δ 12.56 (1H, s, Ar—OH), 6.25 (1H, s, Ar—OH), 5.23 (1H, t, J=7.1 Hz, ArCH₂CH=C), 5.06 {1H, t, J=6.7 Hz, CH=C(CH₃)₂}, 3.41 (2H, d, J=7.0 Hz, Ar—CH₂), 2.61 (3H, s, Ar—CH₃), 2.58 (3H, s, CH₃C=O), 2.10-2.03 (2H, m, CH₂), 2.01-1.95 (2H, m, CH₂), 1.79 (3H, s, CH₃), 1.65 (3H, s, CH₃), 1.57 (3H, s, CH₃).
IR (KBr) 3460, 2922, 2866, 1595, 1468, 1421, 1381, 1360, 1275, 1236, 1209, 1175, 1094, 993, 916, 826, 785, 638, 621, 600 cm⁻¹.
Anal. found: C, 67.80; H, 7.59%. Calcd. for C₁₉H₂₅ClO₃: C, 67.75; H, 7.48%. (Due to a small amount of the sample, Cl was unable to be determined.)

(E,E)-3-Chloro-4,6-dihydroxy 5-(3,7,11-trimethyl-2,6,10-dodecathenyl)-2-methylacetophenone (Compound 282-12)

[Formula 54]
Mp 92-93° C.
¹H-NMR (400 MHz, CDCl₃) δ 12.55 (1H, s, Ar—OH), 6.23 (1H, s, Ar—OH), 5.23 (1H, t, J=7.2 Hz, ArCH₂CH=C), 5.06 (2H, t, J=6.6 Hz, 2×CH=C), 3.41 (2H, d, J=7.4 Hz, Ar—CH₂), 2.60 (3H, s, Ar—CH₃), 2.58 (3H, s, Ar—COCH₃), 2.07 (2H, t, J=7.3 Hz, CH₂), 2.01-1.96 (4H, m, 2×CH₂), 1.93 (2H, t, J=7.5 Hz, CH₂), 1.79 (3H, s, CH₃), 1.67 (3H, s, CH₃), 1.58 (3H, s, CH₃), 1.57 (3H, s, CH₃).
IR (KBr) 3362, 2970, 2926, 2864, 1601, 1468, 1412, 1375, 1360, 1277, 1242, 1198, 1148, 1092, 1018, 991, 924, 887, 766, 617, 598, 556 cm⁻¹.
Anal. Found: C, 70.90; H, 8.16; Cl, 8.77%. Calcd for C₂₄H₃₃ClO₃: C, 71.18; H, 8.21; Cl, 8.75%.

9. Compounds 200-11-OPiv, 215-11-OPiv, 200-12-OPiv, 215-12-OPiv, 200-13-OPiv, 215-13-OPiv, 200-12-OCOⁱPr, 215-12-OCOⁱPr, 215-13-OCOⁱPr, 215-12-OCOEt, 200-13-OCOEt, and 215-13-OCOEt Scheme 9.
[Formula 55]

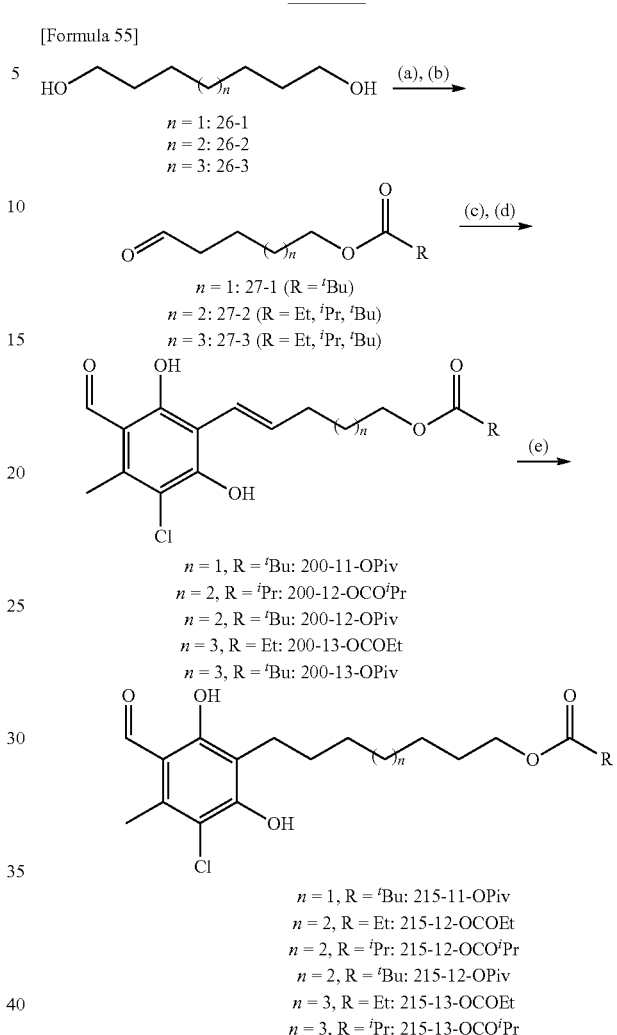

n = 1, R = ᵗBu: 200-11-OPiv
n = 2, R = ⁱPr: 200-12-OCOⁱPr
n = 2, R = ᵗBu: 200-12-OPiv
n = 3, R = Et: 200-13-OCOEt
n = 3, R = ᵗBu: 200-13-OPiv n = 1, R = ᵗBu: 215-11-OPiv
n = 2, R = Et: 215-12-OCOEt
n = 2, R = ⁱPr: 215-12-OCOⁱPr
n = 2, R = ᵗBu: 215-12-OPiv
n = 3, R = Et: 215-13-OCOEt
n = 3, R = ⁱPr: 215-13-OCOⁱPr
n = 3, R = ᵗBu: 215-13-OPiv

Reagents and conditions: (a) Coresponding acyl chloride, pyridine, CHCl₃ (b) Swern oxidation or TPAP, NMO, MS-4A, CHCl₃ (c) 112, KOH, CaCl₂ 2H₂O, MeOH (d) H₃PO₄, AcOH, reflux (e) H₂, Pd—C, EtOAc.

7-Oxoheptyl pivalate (Compound 27-1, R=tBu)

Piv-Cl (0.12 ml, 1.0 mmol) and pyridine (0.03 ml, 0.4 mmol) were added to a solution of 1,7-Heptanediol (Compound 26-1, 0.28 ml, 2.0 mmol) in CHCl₃ (2 ml) at 0° C., and the mixture was stirred for one day. H₂O was added to the reaction solution, the organic layer was then separated, and the aqueous layer was extracted with EtOAc. The combined organic layer was washed with a saturated aqueous NaCl solution, and was dried over Na₂SO₄. After evaporation of the solvent, the residue was purified by column chromatography on silica gel (Hexane:EtOAc=3:1) to yield 7-hydroxyheptyl pivalate (147 mg, 68%).

NMO (597 mg, 5.11 mmol), MS-4A (1.290 g), and TPAP (44 mg, 0.13 mmol) were added to a solution of 7-hydroxyheptyl pivalate (552 mg, 2.55 mmol) in CHCl₃ (5.1 ml) at room temperature, and the mixture was stirred for 3 hours. A saturated aqueous NH₄Cl solution was added to the reaction solution, and the organic layer was separated followed by extraction of the aqueous layer with CHCl$_3$. The combined organic layer was extracted with CHCl$_3$, and the extract was dried over Na$_2$SO$_4$. After evaporation of the solvent, the residue was purified by column chromatography on silica gel (Hexane:EtOAc=7:1) to yield the side-chain precursor compound 27-1 (217 mg, 40%).

[Formula 56]

$^1$H-NMR (500 MHz, CDCl$_3$) δ 9.77 (1H, t, J=1.7 Hz, CHO), 4.05 (2H, t, J=6.5 Hz, CH$_2$OPiv), 2.44 (2H, dt, J=1.8, 7.3 Hz, CH$_2$CHO), 1.68-1.61 (4H, m, CH$_2$CH$_2$CHO & CH$_2$CH$_2$OPiv), 1.39-1.35 (4H, m, CH$_2$CH$_2$), 1.19 {9H, s, C(CH$_3$)$_3$}.

IR (neat) 2941, 2860, 1728, 1477, 1286, 1159 cm$^{-1}$.

(E)-7-(3-Chloro-5-formyl-2,6-dihydroxy-4-methyl-phenyl)-6-heptenyl pivalate (Compound 200-11-OPiv)

Compound 112 (118 mg, 0.63 mmol) and CaCl$_2$.2H$_2$O (63 mg, 0.44 mmol) were added to a solution of the side-chain precursor 27-1 (162 mg, 0.75 mmol) in MeOH (1.3 ml), and the mixture was cooled to 0° C. KOH (1.0 M in MeOH, 0.9 ml, 0.9 mmol) was added to this cooled mixture, which was stirred at the same temperature for one day. A 1 M aqueous HCl solution was added to the reaction solution, followed by extraction with EtOAc three times. The combined organic layer was washed with a saturated aqueous NaCl solution, and was dried over Na$_2$SO$_4$. After evaporation of the solvent, the residue was subjected to column chromatography on silica gel (Hexane:EtOAc=10:1) to yield an aldol product (126 mg). This product was used directly in the next reaction without further purification.

The entire aldol product was dissolved in AcOH (1.8 ml). H$_3$PO$_4$ (85% purity, 0.2 ml) was added to the solution at room temperature, and refluxed for 2 hours. The reaction solution was allowed to warm to room temperature. A saturated aqueous NaCl solution was added to the reaction solution, followed by extraction with EtOAc twice. The combined organic layer was dried over Na$_2$SO$_4$. After evaporation of the solvent, the residue was purified by column chromatography on silica gel (Hexane:EtOAc=10:1) to yield the target product (104 mg, 43% for 2 steps).

[Formula 57]

Mp 57-58° C.

$^1$H-NMR (500 MHz, CDCl$_3$) δ 13.06 (1H, s, Ar—OH), 10.15 (1H, s, Ar—CHO), 6.66 (1H, dt, J=6.9, 16.3 Hz, ArCH=CH), 6.58 (1H, s, Ar—OH), 6.54 (1H, d, J=16.3 Hz, ArCH=CH), 4.06 (2H, t, J=6.7 Hz, CH$_2$OPiv), 2.62 (3H, s, Ar—CH$_3$), 2.28 (2H, q, J=7.1 Hz, CH=CHCH$_2$), 1.69-1.64 (2H, m, CH$_2$), 1.54-1.50 (2H, m, CH$_2$), 1.46-1.41 (2H, m, CH$_2$), 1.19 {9H, s, C(CH$_3$)$_3$}.

IR (neat) 3387, 2930, 2885, 1726, 1634, 1462, 1426, 1375, 1285, 1256, 1161, 1028, 980, 816, 754 cm$^{-1}$.

Anal. Found: C, 62.71; H, 7.05; Cl, 9.25%. Calcd for C$_{20}$H$_{27}$O$_5$Cl: C, 62.74; H, 7.11; Cl, 9.26%.

7-(3-Chloro-5-formyl-2,6-dihydroxy-4-methylphenyl)heptyl pivalate (Compound 215-11-OPiv)

A catalytic amount of Pd—C was added to a solution of 200-11-OPiv (70 mg, 0.18 mmol) in EtOH (2 ml) at 0° C., and the mixture was stirred under H$_2$ for 80 minutes. The reaction solution was filtered through silica gel. The filtrate was concentrated, and the residue was purified by PTLC (Hexane:EtOAc=3:1) to yield the target product (34 mg, 49%).

[Formula 58]

Mp 63-64° C.

$^1$H-NMR (500 MHz, CDCl$_3$) δ 12.65 (1H, s, Ar—OH), 10.14 (1H, s, Ar—CHO), 6.31 (1H, br, Ar—OH), 4.04 (2H, t, J=6.6 Hz, CH$_2$OPiv), 2.67 (2H, t, J=7.7 Hz, ArCH$_2$), 2.61 (3H, s, Ar—CH$_3$), 1.64-1.59 (2H, m, CH$_2$), 1.56-1.50 (2H, m, CH$_2$), 1.36 {6H, br, (CH$_2$)$_3$}, 1.19 {9H, s, C(CH$_3$)$_3$}.

IR (KBr) 3435, 2920, 2848, 1730, 1637, 1458, 1425, 1366, 1277, 1161, 1048, 848, 800, 760 cm$^{-1}$.

Anal. Found: C, 62.19; H, 7.57%. Calcd. for C$_{20}$H$_{29}$O$_5$Cl: C, 62.41; H, 7.59%.

Certain compounds having different chain lengths or terminal acyl groups were also synthesized in a similar manner.

(E)-8-(3-Chloro-5-formyl-2,6-dihydroxy-4-methyl-phenyl)-7-octenyl pivalate (Compound 200-12-OPiv)

[Formula 59]

Mp 57-58° C.

$^1$H-NMR (400 MHz, CDCl$_3$) δ 13.07 (1H, s, Ar—OH), 10.15 (1H, s, Ar—CHO), 6.51-6.69 (2H, m, CH=CH), 4.06 (2H, t, J=7.0 Hz, CH$_2$OPiv), 2.62 (3H, s, Ar—CH$_3$), 2.27 (2H, q, J=6.6 Hz, CH=CHCH$_2$), 1.64-1.52 (4H, m, 2×CH$_2$), 1.39 (4H, br, 2×CH$_2$), 1.20 {9H, s, C(CH$_3$)$_3$}.

IR (KBr) 3244, 2937, 1718, 1616, 1414, 1288, 1232, 978, 795, 596 cm$^{-1}$.

8-(3-Chloro-5-formyl-2,6-dihydroxy-4-methylphenyl)octyl pivalate (Compound 215-12-OPiv)

[Formula 60]

Mp 70-71° C.

$^1$H-NMR (400 MHz, CDCl$_3$) δ 12.66 (1H, s, Ar—OH), 10.15 (1H, s, Ar—CHO), 6.34 (1H, br, Ar—OH), 4.04 (2H, t, J=6.4 Hz, CH$_2$OPiv), 2.66 (2H, t, J=7.2 Hz, ArCH$_2$), 2.61 (3H, s, Ar—CH$_3$), 1.65-1.58 (2H, m, CH$_2$), 1.55-1.48 (2H, m, CH$_2$), 1.35 {8H, m, (CH$_2$)$_4$}, 1.20 {9H, s, C(CH$_3$)$_3$}.

IR (KBr) 3350, 2930, 2858, 1724, 1612, 1421, 1362, 1248, 1159, 800, 714, 590 cm$^{-1}$.

HRMS (EI) Found: 398.1890. Calcd. for C$_{21}$H$_{31}$ClO$_5$: 398.1860.

(E)-9-(3-Chloro-5-formyl-2,6-dihydroxy-4-methyl-phenyl)-8-nonenyl pivalate (Compound 200-13-OPiv)

[Formula 61]

Mp 69-70° C.

$^1$H-NMR (400 MHz, CDCl$_3$) δ 13.06 (1H, s, Ar—OH), 10.15 (1H, s, ArCHO), 6.65 (1H, dt, J=6.8, 16.0 Hz, ArCH=CH$_2$), 6.61 (1H, br, Ar—OH), 6.52 (1H, d, J=16.0 Hz, ArCH=CH$_2$), 4.05 (2H, t, J=6.8 Hz, CH$_2$OPiv), 2.62 (3H, s, Ar—CH$_3$), 2.27 (2H, q, J=6.8 Hz, CH=CH$_2$CH$_2$), 1.67-1.58 (2H, m, CH$_2$), 1.53-1.45 (2H, m, CH$_2$), 1.36 {6H, br, (CH$_2$)$_3$}, 1.20 {9H, s, C(CH$_3$)$_3$}.

IR (KBr) 2943, 2860, 1724, 1628, 1460, 1391, 1377, 1286, 1161, 1028, 976, 941, 885, 808, 716, 590 cm$^{-1}$.

HRMS (EI) Found: 410.1849. Calcd. for C$_{22}$H$_{31}$ClO$_5$: 410.1860.

9-(3-Chloro-5-formyl-2,6-dihydroxy-4-methylphenyl)nonyl pivalate (Compound 215-13-OPiv)

[Formula 62]
Mp 62° C.
$^1$H-NMR (400 MHz, CDCl$_3$) δ 12.66 (1H, s, Ar—O$\underline{H}$), 10.14 (1H, s, Ar—C$\underline{H}$O), 6.33 (1H, br, Ar—O$\underline{H}$), 4.04 (2H, t, J=6.6 Hz, C$\underline{H}_2$OPiv), 2.66 (2H, t, J=7.9 Hz, ArC$\underline{H}_2$), 2.61 (3H, s, Ar—C$\underline{H}_3$), 1.64-1.57 (2H, m, C$\underline{H}_2$), 1.54-1.48 (2H, m, C$\underline{H}_2$), 1.30 {10H, br, (C$\underline{H}_2$)$_5$}, 1.19 {9H, s, C(C$\underline{H}_3$)$_3$}.
IR (KBr) 3377, 2916, 2853, 1732, 1614, 1481, 1421, 1366, 1283, 1240, 1145, 1126, 1032, 843, 785, 621, 586 cm$^{-1}$.
HRMS (EI) Found: 412.2043. Calcd. for C$_{22}$H$_{33}$ClO$_5$: 412.2017.

(E)-8-(3-Chloro-5-formyl-2,6-dihydroxy-4-methylphenyl)-7-octenyl isobutylate (Compound 200-12-OCO$^i$Pr)

[Formula 63]
Mp 73° C.
$^1$H-NMR (400 MHz, CDCl$_3$) δ 13.06 (1H, s, Ar—O$\underline{H}$), 10.15 (1H, s, Ar—C$\underline{H}$O), 6.64 (1H, dt, J=6.8, 16.1 Hz, ArCH=C$\underline{H}_2$), 6.60 (1H, br, Ar—O$\underline{H}$), 6.53 (1H, d, J=16.1 Hz, ArC$\underline{H}$=CH$_2$), 4.06 {2H, t, J=6.8 Hz, C$\underline{H}_2$OC(O)$^i$Pr}, 2.62 (3H, s, Ar—C$\underline{H}_3$), 2.58-2.51 {1H, m, C$\underline{H}$(CH$_3$)$_2$}, 2.27 (2H, q, J=6.8 Hz, CH=CH$_2$C$\underline{H}_2$), 1.68-1.60 (2H, m, C$\underline{H}_2$), 1.53-1.47 (2H, m, C$\underline{H}_2$), 1.42-1.35 {4H, m, (C$\underline{H}_2$)$_2$}, 1.16 {6H, d, J=7.0 Hz, CH(C$\underline{H}_3$)$_2$}.
IR (KBr) 3206, 2972, 2928, 2855, 1732, 1618, 1456, 1414, 1283, 1204, 1163, 1132, 978, 793, 592 cm$^{-1}$.
Anal. Found: C, 63.03; H, 7.16; Cl, 9.22%. Calcd. for C$_{20}$H$_{27}$ClO$_5$: C, 62.74; H, 7.11; Cl, 9.26%.

8-(3-Chloro-5-formyl-2,6-dihydroxy-4-methylphenyl)octyl isobutylate (Compound 215-12-OCO$^i$Pr)

[Formula 64]
Mp 65° C.
$^1$H-NMR (400 MHz, CDCl$_3$) δ 12.65 (1H, s, Ar—O$\underline{H}$), 10.14 (1H, s, Ar—C$\underline{H}$O), 6.33 (1H, br, Ar—O$\underline{H}$), 4.05 {2H, t, J=6.8 Hz, C$\underline{H}_2$OC(O)$^i$Pr}, 2.66 (2H, t, J=7.7 Hz, Ar—C$\underline{H}_2$), 2.60 (3H, s, Ar—C$\underline{H}_3$), 2.57-2.50 {1H, m, C$\underline{H}$(CH$_3$)$_2$}, 1.65-1.58 (2H, m, C$\underline{H}_2$), 1.54-1.48 (2H, m, C$\underline{H}_2$), 1.33 {8H, br, (C$\underline{H}_2$)$_4$}, 1.16 {6H, d, J=7.0 Hz, CH(C$\underline{H}_3$)$_2$}.
IR (KBr) 3335, 2930, 2853, 2363, 1728, 1628, 1464, 1421, 1240, 1136, 791, 586.
Anal. Found: C, 62.59; H, 7.62; Cl, 9.01%. Calcd. for C$_{20}$H$_{29}$ClO$_5$: C, 62.41; H, 7.59; Cl, 9.21%.

9-(3-Chloro-5-formyl-2,6-dihydroxy-4-methylphenyl)nonyl isobutylate (Compound 215-13-OCO$^i$Pr)

[Formula 65]
Mp 55-56° C.
$^1$H-NMR (400 MHz, CDCl$_3$) δ 12.66 (1H, s, Ar—O$\underline{H}$), 10.14 (1H, s, Ar—C$\underline{H}$O), 6.33 (1H, s, Ar—OH), 4.05 {2H, t, J=6.8 Hz, CH$_2$OC(O)$^i$Pr}, 2.61 (3H, s, Ar—C$\underline{H}_3$), 2.58-2.51 {1H, m, C$\underline{H}$(C$\underline{H}_3$)$_2$}, 1.65-1.58 (2H, m, C$\underline{H}_2$), 1.54-1.48 (2H, m, C$\underline{H}_2$), 1.33 {10H, br, (C$\underline{H}_2$)$_5$}, 1.16 {6H, d, J=7.0 Hz, CH(C$\underline{H}_3$)$_2$}.
IR (KBr) 3364, 2964, 2930, 2860, 1736, 1620, 1470, 1418, 1373, 1283, 1240, 1198, 1153, 1124, 787, 592 cm$^{-1}$.
Anal. Found: C, 63.41; H, 7.82; Cl, 8.71%. Calcd for C$_{21}$H$_{31}$ClO$_5$: C, 63.23; H, 7.83; Cl, 8.89%.

8-(3-Chloro-5-formyl-2,6-dihydroxy-4-methylphenyl)octyl propionate (Compound 215-12-OCOEt)

[Formula 66]
Mp 63-64° C.
$^1$H-NMR (400 MHz, CDCl$_3$) δ 12.65 (1H, s, Ar—O$\underline{H}$), 10.15 (1H, s, Ar—C$\underline{H}$O), 6.33 (1H, br, Ar—O$\underline{H}$), 4.06 {2H, t, J=6.4 Hz, C$\underline{H}_2$OC(O)Et}, 2.67 (2H, t, J=7.7 Hz, Ar—C$\underline{H}_2$), 2.61 (3H, s, Ar—C$\underline{H}_3$), 2.32 {2H, q, J=7.5 Hz, C(O)CH$_2$CH$_3$}, 1.67-1.48 (4H, m, 2×C$\underline{H}_2$), 1.33 {8H, br, (C$\underline{H}_2$)$_4$}, 1.14 {3H, t, J=7.5 Hz, C(O)CH$_2$C$\underline{H}_3$}.
IR (KBr) 3335, 2935, 2839, 1729, 1632, 1470, 1418, 1369, 1286, 1261, 1213, 1128, 1088, 812, 627, 590 cm$^{-1}$.
HRMS (EI) Found: 370.1546. Calcd. for C$_{19}$H$_{27}$ClO$_5$: 370.1547.

(E)-9-(3-Chloro-5-formyl-2,6-dihydroxy-4-methylphenyl)-8-nonenyl propionate (Compound 200-13-OCOEt)

[Formula 67]
Mp 72-73° C.
$^1$H-NMR (400 MHz, CDCl$_3$) δ 13.05 (1H, s, Ar—O$\underline{H}$), 10.15 (1H, s, Ar—C$\underline{H}$O), 6.65 (1H, dt, J=6.8, 16.1 Hz, ArCH=C$\underline{H}_2$), 6.60 (1H, br, Ar—O$\underline{H}$), 6.53 (1H, d, J=16.1 Hz, ArC$\underline{H}$=CH$_2$), 4.07 {2H, t, J=6.8 Hz, C$\underline{H}_2$OC(O)Et}, 2.62 (3H, s, Ar—C$\underline{H}_3$), 2.32 {2H, q, J=7.5 Hz, C(O)CH$_2$CH$_3$}, 2.27 (2H, q, J=6.8 Hz, CH=CH$_2$C$\underline{H}_2$), 1.66-1.58 (2H, m, C$\underline{H}_2$), 1.52-1.46 (2H, m, C$\underline{H}_2$), 1.36 {6H, br, (C$\underline{H}_2$)$_3$}, 1.14 (3H, t, J=7.5 Hz, CH$_2$C$\underline{H}_3$).
IR (KBr) 3385, 2916, 2847, 1728, 1624, 1582, 1456, 1425, 1352, 1261, 1194, 1132, 1111, 1084, 964, 829, 791, 683, 592 cm$^{-1}$.

9-(3-Chloro-5-formyl-2,6-dihydroxy-4-methylphenyl)nonyl propionate (Compound 215-13-OCOEt)

[Formula 68]
Mp 69-70° C.
$^1$H-NMR (400 MHz, CDCl$_3$) δ 12.66 (1H, s, Ar—O$\underline{H}$), 10.14 (1H, s, Ar—C$\underline{H}$O), 6.33 (1H, s, Ar—O$\underline{H}$), 4.06 {2H, t, J=6.9 Hz, C$\underline{H}_2$OC(O)Et}, 2.66 (2H, t, J=7.7 Hz, Ar—C$\underline{H}_2$), 2.61 (3H, s, Ar—C$\underline{H}_3$), 2.31 {2H, q, J=7.7 Hz, C(O)C$\underline{H}_2$CH$_3$}, 1.67-1.48 (4H, m, 2×C$\underline{H}_2$), 1.30 {10H, br, (C$\underline{H}_2$)$_5$}, 1.14 {3H, t, J=7.7 Hz, C(O)CH$_2$C$\underline{H}_3$}.
IR (KBr) 3352, 2926, 2853, 1742, 1614, 1369, 1285, 1238, 1184, 1124, 1082, 783, 627, 586 cm$^{-1}$.
Anal. Found: C, 62.40; H, 7.45; Cl, 9.09%. Calcd for C$_{20}$H$_{29}$ClO$_5$: C, 62.41; H, 7.59; Cl, 9.21%.

10. Compounds 143-12-OPiv, 178-11-OPiv, 172-11-OPiv, and 193-11-Opiv

Scheme 10.

[Formula 69]

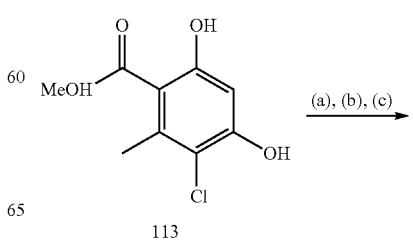

113

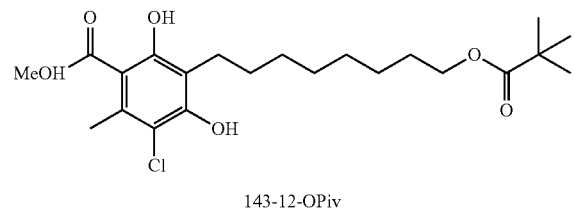

143-12-OPiv

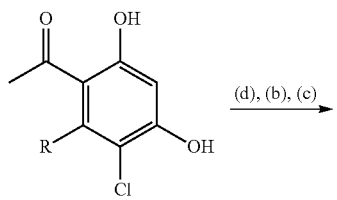

R = H: 23
R = Me: 111

(d), (b), (c) →

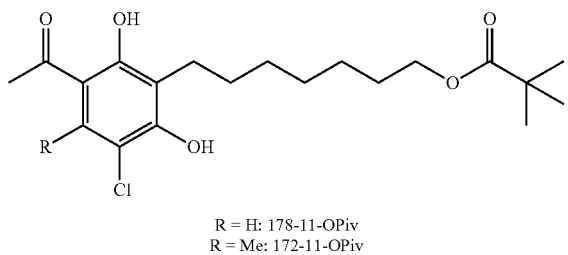

R = H: 178-11-OPiv
R = Me: 172-11-OPiv

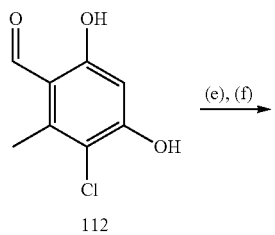

112

(e), (f) →

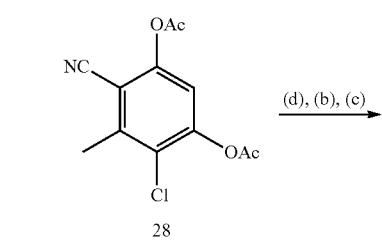

28

(d), (b), (c) →

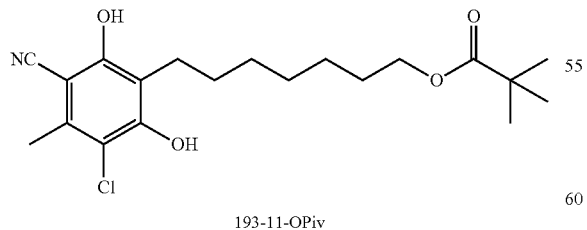

193-11-OPiv

Reagents and conditions: (a) 27-2 (R = $^t$Bu), KOH, CaCl$_2$ 2H$_2$O, MeOH (b) H$_3$PO$_4$, AcOH, reflux (c) H$_2$, Pd—C, EtOAc (d) 27-1 (R = $^t$Bu), KOH, CaCl$_2$ 2H$_2$O, MeOH (e) NH$_2$OH·HCl, AcONa, AcOH (f) Ac$_2$O, reflux 8-(3-Chloro-2,6-dihydroxy-5-methoxycarbonyl-4-methylphenyl)octyl pivalate (Compound 143-12-OPiv)

Compound 143-12-OPiv was synthesized from the aromatic ring compound 113 in the ester form as a raw material as in Scheme 9 described above.
[Formula 70]
$^1$H-NMR (400 MHz, CDCl$_3$) δ 11.63 (1H, s, Ar—OH), 6.14 (1H, br, Ar—OH), 4.04 (2H, t, J=6.6 Hz, CH$_2$OPiv), 3.94 (3H, s, CO$_2$CH$_3$), 2.68 (2H, t, J=7.7 Hz, ArCH$_2$), 2.59 (3H, s, Ar—CH$_3$), 1.65-1.49 (4H, m, ArCH$_2$CH$_2$ & CH$_2$CH$_2$OPiv), 1.33 (8H, br, (CH$_2$)$_4$), 1.19 (9H, s, C(CH$_3$)$_3$).

7-(3-Acetyl-5-chloro-2,6-dihydroxyphenyl)heptyl pivalate (Compound 178-11-OFPiv)

Compound 178-11-OPiv was synthesized from the aromatic ring compound 23 in the ketone form as a raw material as in Scheme 9 described above.
[Formula 71]
Mp 48° C.
$^1$H-NMR (400 MHz, CDCl$_3$) δ 12.78 (1H, s, Ar—OH), 7.59 (1H, s, Ar—H), 6.12 (1H, br, Ar—OH), 4.04 (2H, t, J=6.6 Hz, CH$_2$OPiv), 2.69 (2H, t, J=7.5 Hz, Ar—CH$_2$), 2.55 (3H, s, CH$_3$C=O), 1.66-1.58 (2H, m, CH$_2$), 1.56-1.48 (2H, m, CH$_2$), 1.36 {6H, br, (CH$_2$)$_3$}, 1.19 {9H, s, C(CH$_3$)$_3$}.
IR (KBr) 3300, 2930, 2852, 1728, 1616, 1474, 1418, 1373, 1339, 1286, 1150, 1119, 1045, 968, 872, 787, 623, 586 cm$^{-1}$.
HRMS (EI) Found: 384.1705. Calcd. for C$_{20}$H$_{29}$ClO$_5$: 384.1704.

7-(3-Acetyl-5-chloro-2,6-dihydroxy-4-methylphenyl)heptyl pivalate (Compound 172-11-OPiv)

Compound 172-11-OPiv was synthesized from the aromatic ring compound 111 in the ketone form as a raw material as in Scheme 9 described above.
[Formula 72]
$^1$H-NMR (400 MHz, CDCl$_3$) δ 12.64 (1H, s, Ar—OH), 6.15 (1H, s, Ar—OH), 4.04 (2H, t, J=6.6 Hz, CH$_2$OPiv), 2.67 (2H, t, J=7.7 Hz, Ar—CH$_2$), 2.61 (3H, s, Ar—CH$_3$), 2.59 (3H, s, CH$_3$C=O), 1.64-1.57 (2H, m, CH$_2$), 1.55-1.48 (2H, m, CH$_2$), 1.36 (6H, br, (CH$_2$)$_3$), 1.19 (9H, s, C(CH$_3$)$_3$).
IR (KBr) 3412, 2943, 2866, 1720, 1607, 1464, 1416, 1366, 1273, 1161, 1115, 1074, 1036, 984, 860, 770, 596 cm$^{-1}$.
HRMS (EI) Found: 398.1870. Calcd. for C$_{21}$H$_{31}$ClO$_5$: 398.1860.

4-Chloro-6-cyano-5-methylresorcinol diacetate (Compound 28)

NH$_2$OH·HCl (0.589 g, 8.47 mmol) and Compound 112 (1.308 g, 7.01 mmol) were added to a solution of AcONa (0.648 g, 7.90 mmol) in AcOH (10 ml) at room temperature, and the mixture was stirred for 7 hours. EtOAc and H$_2$O were added to the reaction solution, and the organic layer was separated followed by extraction of the aqueous layer with EtOAc. The combined organic layer was washed with a saturated aqueous NaHCO$_3$ solution then with a saturated aqueous NaCl solution, and was dried over Na$_2$SO$_4$. The corresponding oxime (1.400 g) obtained by evaporating the solvent was used directly in the next reaction without further purification.

The entire oxime was dissolved in Ac$_2$O (30 ml), and the solution was stirred at 130° C. for 12 hours. The reaction solution was allowed to warm to room temperature, and Et$_2$O and H$_2$O were then added to the solution. The organic layer was separated and the aqueous layer was extracted with Et$_2$O. The combined organic layer was washed with a saturated aqueous NaHCO$_3$ solution twice then with a saturated aqueous NaCl solution once, and was dried over Na$_2$SO$_4$. After evaporation of the solvent, precipitated crude crystals were recrystallized from a mixed solvent of MeOH and H$_2$O (4:1) to yield aromatic ring compound 28 as a raw material. Also, the mother liquor was concentrated, and the residue was purified by column chromatography on silica gel (Hexane:EtOAc=2:1) to yield Compound 28 (in total 1.388 g, 74% yield for 2 steps).

[Formula 73]

$^1$H-NMR (400 MHz, CDCl$_3$) δ 7.06 (1H, s, Ar—H), 2.64 (3H, s, Ar—CH$_3$), 2.39 (3H, s, OCOCH$_3$), 2.37 (3H, s, OCOCH$_3$).

$^{13}$C-NMR (100 MHz, CDCl$_3$) 167.9, 167.5, 151.2, 150.7, 142.7, 125.7, 116.4, 113.6, 106.8, 20.8, 20.6, 19.4.

7-(3-Chloro-5-cyano-2,6-dihydroxy-4-methylphenyl)heptyl pivalate (Compound 193-11-OPiv)

Compound 193-11-OPiv was synthesized from the aromatic ring compound 28 in the nitrile form as a raw material as in Scheme 9 described above.

[Formula 74]

Mp 67-68° C.

$^1$H-NMR (400 MHz, CDCl$_3$) δ 6.21 (1H, br, Ar—OH), 6.17 (1H, s, Ar—OH), 4.05 (2H, t, J=6.6 Hz, CH$_2$OPiv), 2.66 (2H, t, J=7.7 Hz, ArCH$_2$), 2.51 (3H, s, Ar—CH$_3$), 1.66-1.58 (2H, m, CH$_2$), 1.56-1.48 (2H, m, CH$_2$), 1.35 {6H, br, (CH$_2$)$_3$}, 1.20 {9H, s, C(CH$_3$)$_3$}.

$^{13}$C-NMR (100 MHz, CDCl$_3$) 178.8, 156.3, 154.1, 137.2, 115.8, 115.3, 113.4, 93.9, 64.4, 38.8, 29.3, 28.9, 28.6, 28.3, 27.2, 25.8, 23.7, 18.9.

IR (KBr) 3383, 2926, 2853, 2232, 1715, 1593, 1468, 1416, 1366, 1325, 1286, 1244, 1171, 1119, 1057, 1036, 980, 847, 799, 690, 627, 590 cm$^{-1}$.

11. Compounds 215-11-OAc and 215-9-OH

Scheme 11.

[Formula 75]

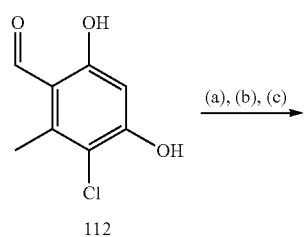

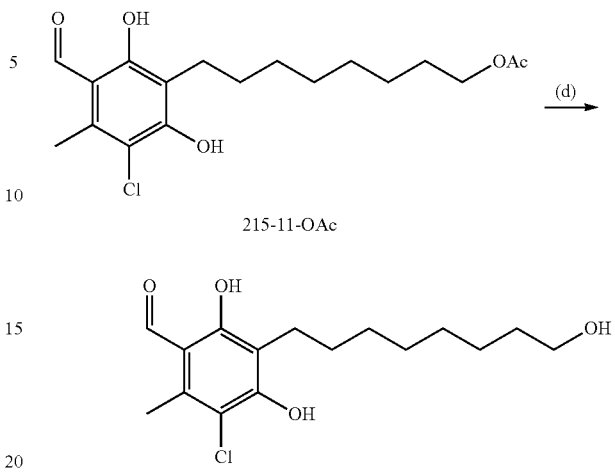

Reagents and conditions: (a) 8, KOH, CaCl$_2$ 2H$_2$O, MeOH (b) H$_3$PO$_4$, AcOH, reflux (c) H$_2$, Pd—C, EtOAc (d) NaOH, Acetone/H$_2$O 8-(3-Chloro-5-formyl-2,6-dihydroxy-4-methylphenyl)octyl acetate (Compound 215-11-OAc)

The aldol product prepared from aromatic ring compound 112 as a raw material and aldehyde 8 by the method described above was refluxed in acetic acid in the presence of phosphoric acid, causing cleavage of the THP group followed by acetylation to yield the target product.

[Formula 76]

Mp. 68° C.

$^1$H-NMR (400 MHz, CDCl$_3$) δ 12.65 (1H, s, Ar—OH), 10.14 (1H, s, Ar—CHO), 6.33 (1H, br, Ar—OH), 4.05 (2H, t, J=6.8 Hz, CH$_2$OPiv), 2.66 (2H, t, J=7.7 Hz, ArCH$_2$), 2.61 (3H, s, Ar—CH$_3$), 2.04 (3H, s, OC(O)CH$_3$), 1.65-1.50 (4H, m, 2×CH$_2$), 1.34 (8H, br, (CH$_2$)$_4$).

IR (KBr) 3321, 2930, 2853, 1728, 1624, 1464, 1258, 1128, 1051, 797, 596 cm$^{-1}$.

HRMS (EI) Found: 356.1393. Calcd. for C$_{18}$H$_{25}$ClO$_5$: 356.1391.

5-Chloro-2,4-dihydroxy-3-(8-hydroroxyoctyl)-6-methylbenzaldehyde (Compound 215-9-OH)

Compound 215-11-OAc was hydrolyzed by the method above to yield the target product.

[Formula 77]

Mp 129-130° C.

$^1$H-NMR (400 MHz, CDCl$_3$) δ 12.66 (1H, s, Ar—OH), 10.14 (1H, s, Ar—CHO), 6.33 (1H, s, Ar—OH), 3.64 (2H, t, J=6.2 Hz, CH$_2$OH), 2.67 (2H, t, J=7.3 Hz, Ar—CH$_2$), 2.61 (3H, s, Ar—CH$_3$), 1.64-1.47 (4H, m, CH$_2$CH$_2$OH & ArCH$_2$CH$_2$), 1.34 (8H, br, (CH$_2$)$_4$). IR (KBr) 3539, 2924, 1627, 1421, 1296, 1257, 1132, 1016, 812 cm$^{-1}$.

HRMS (EI) Found: 314.1265. Calcd. for C$_{16}$H$_{23}$ClO$_4$: 314.1285.

12. Compounds Ascofuranone, 214 (acetyl AF), 209 (demethyl AF), 249, and 250

Scheme 12.

[Formula 78]

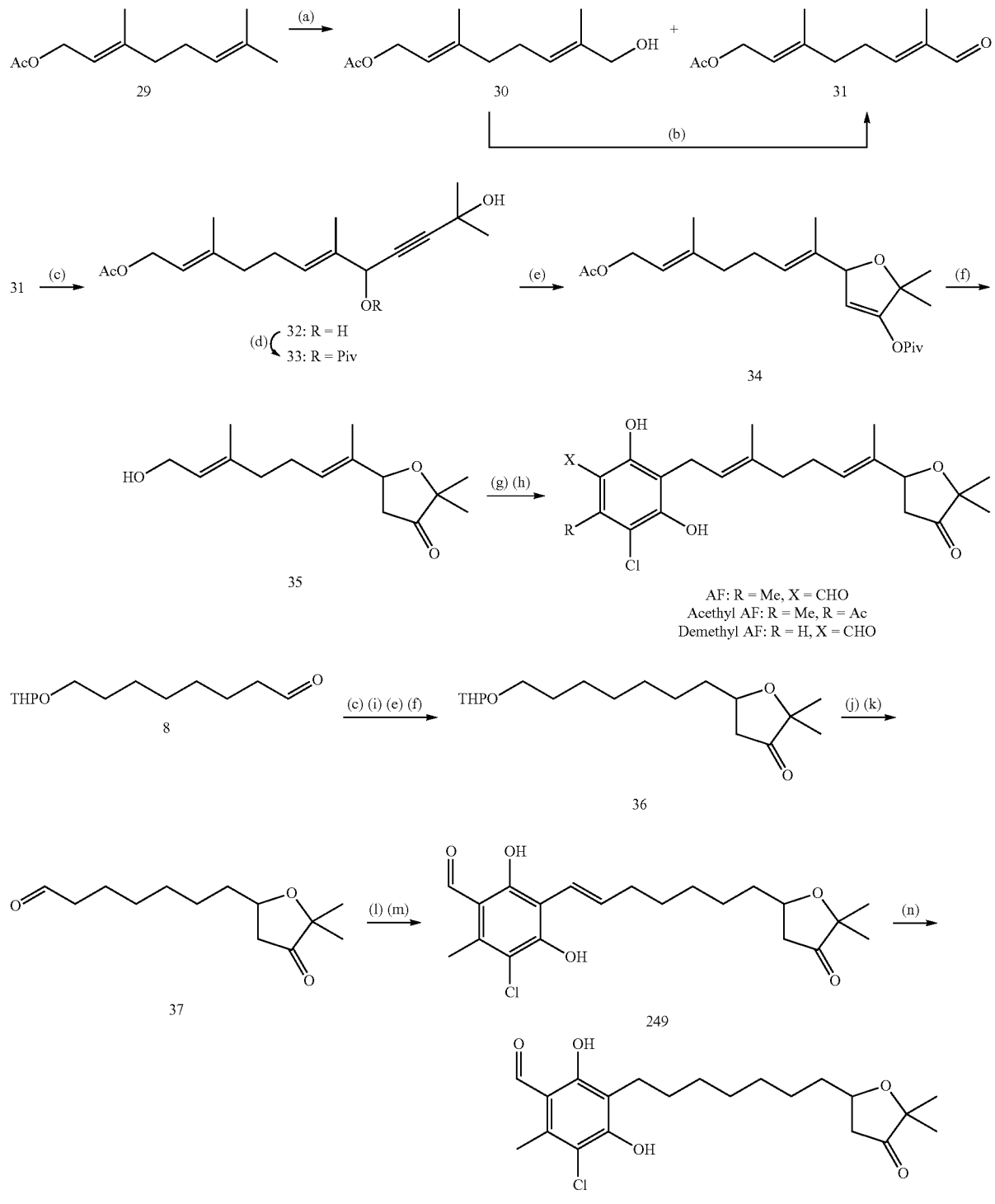

Reagents & conditions: (a) SeO$_2$, EtOH (b) MnO$_2$, Et$_2$O (c) 2-Methyl-3-butyn-2-ol, $^n$BuLi, THF (d) Piv-Cl, pyridine, DMAP, CHCl$_3$ (e) AgBF$_4$, toluene (f) NaOMe, MeOH (g) CBr$_4$, $^n$(C$_8$H$_{17}$)$_3$P, Et$_2$O (h) corresponding resorcinol derivatives, KOH, CaCl$_2$, MeOH (i) Ac$_2$O, pyridine (j) PPTS, EtOH (k) Swern oxidation (l) 112, KOH, CaCl$_2$, MeOH (m) H$_3$PO$_4$, AcOH (n) H$_2$, Pd—C, EtOAc.

dl-5-Chloro-2,4-dihydroxy-6-methyl-3-[(2E,6E)-3-methyl-7-(3,3-dimethyl-4-oxo-2-oxacyclopentyl)-2,6-octadienyl]benzaldehyde (Ascofuranone; AF)

SeO$_2$ (4.34 g, 37.9 mmol) was added to a solution of geranyl acetate (Compound 29, 7.7 ml, 36 mmol) in EtOH (20 ml) at room temperature, and the mixture was refluxed for one hour. The reaction solution was allowed to warm to room temperature, and was filtered through celite. The filtrate was concentrated, and the residue was then subjected to column chromatography on silica gel (Hexane:EtOAc=1:1). The fractions containing alcohol (Compound 30) and aldehyde (Compound 31) were collected. After evaporation of the solvent, the residue was dissolved in Et$_2$O (100 ml). MnO$_2$ (85% purity, 22.5 g, 220 mmol) was added to this solution followed by stirring for 15 hours. The reaction solution was filtered through celite, and the filtrate was washed with a saturated aqueous NaCl solution, and was dried over Na$_2$SO$_4$. After evaporation of the solvent, the residue was purified by column chromatography on silica gel (Hexane:EtOAc=4:1) to yield the aldehyde (Compound 31) (2.142 g, 28%).

BuLi (1.58 M in hexane, 2.7 ml, 4.3 mmol) was added to a solution of 2-Methyl-3-butyl2-ol (185 mg, 2.20 mmol) in THF (14 ml) in a stream of Ar at −20° C., and the mixture was stirred for 2 hours. The reaction solution was cooled to −50° C., and Compound 31 (505 mg, 2.40 mmol) in THF (18 ml) was then added dropwise to the cooled solution. The mixture was stirred at the same temperature for 9 hours. Addition of a saturated aqueous NH$_4$Cl solution (5 ml) then quenched the reaction. The reaction solution was extracted with EtOAc, and the organic layer was washed with a saturated aqueous NaCl solution, and was dried over Na$_2$SO$_4$. After evaporation of the solvent, the residue was purified by column chromatography on silica gel (Hexane:EtOAc=2:1) to yield the diol (Compound 32) (479 mg, 68%).

[Formula 79]

$^1$H-NMR (400 MHz, CDCl$_3$) δ 5.54 (1H, t, J=7.0 Hz, AcOCH$_2$C$\underline{H}$=C), 5.33 {1H, t, J=7.1 Hz, C$\underline{H}$=C(CH$_3$)CH(OH)}, 4.76 {1H, d, J=5.1 Hz, CH=C(CH$_3$)C$\underline{H}$(OH)}, 4.59 (2H, d, J=7.0 Hz, AcOC$\underline{H}_2$CH=C), 2.20-2.16 (2H, m, C$\underline{H}_2$), 2.12-2.09 (2H, m, C$\underline{H}_2$), 2.06 (3H, s, C$\underline{H}_3$C=O), 1.97 {1H, d, J=5.1 Hz, CH=C(CH$_3$)CH(O$\underline{H}$)}, 1.74 (3H, s, C$\underline{H}_3$), 1.71 (3H, s, C$\underline{H}_3$), 1.61 {1H, s, C(O$\underline{H}$)(CH$_3$)$_2$}, 1.53 {6H, s, C(OH)(C$\underline{H}_3$)$_2$}.

IR (neat) 3382, 2978, 2922, 1734, 1711, 1663, 1443, 1362, 1236, 1167, 1024, 951, 864, 712, 610, 554 cm$^{-1}$.

Pyridine (1.06 ml, 13.1 mmol), DMAP (88 mg, 0.72 mmol), and Piv-Cl (0.97 ml, 7.9 mmol) were added to a solution of Compound 32 (1.058 g, 3.594 mmol) in CHCl$_3$ (2.8 ml) in a stream of Ar at 0° C., and the mixture was stirred at the same temperature for 8 hours. H$_2$O was added to the reaction solution, and the organic layer was separated. The aqueous layer was extracted with EtOAc, and the combined organic layer was washed with a saturated aqueous NaCl solution, and was dried over Na$_2$SO$_4$. After evaporation of the solvent, the residue was purified by column chromatography on silica gel (Hexane:EtOAc=7:2) to yield a pivalate (Compound 33) (1.322 g, 97%).

[Formula 80]

$^1$H-NMR (400 MHz, CDCl$_3$) δ 5.77 (1H, s, C$\underline{H}$OPiv), 5.62 {1H, t, J=7.0 Hz, C$\underline{H}$=C(CH$_3$)CHOPiv}, 5.35 (1H, t, J=7.3 Hz, AcOCH$_2$C$\underline{H}$=C), 4.59 (2H, d, J=7.3 Hz, AcOC$\underline{H}_2$CH=C), 2.22-2.16 (2H, m, C$\underline{H}_2$), 2.12-2.08 (2H, m, C$\underline{H}_2$), 2.06 (3H, s, C$\underline{H}_3$C=O), 1.71 (3H, s, C$\underline{H}_3$), 1.69 (3H, s, C$\underline{H}_3$), 1.62 {1H, br, C(O$\underline{H}$)(CH$_3$)$_2$}, 1.51 {6H, s, C(OH)(C$\underline{H}_3$)$_2$}. 1.19 {9H, s, C(C$\underline{H}_3$)$_3$}.

IR (neat) 3460, 2978, 2922, 2866, 1732, 1666, 1481, 1456, 1366, 1265, 1234, 1144, 1028, 955, 932, 864, 785, 708, 608, 561 cm$^{-1}$.

AgBF$_4$ (38 mg, 0.20 mmol) was added to a solution of Compound 33 (937 mg, 2.48 mmol) in toluene (25 ml) in a stream of Ar at room temperature, and the mixture was stirred at 80° C. for 4 hours under light shading. The reaction solution was allowed to warm to room temperature, and H$_2$O was then added to the solution, which was extracted with CHCl$_3$. The combined organic layer was washed with a saturated aqueous NaCl solution, and was dried over Na$_2$SO$_4$. After evaporation of the solvent, the residue was purified by column chromatography on silica gel (Hexane:BuOAc=20:1) to yield the pivalate (Compound 34) (589 mg, 63%).

[Formula 81]

$^1$H-NMR (400 MHz, CDCl$_3$) δ 5.58 (1H, d, J=1.5 Hz, CH=C$\underline{H}$OPiv), 5.47 (1H, t, J=6.8 Hz, CH$_2$CH$_2$C$\underline{H}$=C), 5.34 (1H, dt, J=1.1, 7.0 Hz, AcOCH$_2$C$\underline{H}$=C), 5.14 (1H, d, J=0.8 Hz, C$\underline{H}$=CHOPiv), 4.58 (2H, d, J=7.0 Hz, AcOC$\underline{H}_2$CH=C), 2.20-2.15 (2H, m, C$\underline{H}_2$), 2.10-2.05 (2H, m, C$\underline{H}_2$), 2.06 (3H, s, C$\underline{H}_3$C=O), 1.70 (3H, s, C$\underline{H}_3$), 1.60 (3H, s, C$\underline{H}_3$), 1.37 {3H, s, C(C$\underline{H}_3$)$_2$}, 1.33 {3H, s, C(C$\underline{H}_3$)$_2$}, 1.28 {9H, s, C(C$\underline{H}_3$)$_3$}.

IR (neat) 2978, 2943, 2860, 1763, 1736, 1655, 1481, 1460, 1366, 1331, 1275, 1234, 1146, 1105, 1028, 955, 876, 837, 760, 604, 586 cm$^{-1}$.

NaOMe (1 M in MeOH, 0.63 ml, 0.63 mmol) was added to a solution of Compound 34 (810 mg, 2.14 mmol) in MeOH (63 ml) at room temperature, and the mixture was stirred for 3 hours. H$_2$O was added to the reaction solution, which was extracted with Et$_2$O. The combined organic layer was washed with a saturated aqueous NaCl solution, and was dried over Na$_2$SO$_4$. After evaporation of the solvent, the residue was purified by column chromatography on silica gel (Hexane:EtOAc=4:1) to yield the corresponding primary alcohol (Compound 35) (498 mg, 92%).

CBr$_4$ (1.482 g, 4.469 mmol) and (n-C$_8$H$_{17}$)$_3$P (1.642 g, 4.430 mmol) were added to a solution of the known compound (H. Saimoto et al, Bull. Chem. Soc. Jpn., 1999, 72, 279-284) 35 (448 mg, 1.78 mmol) in Et$_2$O (10 ml) in a stream of Ar at 0° C., and the mixture was stirred at the same temperature for 4 hours. After evaporation of the solvent, the residue was purified by column chromatography on silica gel (Hexane:EtOAc=20:1) to yield the corresponding bromide (538 mg, 96%).

[Formula 82]

$^1$H-NMR (400 MHz, CDCl$_3$) δ 5.54 (2H, m, 2×C$\underline{H}$=C), 4.57 {1H, dd, J=6.4, 10.2 Hz, C(O)CH$_2$C$\underline{H}$}, 4.02 (2H, d, J=8.4 Hz, BrC$\underline{H}_2$CH=C), 2.53 {1H, dd, J=6.4, 18.2 Hz, C(O)C$\underline{H}_2$CH}, 2.45 {1H, dd, J=10.2, 18.2 Hz, C(O)C$\underline{H}_2$CH}, 2.24-2.17 (2H, m, C$\underline{H}_2$), 2.15-2.09 (2H, m, C$\underline{H}_2$), 1.74 (3H, s, C$\underline{H}_3$), 1.67 (3H, s, C$\underline{H}_3$), 1.31 {3H, s, C(C$\underline{H}_3$)$_2$}, 1.24 {3H, s, C(C$\underline{H}_3$)$_2$}.

IR (neat) 2965, 2901, 2860, 1757, 1659, 1460, 1377, 1356, 1342, 1310, 1202, 1170, 1111, 1001, 856, 675 cm$^{-1}$.

Compound 112 (67 mg, 0.36 mmol) and CaCl$_2$.2H$_2$O (37 mg, 0.25 mmol) were added to a solution of this bromide (136 mg, 0.431 mmol) in MeOH (0.5 ml), and the mixture was cooled to 0° C. KOH (1 M in MeOH, 0.76 ml, 0.76 mmol) was added to this cooled mixture, which was stirred for 8 hours. A saturated aqueous NaCl solution was added to the reaction solution, which was extracted with EtOAc. The combined organic layer was dried over Na$_2$SO$_4$, and the solvent was then evaporated. The residue was purified by PTLC (1st run; Hexane:THF=5:1, 2nd run; Hexane:EtOAc=5:1) and recrystallization (Hexane/EtOAc) to yield the target product dl-ascofuranone (52 mg, 34%).

[Formula 83]

Mp 88-90° C.

$^1$H-NMR (500 MHz, CDCl$_3$) δ 2.70 (1H, s, Ar—OH), 10.14 (1H, s, Ar—CHO), 6.43 (1H, s, Ar—OH), 5.51 (1H, t, J=6.9 Hz, CH=C), 5.21 (1H, d, J=7.1 Hz, ArCH$_2$CH=C), 4.52 {1H, dd, J=6.3, 10.1 Hz, C(O)CH$_2$CH}, 3.39 (2H, d, J=7.1 Hz, ArCH$_2$CH=C), 2.61 (3H, s, Ar—CH$_3$), 2.42 {1H, dd, J=6.3, 18.2 Hz, C(O)CH$_2$CH}, 2.35 {1H, dd, J=10.1, 18.2 Hz, C(O)CH$_2$CH}, 2.18-2.14 (2H, m, CH$_2$), 2.06-2.02 (2H, m, CH$_2$), 1.79 (3H, s, CH$_3$), 1.63 (3H, s, CH$_3$), 1.28 {3H, s, C(CH$_3$)$_2$}, 1.22 {3H, s, C(CH$_3$)$_2$}.

IR (KBr) 3327, 2985, 2922, 2874, 1740, 1634, 1582, 1460, 1418, 1371, 1325, 1304, 1283, 1248, 1203, 1171, 1111, 1059, 1011, 907, 824, 712, 631, 592, 523 cm$^{-1}$.

5-Chloro-2,4-dihydroxy-6-methyl-3-[(2E,6E)-7-(5,5-dimethyl-4-oxotetrahydrohuran-2-yl)-3,7-dimethyl-2,6-heptadienyl]acetophenone (Compound 214; Acetyl AF)

The corresponding bromide was prepared from the same known compound 35 as described above, and reacted with the aromatic ring compound 111 in the ketone form as a raw material in a similar manner to yield the target product.

[Formula 84]

$^1$H-NMR (500 MHz, CDCl$_3$) δ 12.64 (1H, s, Ar—OH), 6.26 (1H, s, Ar—OH), 5.50 (1H, t, J=7.0 Hz, ArCH$_2$CH=C), 5.21 (1H, t, J=6.8 Hz, CH=C), 4.52 {1H, dd, J=6.4, 10.0 Hz, CHCH$_2$C=O}, 3.40 (2H, d, J=7.0 Hz, ArCH$_2$CH), 2.61 {3H, s, ArC(O)CH$_3$}, 2.59 (3H, s, ArCH$_3$), 2.40 (1H, dd, J=6.4, 18.3 Hz, CHCH$_2$C=O), 2.34 (1H, dd, J=10.0, 18.3 Hz, CHCH$_2$C=O), 2.19-2.13 (2H, m, CH$_2$), 2.07-2.01 (2H, m, CH$_2$), 1.79 (3H, s, CH$_3$), 1.62 (3H, s, CH$_3$), 1.28 (3H, s, CH$_3$), 1.22 (3H, s, CH$_3$).

5-Chloro-2,4-dihydroxy-3-[(2E,6E)-7-(5,5-dimethyl-4-oxotetrahydrohuran-2-yl)-3,7-dimethyl-2,6-heptadienyl]benzaldehyde (Compound 209; Demethyl AF)

The corresponding bromide was prepared from the same known compound 35 as described above, and reacted with 5-chloro-2,4-dihydroxybenzaldehyde in a similar manner to yield the target product.

[Formula 85]

Mp 70-72° C.

$^1$H-NMR (400 MHz, CDCl$_3$) δ 11.54 (1H, s, Ar—OH), 9.67 (1H, s, CHO), 7.40 (1H, s, Ar—H), 6.39 (1H, s, Ar—OH), 5.51 (1H, t, J=6.8 Hz, CH$_2$CH$_2$CH=C), 5.22 (1H, t, J=7.1 Hz, ArCH$_2$CH=C), 4.53 {1H, dd, J=6.2, 9.9 Hz, C(O)CH$_2$CH}, 3.42 (2H, d, J=7.1 Hz, ArCH$_2$CH=C), 2.46 {1H, dd, J=6.2, 18.0 Hz, C(O)CH$_2$CH}, 2.38 {1H, dd, J=9.9, 18.0 Hz, C(O)CH$_2$CH}, 2.20-2.14 (2H, m, CH$_2$), 2.08-2.02 (2H, m, CH$_2$), 1.79 (3H, s, CH$_3$), 1.63 (3H, s, CH$_3$), 1.29 (3H, s, CH$_3$), 1.23 (3H, s, CH$_3$).

IR (KBr) 3327, 2986, 2921, 2853, 1753, 1649, 1620, 1473, 1433, 137, 1331, 1290, 1252, 1205, 1167, 1111, 1084, 993, 916, 876, 820, 743, 610, 561, 523 cm$^{-1}$.

HRMS (EI) Found: 406.1537. Calcd. for C$_{22}$H$_{27}$ClO$_5$: 406.1547.

3-Chloro-4,6-dihydroxy-2-methyl-5-[(E)-7-(5,5-dimethyl-4-oxo-tetrahydrofuran-2-yl)-1-heptenyl]benzaldehyde (Compound 249)

Aldehyde 8 was converted into furanone 36 in accordance with the method described in the document (H. Saimoto et al., Bull. Chem. Soc. Jpn., 1995, 68, 2727-2734).

[Formula 86]

$^1$H-NMR (500 MHz, CDCl$_3$) δ 4.57 (1H, dd, J=2.8, 4.2 Hz, OCHO), 4.20-4.14 (1H, m, CH$_2$CHCH$_2$C=O), 3.89-3.85 (1H, m, CH$_2$O), 3.73 (1H, dt, J=6.9, 9.4 Hz, CH$_2$O), 3.52-3.48 (1H, m, CH$_2$O), 3.38 (1H, dt, J=6.7, 9.6 Hz, CH$_2$O), 2.55 (1H, dd, J=5.8, 18.1 Hz, CH$_2$C=O), 2.20 (1H, dd, J=10.1, 18.1 Hz, CH$_2$C=O), 1.86-1.80 (1H, m, CH$_2$CHO), 1.77-1.69 (2H, m), 1.64-1.51 (7H, m), 1.48-1.42 (1H, m), 1.35 (7H, br), 1.28 (3H, s, CH$_3$), 1.20 (3H, s, CH$_3$).

IR (neat) 2922, 2854, 1757, 1462, 1443, 1369, 1350, 1177, 1119, 1070, 1032, 988, 905, 872, 814, 731 cm$^{-1}$.

PPTS (1.933 g, 7.692 mmol) was added to a solution of Compound 36 (5.935 g, 19.00 mmol) in EtOH (100 ml), and the mixture was stirred for 4 hours. The reaction solution was allowed to warm to room temperature, and the solvent was then evaporated to about half its volume. The residue was poured into saturated brine. This mixture was extracted with EtOAc twice, and the combined organic layer was dried over Na$_2$SO$_4$. After evaporation of the solvent, the residue was purified by column chromatography on silica gel (Hexane:EtOAc=4:1) to yield the corresponding primary alcohol (4.007 g, 92%).

A solution of DMSO (0.57 ml, 8.0 mmol) in CHCl$_3$ (2.5 ml) was added dropwise to a solution of oxalyl chloride (98% purity, 0.35 ml, 4.1 mmol) in CHCl$_3$ (5 ml) at −60° C. The mixture was stirred at the same temperature for 50 minutes. A solution of the primary alcohol (235 mg, 1.03 mmol) in CHCl$_3$ (2 ml) was added to the mixture, which subsequently was stirred for two more hours. Et$_3$N (2.2 ml, 16 mmol) was added to this mixture, which was stirred for 40 more minutes. A saturated aqueous NH$_4$Cl solution was added to the reaction solution, the organic layer was separated, and by extraction of the aqueous layer with CHCl$_3$. The combined organic layer was dried over Na$_2$SO$_4$, and the solvent was then evaporated. The residue was purified by column chromatography on silica gel (Hexane:EtOAc=5:1) to yield aldehyde 37 (203 mg, 87%).

[Formula 87]

$^1$H-NMR (500 MHz, CDCl$_3$) δ 9.60 (1H, t, J=1.7 Hz, CHO), 4.01 (1H, m, CH$_2$CHCO), 2.39 (1H, dd, J=5.7 Hz, 17.8 Hz, CH$_2$C=O), 2.27 (2H, dt, J=1.6 Hz, 7.4 Hz, CH$_2$CHO), 2.04 (1H, dd, J=10.1 Hz, 17.8 Hz, CH$_2$C=O), 1.62-1.52 (1H, m, CH$_2$CHCH$_2$C=O), 1.51-1.42 (3H, m), 1.35-1.26 (1H, m), 1.20 (5H, br), 1.09 (3H, s, CH$_3$), 1.03 (3H, s, CH$_3$).

IR (neat) 2932, 2860, 2721, 1755, 1724, 1462, 1375, 1360, 1177, 1113, 1011, 83, 702, 534 cm$^{-1}$.

HRMS (EI)) Found: 226.1569. Calcd. for C$_{13}$H$_{22}$O$_3$: M$^+$ 226.1569.

An aldol product was prepared from Compound 112 and Compound 37, and was dehydrated in the presence of H$_3$PO$_4$ to yield target product 249 as in the procedure described above (6% for 2 steps).

[Formula 88]

Mp 99-100° C.

$^1$H-NMR (500 MHz, CDCl$_3$) δ 13.07 (1H, s, Ar—OH), 10.15 (1H, s, Ar—CHO), 6.66 (1H, dt, J=6.9, 16.3 Hz, ArCH=CH), 6.59 (1H, s, Ar—OH), 6.53 (1H, d, J=16.3 Hz, ArCH=CH), 4.18 (1H, m, CHCH$_2$C=O), 2.62 (3H, s, Ar—CH$_3$), 2.57 (1H, dd, J=5.7, 17.9 Hz, CHCH$_2$C=O), 2.28 (2H, q, J=6.9 Hz, CH=CHCH$_2$), 2.21 (1H, dd, J=10.1, 17.9 Hz, CHCH₂C=O), 1.80-1.74 (1H, m, CH₂CHCH₂C=O), 1.66-1.60 (1H, m, CH₂CHCH₂C=O), 1.55-1.48 (2H, m, CH₂), 1.44-1.35 {4H, m, (CH₂)₂}, 1.27 (3H, s, CH₃), 1.20 (3H, s, CH₃).

IR (neat) 3400, 2930, 2858, 1755, 1634, 1462, 1418, 1375, 1285, 1256, 1175, 1113, 978, 910, 733, 675, 592 cm⁻¹.

HRMS (EI) Found: 394.1552. Calcd. for C₂₁H₂₇O₅Cl: M⁺ 394.1547.

5-Chloro-2,4-dihydroxy-6-methyl-3-[7-(3,3-dimethyl-4-oxo-2-oxacyclopentyl)heptyl]benzaldehyde (Compound 250)

Compound 249 was subjected to catalytic reduction to yield the target product as in the procedure described above (98% yield).

[Formula 89]

Mp 70-71° C.

¹H-NMR (500 MHz, CDCl₃) δ 12.66 (1H, s, Ar—OH), 10.14 (1H, s, Ar—CHO), 6.32 (1H, br, Ar—OH), 4.16 (1H, m, CHCH₂C=O), 2.66 (2H, t, J=7.7 Hz, ArCH₂), 2.61 (3H, s, Ar—CH₃), 2.55 (1H, dd, J=5.8, 18.1 Hz, CHCH₂C=O), 2.20 (1H, dd, J=10.1, 18.1 Hz, CHCH₂C=O), 1.78-1.71 (1H, m, CH₂CHCH₂C=O), 1.63-1.56 (2H, m, CH₂), 1.55-1.49 (2H, m, CH₂), 1.47-1.40 (1H, m, CH₂CHCH₂C=O), 1.34 {6H, m, (CH₂)₃}, 1.28 (3H, s, CH₃), 1.20 (3H, s, CH₃).

HRMS (EI) Found: 396.1690. Calcd. for C₂₁H₂₉ClO₅: 396.1704.

13. Compounds 275-10-COOMe, 276-9, 277-11-OAc, 286-11-OAc, 277-9-OH, and 286-9-OH

Methyl (2E,6E)-8-Hydroxy-2,6-dimethylocta-2,6-dienoate (Compound 39)

Ground K₂CO₃ (0.802 g, 5.803 mmol) was added to a solution of aldehyde 31 (2.226 g, 10.59 mmol) in MeOH (50 ml) at room temperature, was stirred for 4 hours. H₂O was added to the reaction solution, which was extracted with EtOAc twice then with Et₂O once. The combined organic layer was washed with a saturated aqueous NH₄Cl solution then with a saturated aqueous NaCl solution, and was dried over Na₂SO₄. After evaporation of the solvent, the residue was purified by column chromatography on silica gel (Hexane:EtOAc=2:1 to 1:2) to yield the corresponding primary alcohol (1.266 g, 71%).

Et₃N (3.1 ml, 22 mmol), DMAP (a catalytic amount), and TBS-Cl (50% in toluene, 8.0 ml, 23 mmol) were added to a solution of this primary alcohol (1.266 g, 7.525 mmol) in CHCl₃ (40 ml) at 0° C., and the mixture was stirred at the same temperature for 2.5 hours. A saturated aqueous NH₄Cl solution was added to the reaction solution, and the organic layer was separated. The aqueous layer was extracted with EtOAc then with Et₂O twice. The combined organic layer was washed with a saturated aqueous NaCl solution, and was dried over Na₂SO₄. After evaporation of the solvent, the residue was subjected to column chromatography on silica gel (Hexane:EtOAc=7:1) to yield the corresponding silyl ether 38 (2.126 g, 100%).

Scheme 13.

[Formula 90]

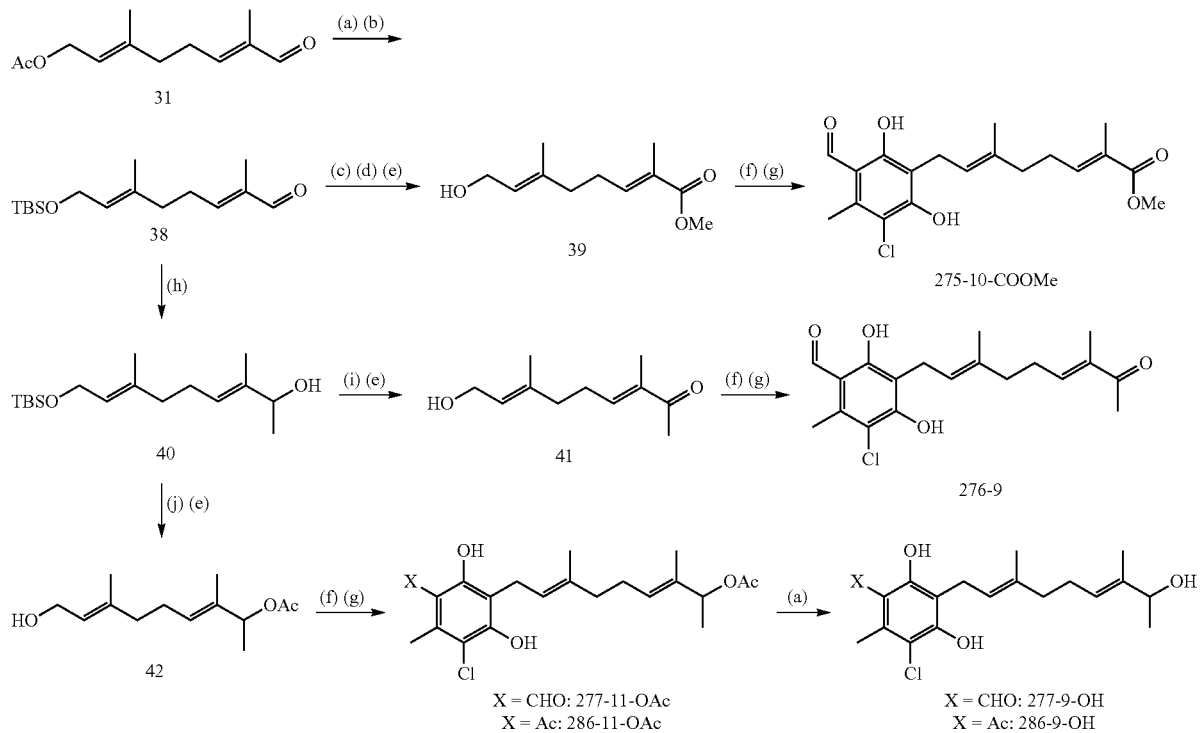

Reagents & conditions: (a) K₂CO₃, MeOH (b) TBS—Cl, Et₃N, DMAP, CHCl₃ (c) NaClO₂, 2-methyl-2-butene, NaH₂PO₄, ᵗBuOH/H₂O (d) MeOH, Ph₃P, DEAD, THF (e) TBAF, THF (f) CBr₄, (ⁿC₈H₁₇)₃P, Et₂O (g) 112, KOH, CaCl₂, MeOH (h) MeLi, THF (i) MnO₂, toluene (j) Ac₂O, pyridine.

[Formula 91]
$^1$H-NMR (400 MHz, CDCl$_3$) δ 9.37 (1H, s, CHO), 6.46 (1H, t, J=7.1 Hz, CH=CCHO), 5.34 (1H, t, J=6.2 Hz, TBSOCH$_2$CH=C), 4.19 (2H, d, J=6.2 Hz, TBSOCH$_2$CH), 2.47 (2H, q, J=7.3 Hz, CH$_2$), 2.19 (2H, t, J=7.3 Hz, CH$_2$), 1.74 (3H, s, CH$_3$), 1.65 (3H, s, CH$_3$), 0.89 (9H, s, C(CH$_3$)$_3$), 0.06 (6H, s, Si(CH$_3$)$_2$).

NaH$_2$PO$_4$.2H$_2$O (1.067 g, 6.839 mmol) and 2-methyl-2-butene (3.0 ml, 28 mmol) were added to a mixed solution of silyl ether 38 (0.772 g, 2.733 mmol) in tBuOH (20 ml)/H$_2$O (5 ml) at room temperature, and the mixture was cooled to 0° C. NaClO$_2$ (79% purity, 0.627 g, 5.48 mmol) was added to this mixture, which was allowed to warm to room temperature with stirring for 15 hours. The reaction solution was diluted with EtOAc, and washed with a saturated aqueous NaCl solution, and the organic layer was dried over Na$_2$SO$_4$. After evaporation of the solvent, the residue was used directly in the next reaction without purification. That is, MeOH (0.13 ml, 3.2 mmol) was added to a solution of Ph$_3$P (0.868 g, 3.309 mmol) in THF (10 ml) at room temperature, and the mixture was cooled to 0° C. DEAD (40% in toluene, 1.35 ml, 2.96 mmol) was added dropwise to the cooled mixture, which was stirred for 30 minutes. A solution of crude carboxylic acid (0.787 g) in THF (10 ml) was added dropwise to the mixture, which was allowed to warm to room temperature with stirring for 4 hours. H$_2$O was added to the reaction solution, and the organic layer was separated, and the aqueous layer was then extracted with EtOAc. The combined organic layer was washed with a saturated aqueous NaCl solution, and was dried over Na$_2$SO$_4$. After evaporation of the solvent, the residue was purified by column chromatography on silica gel (Hexane:EtOAc=3:1) to yield the corresponding methyl ester (0.535 g, 63% for 2 steps).

[Formula 92]
$^1$H-NMR (400 MHz, CDCl$_3$) δ 6.74 (1H, t, J=7.3 Hz, CH=CCO$_2$Me), 5.33 (1H, t, J=6.2 Hz, TBSOCH$_2$CH=C), 4.21 (2H, d, J=6.2 Hz, TBSOCH$_2$CH), 3.73 (3H, s, CO$_2$CH$_3$), 2.30 (2H, q, J=7.5 Hz, CH$_2$), 2.13 (2H, t, J=7.5 Hz, CH$_2$), 1.84 (3H, s, CH$_3$), 1.64 (3H, s, CH$_3$), 0.91 (9H, s, C(CH$_3$)$_3$), 0.07 (6H, s, Si(CH$_3$)$_2$).

The entire methyl ester (0.535 g, 1.712 mmol) was dissolved in THF (20 ml), and the solution was cooled to 0° C. TBAF (1.0 M in THF, 2.0 ml, 2.0 mmol) was then added to the solution, which was allowed to warm to room temperature with stirring for 15 hours. H$_2$O was added to the reaction solution, and the organic layer was separated followed by extraction of the aqueous layer with EtOAc twice. The combined organic layer was washed with a saturated aqueous NaCl solution, and was dried over Na$_2$SO$_4$. After evaporation of the solvent, the residue was purified by column chromatography on silica gel (Hexane:EtOAc=2:1) to yield target side-chain precursor 39 (0.245 g, 72%).

[Formula 93]
$^1$H-NMR (400 MHz, CDCl$_3$) δ 6.73 (1H, t, J=7.3 Hz, CH=CCO$_2$Me), 5.44 (1H, t, J=7.0 Hz, HOCH$_2$CH=C), 4.21 (2H, d, J=6.6 Hz, HOCH$_2$CH), 3.73 (3H, s, CO$_2$CH$_3$), 2.31 (2H, q, J=7.3 Hz, CH$_2$), 2.15 (2H, t, J=7.7 Hz, CH$_2$), 1.84 (3H, s, CH$_3$), 1.69 (3H, s, CH$_3$), 1.45 (1H, br, OH).

Methyl (2E,6E)-8-(3-Chloro-5-formyl-2,6-dihydroxy-4-methyl)phenyl-2,6-dimethyl-2,6-octadienate (Compound 275-10-COOMe)

CBr$_4$ (1.250 g, 3.769 mmol) and (C$_8$H$_{17}$)$_3$P (1.65 ml, 3.07 mmol) were added to a solution of primary alcohol 39 (0.245 g, 1.236 mmol) in Et$_2$O (20 ml) at 0° C., and the mixture was stirred at 0 to 10° C. for 5 hours. After evaporation of the solvent, the residue was subjected to column chromatography on silica gel (Hexane:EtOAc=4:1) to yield the corresponding bromide. The bromide was used directly in the next reaction without further purification.

That is, CaCl$_2$.2H$_2$O (0.419 g, 2.85 mmol) and a solution of the entire bromide above dissolved in MeOH (8.5 ml) were added to a solution of Compound 112 (0.711 g, 3.810 mmol) in KOH (1.0 M in MeOH, 5.7 ml, 5.7 mmol) at 0° C., and the mixture was allowed to warm to room temperature with stirring for 19 hours. The reaction solution was diluted with EtOAc, and was filtered through celite. The filtrate was then washed with a 0.1 M aqueous KOH solution then with a saturated aqueous NaCl solution, and was dried over Na$_2$SO$_4$. After evaporation of the solvent, the residue was subjected to column chromatography on silica gel (Hexane:EtOAc=3:1). The precipitated crude crystals were then recrystallized from a mixed solvent of Hexane:toluene=10:1 to yield target product 275-10-COOMe (0.115 g, 25% yield from Compound 39).

[Formula 94]
Mp 103-105° C.
$^1$H-NMR (400 MHz, CDCl$_3$) δ 12.69 (1H, s, Ar—OH), 10.14 (1H, s, CHO), 6.71 (1H, t, J=7.4 Hz, CH=C), 6.47 (1H, s, Ar—OH), 5.24 (1H, t, J=7.0 Hz, CH=C), 3.71 (3H, s, COOCH$_3$), 3.39 (2H, d, J=7.0 Hz, Ar—CH$_2$), 2.60 (3H, s, Ar—CH$_3$), 2.29-2.23 (2H, m, CH$_2$), 2.11-2.08 (2H, m, CH$_2$), 1.80 (3H, s, CH$_3$), 1.79 (3H, s, CH$_3$).
IR (KBr) 3369, 2957, 2908, 1715, 1624, 1526, 1456, 1433, 1377, 1279, 1240, 1212, 1161, 1128, 962, 907, 808, 787, 712, 627, 596, 569, 527 cm$^{-1}$.

(3E,7E)-9-Hydroxy-3,7-dimethylnona-3,7-diene-2-one (Compound 41)

MeLi (1.0 M in Et$_2$O, 11.5 ml, 11.5 mmol) was added to a solution of aldehyde 38 (1.600 g, 5.664 mmol) in THF (50 ml) at −85° C., and the mixture was allowed to warm to −50° C. with stirring for 2 hours. H$_2$O was added to this mixture to quench the reaction. The organic layer was separated, and the aqueous layer was then extracted with Et$_2$O. The combined organic layer was washed with a saturated aqueous NaCl solution, and was dried over Na$_2$SO$_4$. After evaporation of the solvent, the residue was purified by column chromatography on silica gel (Hexane:EtOAc=4:1) to yield the corresponding secondary alcohol 40 (1.212 g, 72%).

MnO$_2$ (85% purity, 2.05 g, 20.0 mmol) was added to a solution of this secondary alcohol (0.570 g, 1.91 mmol) in toluene (40 ml), and the mixture was stirred vigorously for 18 hours. Additional MnO$_2$ (2.60 g, 25.4 mmol) was added to the mixture, and the stirring was continued for one more day. The reaction solution was filtered through silica gel, and the filtrate was concentrated. The residue was purified by column chromatography on silica gel (Hexane:EtOAc=8:1) to yield the corresponding ketone. In addition, 96 mg of raw material were recovered, and again oxidized with MnO$_2$ (1.20 g, 11.7 mmol) in toluene (10 ml), followed by similar purification to yield a ketone (0.444 g, 87% yield).

The entire ketone (0.444 g, 1.497 mmol) was dissolved in THF (20 ml), and the solution was cooled to 0° C. TBAF (1.0 M in THF, 1.8 ml, 1.8 mmol) was then added to the solution, which was allowed to warm to room temperature with stirring for 2.5 hours. H$_2$O was added to the reaction solution, and the organic layer was separated followed by extraction of the aqueous layer with EtOAc twice. The combined organic layer was washed with saturated saline, and was dried over Na$_2$SO$_4$. After evaporation of the solvent, the residue was purified by column chromatography on silica gel (Hexane:EtOAc=2:1 to 1:1) to yield target product 41 (0.222 g, 81%).

[Formula 95]

$^1$H-NMR (400 MHz, CDCl$_3$) δ 6.61 {1H, t, J=6.4 Hz, CH=C(CH$_3$)C=O}, 5.45 (1H, t, J=7.0 Hz, HOCH$_2$CH=C), 4.21 (2H, d, J=7.0 Hz, HOCH$_2$CH), 2.38 (2H, q, J=7.3 Hz, CH$_2$), 2.30 (3H, s, COCH$_3$), 2.19 (2H, t, J=7.7 Hz, CH$_2$), 1.77 (3H, s, CH$_3$), 1.71 (3H, s, CH$_3$).

(2E,6E)-3-Chloro-4,6-dihydroxy-2-methyl-5-[(2E,6E)-(3,7-dimethyl-8-oxo-2,6-nonadienyl)benzaldehyde (Compound 276-9)

The target product was obtained from alcohol 41 as in the method described above.

[Formula 96]

Mp 119-120° C.

$^1$H-NMR (400 MHz, CDCl$_3$) δ 12.69 (1H, s, Ar—OH), 10.14 (1H, s, CHO), 6.54 (1H, t, J=7.2 Hz, CH=C), 6.39 (1H, s, Ar—OH), 5.26 (1H, t, J=7.3 Hz, CH=C), 3.40 (2H, d, J=7.3 Hz, Ar—CH$_2$), 2.61 (3H, s, Ar—CH$_3$), 2.34 (2H, m, CH$_2$), 2.19 {3H, s, C(O)CH$_3$}, 2.14 (2H, m, CH$_2$), 1.81 (3H, s, CH$_3$), 1.72 (3H, s, CH$_3$).

IR (KBr) 3356, 2920, 2840, 1663, 1620, 1520, 1460, 1425, 1366, 1279, 1236, 1196, 1161, 1111, 962, 903, 812, 787, 708, 631, 592, 569, 527 cm$^{-1}$.

Anal. Found: C, 65.05; H, 6.61; Cl, 10.11%. Calcd for C$_{19}$H$_{23}$ClO$_4$: C, 64.91; H, 6.52; Cl, 10.09%.

(3E,7E)-9-Hydroxy-3,7-dimethylnona-3,7-diene-2-yl acetate (Compound 42)

Ac$_2$O (6 ml) was added to a solution of secondary alcohol 40 (0.682 g, 2.28 mmol) in pyridine (12 ml) at room temperature, and the mixture was stirred for 2.5 hours. The reaction solution was poured into H$_2$O, and was extracted with Et$_2$O twice then with EtOAc once. The combined organic layer was washed with a 1 M aqueous HCl solution then with a saturated aqueous NaCl solution, and was dried over Na$_2$SO$_4$. After evaporation of the solvent, the residue was purified by column chromatography on silica gel (Hexane:EtOAc=4:1) to yield the corresponding acetate (0.585 g, 75%).

[Formula 97]

$^1$H-NMR (400 MHz, CDCl$_3$) δ 5.42 (1H, t, J=7.0 Hz, CH=C(CH$_3$)CHOAc), 5.30 (1H, t, J=6.2 Hz, TBSOCH$_2$CH=C), 5.24 (1H, q, J=6.6 Hz, CH=C(CH$_3$)CHOAc), 4.18 (2H, d, J=6.2 Hz, TBSOCH$_2$CH), 2.13 (2H, q, J=6.6 Hz, CH$_2$), 2.03 (3H, s, COCH$_3$), 2.03 (2H, t, J=7.3 Hz, CH$_2$), 1.62 (6H, s, 2×CH$_3$), 1.28 (3H, d, J=6.6 Hz, CH(OAc)CH$_3$), 0.90 (9H, s, C(CH$_3$)$_3$), 0.07 (6H, s, Si(CH$_3$)$_2$).

The entire acetate (0.585 g, 1.718 mmol) was dissolved in THF (20 ml), and the solution was cooled to 0° C. TBAF (1.0 M in THF, 2.0 ml, 2.0 mmol) was then added to the solution, which was allowed to warm to room temperature with stirring for 17 hours. H$_2$O was added to the reaction solution, and the organic layer was separated followed by extraction of the aqueous layer with EtOAc twice. The combined organic layer was washed with saturated saline, and was dried over Na$_2$SO$_4$. After evaporation of the solvent, the residue was purified by column chromatography on silica gel (Hexane:EtOAc=2:1) to yield target product 42 (0.340 g, 87%).

[Formula 98]

$^1$H-NMR (400 MHz, CDCl$_3$) δ 5.39 (2H, m, 2×CH=C), 5.22 (1H, q, J=6.6 Hz, CHOAc), 4.21 (2H, d, J=6.2 Hz, HOCH$_2$CH), 2.19-2.13 (2H, m, CH$_2$), 2.09-2.05 (2H, m, CH$_2$), 2.03 (3H, s, COCH$_3$), 1.66 (3H, s, CH$_3$), 1.61 (3H, s, CH$_3$), 1.28 (3H, d, J=6.6 Hz, CHCOCH$_3$).

(3E,7E)-9-(3-Chloro-5-formyl-2,6-dihydroxy-4-methyl)phenyl-3,7-dimethyl-3,7-nonadie2-yl acetate (Compound 277-11-OAc)

The target product was obtained from alcohol 42 as in the method described above.

[Formula 99]

Mp 101-102° C.

$^1$H-NMR (400 MHz, CDCl$_3$) δ 12.69 (1H, s, Ar—OH), 10.14 (1H, s, CHO), 6.56 (1H, s, Ar—OH), 5.36 (1H, t, J=7.3 Hz, CH=C), 5.20 {2H. m, CH(OAc)CH$_3$ & CH=C}, 3.39 (2H, d, J=7.3 Hz, Ar—CH$_2$), 2.61 (3H, s, Ar—CH$_3$), 2.10 (2H, m, CH$_2$), 2.02 {3H, s, OC(O)CH$_3$}, 2.03-2.00 (2H, m, CH$_2$), 1.77 (3H, s, CH$_3$), 1.58 (3H, s, CH$_3$), 1.22 {3H, d, J=6.6 Hz, CH(OAc)CH$_3$}.

IR (KBr) 3356, 2986, 2916, 1711, 1624, 1456, 1422, 1377, 1283, 1254, 1157, 1115, 1080, 1024, 959, 910, 841, 808, 708, 631, 583, 544, 523 cm$^{-1}$.

Anal. Found: C, 63.85; H, 6.91; Cl, 8.95%. Calcd for C$_{21}$H$_{27}$ClO$_5$: C, 63.87; H, 6.89; Cl, 8.98%.

(3E,7E)-9-(5-Acetyl-3-chloro-2,6-dihydroxy-4-methyl)phenyl-3,7-dimethyl-3,7-nonadie2-yl acetate (Compound 286-11-OAc)

[Formula 100]

Mp 89-91° C.

$^1$H-NMR (400 MHz, CDCl$_3$) δ 12.57 (1H, s, Ar—OH), 6.35 (1H, s, Ar—OH), 5.37 (2H, t, J=6.8 Hz, CH=C), 5.24-5.17 (2H, m, CH=C & CHOAc), 3.40 (2H, d, J=6.84 Hz, ArCH$_2$), 2.61 (3H, s, ArCH$_3$), 2.58 (3H, s, ArCOCH$_3$), 2.07-2.04 (2H, m, CH$_2$), 2.03-1.99 (2H, s, CH$_2$), 2.02 (3H, s, COCH$_3$), 1.78 (3H, s, CH$_3$), 1.58 (3H, s, CH$_3$), 1.22 (3H, d, J=6.4 Hz, CHOAc).

IR (KBr) 3354, 2978, 2920, 1717, 1611, 1589, 1414, 1379, 1362, 1279, 1258, 1155, 1140, 1096, 1024, 953, 922, 891, 866, 845, 870, 642, 619 cm$^{-1}$.

3-Chloro-4,6-dihydroxy-2-methyl-5-[(2E,6E)-(8-hydroxy-3,7-dimethyl-2,6-nonadienyl)benzaldehyde (Compound 277-9-OH)

K$_2$CO$_3$ (45 mg, 0.33 mmol) was added to a solution of Compound 277-11-OAc (73 mg, 0.185 mmol) in MeOH (10 ml) at room temperature, and the mixture was stirred for 19 hours. A saturated aqueous NH$_4$Cl solution and EtOAc were added to the reaction solution, and the organic layer was separated. The aqueous layer was extracted with EtOAc twice. The combined organic layer was washed with a saturated aqueous NaCl solution, and was dried over Na$_2$SO$_4$. After evaporation of the solvent, the residue was purified by column chromatography on silica gel (Toluene:EtOAc=10:1) to yield the target product (11 mg, 17%).

[Formula 101]

Mp 105-107° C.

$^1$H-NMR (400 MHz, CDCl$_3$) δ 12.71 (1H, s, Ar—OH), 10.14 (1H, s, CHO), 6.61 (1H, s, Ar—OH), 5.32 (1H, t, J=6.6 Hz, CH=C), 5.21 (1H, t, J=7.0 Hz, CH=C), 4.17 (1H, m, CHOH), 3.40 (2H, d, J=7.0 Hz, Ar—CH$_2$), 2.60 (3H, s, Ar—CH$_3$), 2.16-2.08 (2H, m, CH$_2$), 2.07-2.03 (2H, m, CH$_2$), 1.78 (3H, s, CH$_3$), 1.59 (3H, s, CH$_3$), 1.48 (1H, br, OH), 1.20 {3H, d, J=6.2 Hz, CH(OH)CH$_3$}.

IR (KBr) 3341, 2970, 2916, 1616, 1456, 1421, 1377, 1279, 1234, 1165, 1111, 1080, 966, 907, 865, 785, 716, 635, 579 cm$^{-1}$.

(2E,6E)-3-Chloro-4,6-dihydroxy-2-methyl-5-(8-hydroxy-3',7'-dimethyl-2',6'-nonadienyl)acetophenone (Compound 286-9-OH)

[Formula 102]
$^1$H-NMR (400 MHz, CDCl$_3$) δ 12.58 (1H, s, Ar—O$\underline{H}$), 6.40 (1H, s, Ar—O$\underline{H}$), 5.31 (1H, t, J=6.9 Hz, C$\underline{H}$=C), 5.22 (1H, t, J=7.0 Hz, C$\underline{H}$=C), 4.17 (1H, m, C$\underline{H}$OH), 3.41 (2H, d, J=7.0 Hz, Ar—C$\underline{H}_2$), 2.61 (3H, s, Ar—C$\underline{H}_3$), 2.58 (3H, s, C$\underline{H}_3$C=O), 2.17-2.08 (2H, m, C$\underline{H}_2$), 2.07-2.02 (2H, m, C$\underline{H}_2$), 1.78 (3H, s, C$\underline{H}_3$), 1.59 (3H, s, C$\underline{H}_3$), 1.49 (1H, br, OH), 1.20 {3H, d, J=6.6 Hz, CH(OH)C$\underline{H}_3$}.

IR (KBr) 3345, 2972, 2920, 1596, 1410, 1377, 1361, 1287, 1261, 1209, 1159, 1099, 1078, 1049, 986, 949, 922, 885, 862, 843, 772, 604 cm$^{-1}$.

14. Compounds 273-12 and 271-12

Scheme 14.

[Formula 103]

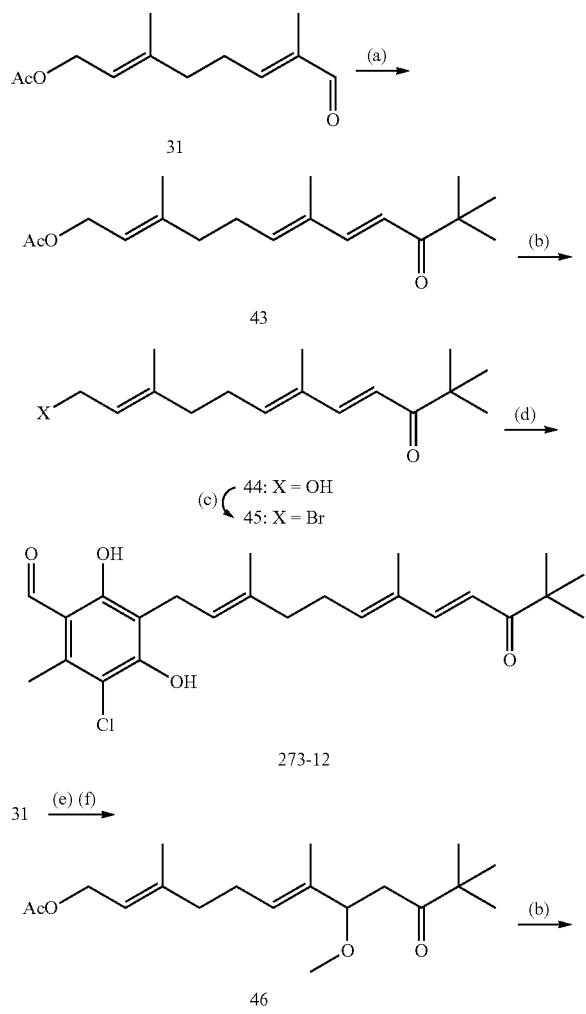

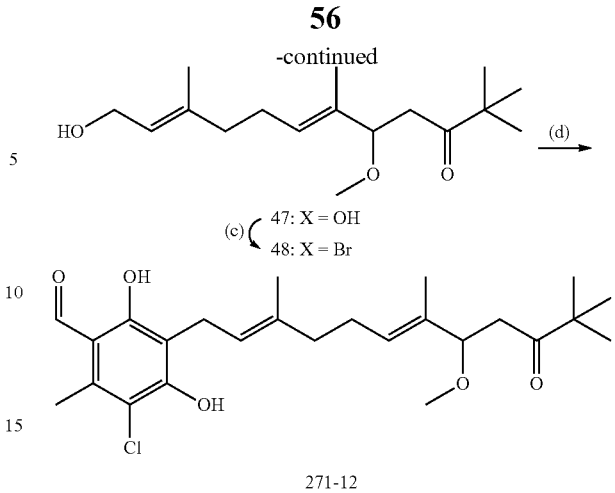

Reagents & conditions: (a) pinacolone, HMDS, $^n$BuLi, THF, rt (b)(NH$_2$)$_2$C=NH HCl, NaOMe, MeOH/CHCl$_3$ (c) CBr$_4$, ($^n$C$_8$H$_{17}$)$_3$P, Et$_2$O (d) 112, KOH, CaCl$_2$, MeOH (e) pinacolone, HMDS, $^n$BuLi, THF, -50° C. (f) MeI, Ag$_2$O, CH$_3$CN.

3-Chloro-4,6-dihydroxy-2-methyl-5-[(2E,6E,8E)-3,7,11,11-tetramethyl-10-oxo-2,6,8-dodecatrienyl]benzaldehyde (Compound 273-12)

BuLi (1.58 M in hexane, 2.4 ml, 3.8 mmol) was added dropwise to a solution of HMDS (0.8 ml, 3.8 mmol) in THF (20 ml) at -50° C., and the mixture was stirred for 10 minutes. Pinacolone (0.44 ml, 3.5 mmol) was added to this mixture, which was allowed to warm to -20° C. with stirring for 2 hours. The reaction solution was cooled to -80° C., and a solution of Compound 31 (0.625 g, 3.184 mmol) in THF (5 ml) was then added dropwise to the cooled mixture. The mixture was stirred at the same temperature for one hour, and allowed to warm to room temperature with stirring for 15 hours. H$_2$O was added to the reaction solution, the organic layer was then separated, and the aqueous layer was extracted with Et$_2$O twice. The combined organic layer was washed with a saturated aqueous NaCl solution, and was dried over Na$_2$SO$_4$. After evaporation of the solvent, the residue was purified by column chromatography on silica gel (Hexane:EtOAc=7:1) to yield the corresponding α,β-unsaturated ketone (Compound 43) (0.333 g, 36%).

[Formula 104]
$^1$H-NMR (400 MHz, CDCl$_3$) δ 7.31 (1H, d, J=15.4 Hz, CH=C$\underline{H}$C=O), 6.47 (1H, d, J=15.4 Hz, C$\underline{H}$=CHC=O), 5.92 (1H, t, J=7.0 Hz, AcOCH$_2$C$\underline{H}$=C), 5.36 (1H, t, J=6.6 Hz, C$\underline{H}$=C(CH$_3$)CH=CH), 4.59 (2H, d, J=7.0 Hz, AcOC$\underline{H}_2$CH=C), 2.38-2.32 (2H, m, C$\underline{H}_2$), 2.17-2.13 (2H, m, C$\underline{H}_2$), 2.06 (3H, s, C$\underline{H}_3$C=O), 1.81 (3H, s, C$\underline{H}_3$), 1.68 (3H, s, C$\underline{H}_3$), 1.18 (9H, s, C(C$\underline{H}_3$)$_3$).

Guanidine hydrochloride (0.120 g, 1.26 mmol) and NaOMe (0.015 g, 0.28 mmol) were added to a mixed solution of Compound 43 (0.333 g, 1.14 mmol) in MeOH (18 ml)/CHCl$_3$ (2 ml) at room temperature, and the mixture was stirred for 6 hours. After evaporation of the solvent, the residue was extracted with EtOAc. The combined organic layer was washed with a saturated aqueous NaCl solution, and was dried over Na$_2$SO$_4$. After evaporation of the solvent, the residue was purified by column chromatography on silica gel (Hexane:EtOAc=7:1) to yield corresponding primary alcohol 44 (0.218 g, 76%).

[Formula 105]
$^1$H-NMR (400 MHz, CDCl$_3$) δ 7.31 (1H, d, J=15.4 Hz, CH=C$\underline{H}$C=O), 6.47 (1H, d, J=15.4 Hz, C$\underline{H}$=CHC=O), 5.93 (1H, t, J=7.3 Hz, HOCH$_2$CH=C), 5.43 (1H, t, J=6.8 Hz, CH=C(CH$_3$)CH=CH), 4.16 (2H, d, J=7.0 Hz, HOCH$_2$CH=C), 2.38-2.32 (2H, m, CH$_2$), 2.15-2.11 (2H, m, CH$_2$), 1.81 (3H, s, CH$_3$), 1.69 (3H, s, CH$_3$), 1.18 (9H, s, C(CH$_3$)$_3$).

CBr$_4$ (0.647 mmol, 1.95 mmol) and (C$_8$H$_{17}$)$_3$P (0.86 ml, 1.93 mmol) were added to a solution of Compound 44 (0.218 g, 0.871 mmol) in CHCl$_3$ (10 ml) at 0° C., and the mixture was stirred for 2 hours. After evaporation of the solvent, the residue was purified by column chromatography on silica gel (Hexane:EtOAc=2:1) to yield a bromide (Compound 45)

The entire bromide was dissolved in MeOH (2.1 ml), and added to a solution of Compound 112 (0.190 g, 1.02 mmol) in KOH (1 M in MeOH, 1.4 ml, 1.4 mmol) at 0° C. CaCl$_2$.2H$_2$O (0.107 g, 0.73 mmol) was added to the mixture, which was allowed to warm to room temperature with stirring for 20 hours. The reaction solution was filtered, and the filtrate was then diluted with EtOAc. This diluted solution was washed with a 0.1 M aqueous KOH solution then with a saturated aqueous NaCl solution, and was dried over Na$_2$SO$_4$. After evaporation of the solvent, the residue was subjected to column chromatography on silica gel (Hexane:EtOAc=3:1), followed by evaporation of the solvent. The resulting crude crystals were purified by recrystallization (Hexane:EtOAc=10:1) to yield the target product. The mother liquor was concentrated, and the residue was purified by column chromatography on silica gel (Hexane:EtOAc=3:1) to yield an additional crop of the target product (in total 70 mg, 19% from Compound 44).

[Formula 106]

Mp. 108-110° C.

$^1$H-NMR (400 MHz, CDCl$_3$) δ 12.69 (1H, s, Ar—OH), 10.14 (1H, s, CHO), 7.23 {1H, d, J=15.4 Hz, CH=CHC(O)}, 6.43 (1H, d, J=15.4 Hz, CH=CHC(O)), 6.40 (1H, s, Ar—OH), 5.37 (1H, t, J=7.0 Hz, CH=C), 5.21 (1H, t, J=6.6 Hz, CH=C), 3.39 (2H, d, J=7.0 Hz, Ar—CH$_2$), 2.61 (3H, s, Ar—CH$_3$), 2.30 (2H, m, CH$_2$), 2.08 (2H, m, CH$_2$), 1.79 (3H, s, CH$_3$), 1.77 (3H, s, CH$_3$), 1.17 (9H, s, C(CH$_3$)$_3$).

IR (KBr) 3194, 2964, 2916, 1672, 1599, 1460, 1421, 1394, 1369, 1275, 1236, 1205, 1165, 1115, 1074, 980, 910, 806, 764, 715, 631, 586 cm$^{-1}$.

3-Chloro-4,6-dihydroxy-2-methyl-5-[(2E,6E)-(8-methoxy-3,7,11,11-tetramethyl-10-oxo-2,6-dodecadienyl)benzaldehyde (Compound 271-12)

BuLi (1.58 M in hexane, 5.0 ml, 7.9 mmol) was added dropwise to a solution of HMDS (1.6 ml, 7.6 mmol) in THF (25 ml) at −50° C., and the mixture was stirred for 15 minutes. Pinacolone (0.96 ml, 7.7 mmol) was added to this mixture, which was allowed to warm to −20° C. with stirring for one hour. The reaction solution was cooled to −80° C., a solution of Compound 31 (1.069 g, 5.084 mmol) in THF (10 ml) was added dropwise to the cooled mixture, which was allowed to warm to −50° C. with stirring for 6 hours. H$_2$O was added to the reaction solution, the organic layer was then separated, and the aqueous layer was extracted with EtOAc twice. The combined organic layer was washed with saturated saline, and was dried over Na$_2$SO$_4$. After evaporation of the solvent, the residue was purified by column chromatography on silica gel (Hexane:EtOAc=3:1) to yield the corresponding aldol product (1.047 g, 66%).

[Formula 107]

$^1$H-NMR (400 MHz, CDCl$_3$) δ 5.44 (1H, t, J=6.4 Hz, AcOCH$_2$CH=C), 5.34 (1H, t, J=7.1 Hz, CH=C(CH$_3$)CH(OH)), 4.59 (2H, d, J=7.3 Hz, AcOCH$_2$CH=C), 4.42 (1H, t, J=5.9 Hz, CH(OH)), 3.22 (1H, br, CH(OH)), 2.68 (2H, d, J=6.0 Hz, CH$_2$C=O), 2.18-2.12 (2H, m, CH$_2$), 2.11-2.07 (2H, m, CH$_2$), 2.06 (3H, s, CH$_3$C=O), 1.71 (3H, s, CH$_3$), 1.64 (3H, s, CH$_3$), 1.15 (9H, s, C(CH$_3$)$_3$).

MeI (1.5 ml, 24 mmol) and Ag$_2$O (0.609 g, 2.63 mmol) were added to a solution of the resulting aldol adduct (0.504 g, 1.624 mmol) in MeCN (5 ml) under Ar at room temperature, and the mixture was refluxed for one day. The reaction solution was allowed to warm to room temperature, and diluted with EtOAc, followed by filtration. The filtrate was washed with water, and the organic layer was dried over Na$_2$SO$_4$. After evaporation of the solvent, the residue was purified by column chromatography on silica gel (Hexane:EtOAc=4:1) to yield the corresponding methyl ether 46 (0.258 g, 49%).

[Formula 108]

$^1$H-NMR (400 MHz, CDCl$_3$) δ 5.33 (1H, t, J=6.3 Hz, CH=C), 5.29 (1H, t, J=7.0 Hz, CH=C), 4.51 (2H, d, J=7.3 Hz, AcOCH$_2$CH=C), 3.97 (1H, dd, J=4.4, 8.0 Hz, CHOCH$_3$), 3.07 (3H, s, OCH$_3$), 2.80 (1H, d, J=8.0, 16.9 Hz, CH$_2$C=O), 2.33 (1H, d, J=4.4, 16.9 Hz, CH$_2$C=O), 2.16-2.01 (4H, m, CH$_2$CH$_2$), 1.99 (3H, s, CH$_3$C=O), 1.63 (3H, s, CH$_3$), 1.48 (3H, s, CH$_3$), 1.05 (9H, s, C(CH$_3$)$_3$).

Besides, a retro-aldol reaction occurred as a side reaction, and the resulting aldehyde 31 was recovered.

A guanidine solution (prepared by adding CHCl$_3$ (1.0 ml) and NaOMe (12 mg, 0.23 mmol) to a solution of guanidine hydrochloride (0.103 g, 1.08 mmol) in MeOH (9.0 ml) followed by stirring for 10 minutes) was added dropwise to a solution of Compound 46 (0.306 g, 0.943 mmol) in MeOH (4.5 ml)/CHCl$_3$ (0.5 ml) in a stream of Ar at room temperature, and the mixture was stirred for 6 hours. After evaporation of the solvent, EtOAc was added to the residue. This mixture was washed with saturated brine, and was dried over Na$_2$SO$_4$. After evaporation of the solvent, the residue was subjected to column chromatography on silica gel (Hexane:EtOAc=2:1) to yield a mixture (213 mg) of primary alcohol 47 and Compound 44 from which the methoxy group was eliminated. This mixture was used directly in the next reaction without further purification. The entire mixture was dissolved in Et$_2$O (20 ml), and the solution was cooled to 0° C. CBr$_4$ (563 mg, 1.70 mmol) and (C$_8$H$_{17}$)$_3$P (0.75 ml, 1.7 mmol) were added to the cooled solution, which was stirred at the same temperature for 2 hours. H$_2$O was added to the reaction solution, followed by extraction with Et$_2$O twice. The combined organic layer was washed with saturated brine, and was dried over Na$_2$SO$_4$. The residue was subjected to column chromatography on silica gel (Hexane:EtOAc=2:1) to yield fraction(s) containing bromides (Compounds 48 and 45)

KOH (1.0 M in MeOH, 3.2 ml, 3.2 mmol) was added to Compound 112 (387 mg, 2.07 mmol), and the mixture was cooled to −10° C. CaCl$_2$.2H$_2$O (221 mg, 1.50 mmol) and a solution of the mixed bromides above in MeOH (5 ml) were added to this cooled mixture, which was stirred at the same temperature for one day. EtOAc and a 0.1 M aqueous KOH solution were added to the reaction solution, and the organic layer was separated. The aqueous layer was then extracted with EtOAc. The combined organic layer was washed with saturated brine, and was dried over Na$_2$SO$_4$. After evaporation of the solvent, the residue was purified by column chromatography on silica gel (hexane/EtOAc=4:1) and PTLC (hexane/EtOAc=7:1) to yield 10 mg of target product (Compound 271-12) (2% from Compound 46) and 12 mg of by-product (Compound 273-12) (3% from Compound 46).

[Formula 109]

¹H-NMR (400 MHz, CDCl₃) δ 12.69 (1H, s, Ar—O$\underline{H}$), 10.14 (1H, s, C$\underline{H}$O), 6.56 (1H, s, Ar—O$\underline{H}$), 5.37 (1H, t, J=6.6 Hz, C$\underline{H}$=C), 5.23 (1H, t, J=7.0 Hz, C$\underline{H}$=C), 3.99 (1H, dd, J=4.4, 8.1 Hz, C(O)CH₂C$\underline{H}$OMe), 3.39 (2H, d, J=7.0 Hz, Ar—C$\underline{H}_2$), 3.08 (3H, s, OC$\underline{H}_3$), 2.85 (1H, dd, J=4.4, 16.6 Hz, C(O)C$\underline{H}_2$CHOMe), 2.61 (3H, s, Ar—C$\underline{H}_3$), 2.39 (1H, dd, J=8.1, 16.6 Hz, C(O)C$\underline{H}_2$CHOMe), 2.19-2.08 (2H, m, C$\underline{H}_2$), 2.05-2.01 (2H, m, C$\underline{H}_2$), 1.78 (3H, s, C$\underline{H}_3$), 1.52 (3H, s, C$\underline{H}_3$), 1.11 (9H, s, C(C$\underline{H}_3$)₃).

15. Compounds 234-12-OPiv, 175-12-OPiv, and 235-12-Opiv

CHCl₃ (10 ml) was added to the partially purified product, and the mixture was cooled to 0° C. Et₃N (0.5 ml, 3.6 mmol), DMAP (18 mg, 0.15 mmol), and Piv-Cl (0.46 ml, 3.8 mmol) were added in this order to the cooled mixture, which was allowed to warm to room temperature with stirring for 16 hours. H₂O (20 ml) was added to the reaction solution, followed by extraction with EtOAc. The combined organic layer was washed with a saturated aqueous NH₄Cl solution, a saturated aqueous NaHCO₃ solution, and a saturated aqueous NaCl solution in this order, and was dried over Na₂SO₄. After evaporation of the solvent, the residue was Scheme 15.

[Formula 110]

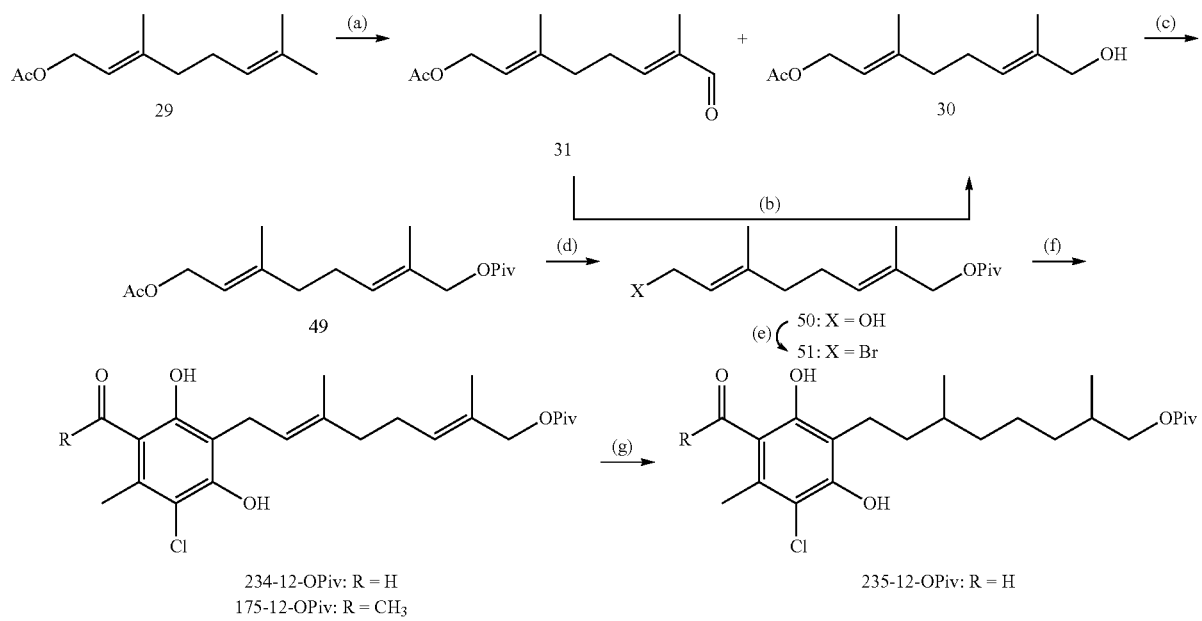

Reagents & conditions: (a) SeO₂, EtOH (b) NaBH₄, EtOH (c) Piv-Cl, Et₃N, DMAP, CH₃Cl (d)(NH₂)₂C=NH HCl, NaOMe, MeOH/CHCl₃ (e) CBr₄, (ⁿC₈H₁₇)₃P, Et₂O (f) 112 or 111, KOH, CaCl₂, MeOH (g) H₂, Pd—C, EtOAc (2E,6E)-8-(3-Chloro-5-formyl-2,6-dihydroxy-4-methylphenyl)-2,6-dimethyl-2,6-octadienyl pivalate (Compound 234-12-OPiv)

SeO₂ (602 mg, 5.43 mmol) was added to a solution of geranyl acetate (Compound 29, 1.0 ml, 4.7 mmol) in EtOH (20 ml) at room temperature, and the mixture was refluxed for one hour. The reaction solution was allowed to warm to room temperature, and was filtered through celite. The filtrate was concentrated, and EtOH (20 ml) was then added to the residue. The mixture was cooled to 0° C. NaBH₄ (58 mg, 1.5 mmol) was added to this cooled mixture followed by stirring for one hour. A 2 M aqueous HCl solution (2 ml) was added to the reaction solution followed by stirring for 5 minutes. The mixture was then poured into H₂O (30 ml). After extraction with EtOAc, the combined organic layer was washed with a saturated aqueous NaCl solution, and was dried over Na₂SO₄. After evaporation of the solvent, the residue was subjected to column chromatography on silica gel (Hexane:EtOAc=2:1) to yield a partially purified primary alcohol (Compound 30) (1.517 g).

purified by column chromatography on silica gel (Hexane:EtOAc=4:1) to yield diester 49 (389 mg, 28% for 2 steps).

[Formula 111]

¹H-NMR (400 MHz, CDCl₃) δ 5.41 (1H, t, J=7.0 Hz, C$\underline{H}$=C), 5.35 (1H, t, J=7.1 Hz, C$\underline{H}$=C), 4.59 (2H, d, J=7.0 Hz, AcOC$\underline{H}_2$), 4.44 (2H, s, C$\underline{H}_2$OPiv), 2.21-2.15 (2H, m, C$\underline{H}_2$), 2.11-2.07 (2H, m, C$\underline{H}_2$), 1.71 (3H, s, C$\underline{H}_3$), 1.64 (3H, s, C$\underline{H}_3$), 1.20 (9H, s, C(C$\underline{H}_3$)₃).

A guanidine solution (prepared by adding CHCl₃ (1.5 ml) and NaOMe (17 mg, 0.32 mmol) to a solution of guanidine hydrochloride (0.146 g, 1.528 mmol) in MeOH (13.5 ml) followed by stirring for 10 minutes) was added dropwise to a mixed solution of diester 49 (411 mg, 1.39 mmol) in MeOH (4.5 ml)/CHCl₃ (0.5 ml) in a stream of Ar at room temperature, and the mixture was stirred for 3 hours. After evaporation of the solvent, EtOAc was added to the residue. This mixture was washed with a saturated aqueous NH₄Cl solution then with saturated brine in this order, and was dried over Na₂SO₄. After evaporation of the solvent, the residue was purified by column chromatography on silica gel (Hexane:EtOAc=3:1 to 2:1) to yield primary alcohol 50 (316 mg, 90%).

[Formula 112]

¹H-NMR (400 MHz, CDCl₃) δ 5.47-5.34 (2H, m, 2×CH=C), 4.44 (2H, s, CH₂OPiv), 4.15 (2H, d, J=6.6 Hz, CH₂OH), 2.23-2.13 (2H, m, CH₂), 2.11-2.03 (2H, m, CH₂), 1.67 (3H, s, CH₃), 1.64 (3H, s, CH₃), 1.42 (1H, br, CH₂OH), 1.21 (9H, s, C(CH₃)₃).

CBr₄ (856 mg, 2.58 mmol) and (C₈H₁₇)₃P (1.1 ml, 2.5 mmol) were added to a solution of primary alcohol 50 (316 mg, 1.24 mmol) in Et₂O (10 ml) in a stream of Ar at 0° C., and the mixture was stirred at the same temperature for 40 minutes. After evaporation of the solvent, the residue was subjected to column chromatography on silica gel (Hexane:EtOAc=10:1) to yield bromide 51.

KOH (0.99 M in MeOH, 7.0 ml, 6.9 mmol) was added to Compound 112 (928 mg, 4.97 mmol), and the mixture was cooled to 0° C. Ground CaCl₂.2H₂O (506 mg, 3.44 mmol) and a solution of Compound 51 (crude, 1.055 g) in MeOH (10 ml) were added to this cooled mixture, which was stirred at –5° C. for 18 hours. After evaporation of the solvent, the residue was diluted with EtOAc (30 ml) and a 0.1 M aqueous KOH solution (30 ml), and was filtered through celite. The filtrate was extracted with EtOAc (2×20 ml), and the combined organic layer was washed with saturated brine (20 ml), and was dried over Na₂SO₄. After evaporation of the solvent, the residue was purified by column chromatography on silica gel (hexane/EtOAc=5:1). The resulting solid was further purified by recrystallization (hexane) to yield target product 234-12-OPiv (213 mg, 41%).

[Formula 113]

Mp 60° C.

¹H-NMR (400 MHz, CDCl₃) δ 12.70 (1H, s, Ar—OH), 10.14 (1H, s, Ar—CHO), 6.54 (1H, s, Ar—OH), 5.38 (1H, t, J=6.8 Hz, CH=C), 5.22 (1H, t, J=6.8 Hz, CH=C), 4.40 (2H, s, CH₂OPiv), 3.39 (2H, d, J=6.8 Hz, Ar—CH₂), 2.60 (3H, s, Ar—CH₃), 2.16-2.11 (2H, m, CH₂), 2.04-2.00 (2H, m, CH₂), 1.78 (3H, s, CH₃), 1.61 (3H, s, CH₃), 1.20 {9H, s, C(CH₃)₃}.

¹³C-NMR (100 MHz, CDCl₃) δ 193.3, 178.4, 162.2, 156.4, 137.7, 136.2, 130.3, 128.4, 121.2, 114.4, 113.6, 113.3, 69.9, 39.1, 38.9, 27.2, 26.1, 22.0, 16.1, 14.4, 13.8.

IR (KBr) 3244, 2978, 2922, 1728, 1616, 1485, 1450, 1421, 1369, 1279, 1234, 1157, 1105, 1032, 959, 910, 876, 770, 718, 635, 604, 575, 536 cm⁻¹.

Anal. Found: C, 65.07; H, 7.32; Cl, 8.44%. Calcd for C₂₃H₃₁ClO₅: C, 65.32; H, 7.39; Cl, 8.38%.

(2E,6E)-8-(5-Acetyl-3-chloro-2,6-dihydroxy-4-methylphenyl)-2,6-dimethyl-2,6-octadienyl pivalate (Compound 175-12-OPiv)

The target product was obtained by synthesizing in a similar manner using Compound 111 as raw material for aromatic ring.

[Formula 114]

¹H-NMR (400 MHz, CDCl₃) δ 12.62 (1H, s, Ar—OH), 6.31 (1H, s, Ar—OH), 5.38 (1H, t, J=6.8 Hz, CH=C), 5.23 (1H, t, J=6.2 Hz, CH=C), 4.39 (2H, s, CH₂OPiv), 3.40 (2H, d, J=7.3 Hz, Ar—CH₂), 2.61 (3H, s, Ar—CH₃), 2.59 (3H, s, CH₃C=O), 2.17-2.10 (2H, m, CH₂), 2.06-1.98 (2H, m, CH₂), 1.79 (3H, s, CH₃), 1.60 (3H, s, CH₃), 1.19 {9H, s, C(CH₃)₃}.

IR (KBr) 3412, 2978, 2922, 1728, 1610, 1464, 1416, 1360, 1279, 1157, 1094, 1036, 984, 951, 841, 768, 600 cm⁻¹.

HRMS (EI) Found: 436.2024. Calcd. for C₂₄H₃₃ClO₅: 436.2017.

8-(3-Chloro-5-formyl-2,6-dihydroxy-4-methylphenyl)-2,6-dimethyloctyl pivalate (Compound 235-12-OPiv)

Compound 234-12-OPiv was reduced as in Scheme 1 to yield the target product.

[Formula 115]

¹H-NMR (400 MHz, CDCl₃) δ 12.61 (1H, s, Ar—OH), 10.10 (1H, s, Ar—CHO), 6.50 (1H, d, J=12.1 Hz, Ar—OH), 3.98-3.93 (1H, m, CH₂OPiv), 3.87-3.82 (1H, m, CH₂OPiv), 2.66-2.59 (2H, m, Ar—CH₂), 2.56 (3H, s, Ar—CH₃), 1.80-1.70 (2H, m, CH₂), 1.53-1.41 (2H, m), 1.36-1.27 (4H, br, CH₂CH₂), 1.23-1.17 (2H, m), 1.17 {9H, s, C(CH₃)₃}, 0.91 (3H, d, J=7.0 Hz, CH(CH₃)), 0.90 (3H, d, J=7.0 Hz, CHCH₃).

¹³C-NMR (100 MHz, CDCl₃) δ 193.19, 178.75, 162.31, 156.22, 137.20, 115.6, 113.45, 113.86, 69.18, 38.83, 36.79, 35.21, 33.74, 32.77, 32.61, 27.19, 23.89, 20.43, 19.61, 16.99, 14.39.

IR (neat) 3395, 2961, 2932, 2872, 1724, 1717, 1634, 1462, 1422, 1375, 1290, 1248, 1167, 1034, 980, 800, 710, 592 cm⁻¹.

HRMS (EI) Found: 426.2144. Calcd. for C₂₃H₃₅ClO₅: 426.2173.

16. Compounds 264-11-OPiv and 265-11-Opiv

Scheme 16.

[Formula 116]

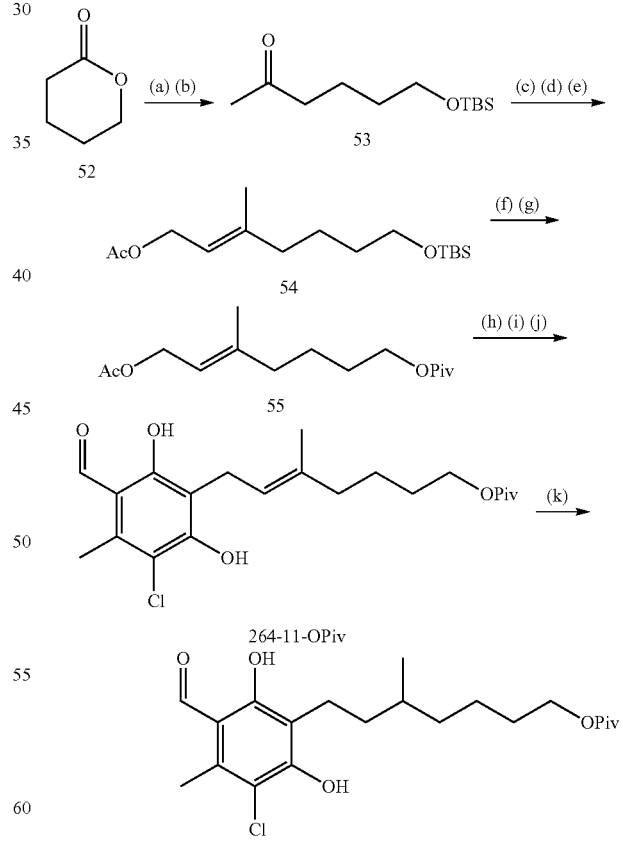

Reagennts & conditions: (a) MeLi, THF (b) TBS—Cl, Et₃N, DMAP, CHCl₃ (c) (EtO)₂P(O)CH₂CO₂Et, NaH, THF (d) DIBAL, toluene (e) Ac₂O, pyridine (f) TBAF, THF (g) Piv-Cl, Et₃N, DMAP, CHCl₃ (h) (NH₂)₂C=NH HCl, NaOMe, MeOH/CHCl₃ (i) CBr₄, Ph₃P, CHCl₃ (j) 112, KOH, CaCl₂, MeOH (k) H₂, Pd—C, EtOAc

(5E)-7-(3-Chloro-5-formyl-2,6-dihydroxy-4-methyl-phenyl)-5-methyl-5-heptenyl pivalate (Compound 264-11-OPiv)

MeLi (1.04 M in $Et_2O$, 33 ml, 34 mmol) was added dropwise to a solution of 6-Valerolactone (Compound 52, 3.0 ml, 32 mmol) in THF (50 ml) under Ar at −80° C., and the mixture was allows to warm to −65° C. with stirring for 4 hours. Addition of $H_2O$ quenched the reaction, and the stirring was continued at room temperature for 5 minutes. The organic layer was then separated, and the aqueous layer was extracted with EtOAc twice. The combined organic layer was washed with saturated saline, and was dried over $Na_2SO_4$. After evaporation of the solvent, the residue was purified by column chromatography on silica gel (EtOAc) to yield 7-hydroxy-2-hexanone (2.545 g, 68%).

$Et_3N$ (6.1 ml, 44 mmol), DMAP (a catalytic amount), and TBS-Cl (50% in toluene, 4.5 ml, 27 mmol) were added to a solution of this ketone (2.545 g, 21.91 mmol) in $CHCl_3$ (70 ml) at 0° C., and the mixture was allowed to warm to room temperature with stirring for 13 hours. $H_2O$ was added to the reaction solution, which was stirred for 5 minutes. The organic layer was then separated, and the aqueous layer was extracted with EtOAc twice. The combined organic layer was washed with a saturated aqueous $NH_4Cl$ solution then with saturated brine, and was dried over $Na_2SO_4$. After evaporation of the solvent, the residue was purified by column chromatography on silica gel (Hexane:EtOAc=5:1) to yield the corresponding silyl ether 53 (4.385 g, 87%).

[Formula 117]
$^1$H-NMR (400 MHz, $CDCl_3$) δ 3.57 (2H, t, J=6.6 Hz, C$\underline{H}_2$OTBS), 2.41 (2H, t, J=7.3 Hz, C(O)C$\underline{H}_2$CH$_2$), 2.09 (3H, s, C$\underline{H}_3$C=O), 1.62-1.55 (2H, m, C$\underline{H}_2$), 1.51-1.43 (2H, m, C$\underline{H}_2$), 0.85 (9H, s, C(C$\underline{H}_3$)$_3$), 0.01 (6H, s, Si(C$\underline{H}_3$)$_2$).

Triethyl phosphonoacetate (0.7 ml, 3.2 mmol) was added to a suspension of NaH (60% in oil, 146 mg, 3.65 mmol) in THF (20 ml) under Ar at 0° C., and the mixture was allowed to warm to room temperature with stirring for 1.5 hours. The mixture was cooled to −65° C., and a solution of Compound 53 (676 mg, 2.93 mmol) in THF (10 ml) was added dropwise to the cooled mixture, which was allowed to warm to room temperature with stirring for 16 hours. Addition of $H_2O$ quenched the reaction, and the stirring was continued for 5 minutes. The organic layer was separated, and the aqueous layer was extracted with $Et_2O$ twice. The combined organic layer was washed with a saturated aqueous $NH_4Cl$ solution, and was dried over $Na_2SO_4$. After evaporation of the solvent, the residue was purified by column chromatography on silica gel (Hexane:EtOAc=10:1) to yield the corresponding unsaturated ester in the form of (E)-isomer or a mixture of (E)- and (Z)-isomers (total 0.336 g, 38%).

[Formula 118]
(E)-isomer: $^1$H-NMR (400 MHz, $CDCl_3$) δ 5.66 (1H, d, J=1.1 Hz, C=C$\underline{H}$CO$_2$Et), 4.14 (2H, q, J=7.3 Hz, CO$_2$C$\underline{H}_2$CH$_3$), 3.61 (2H, t, J=5.9 Hz, C$\underline{H}_2$OTBS), 2.17-2.13 (2H, m, CH=C(CH$_3$)C$\underline{H}_2$), 2.15 (3H, d, J=1.1 Hz, CH=C(C$\underline{H}_3$)CH$_2$), 1.55-1.51 (4H, m, (C$\underline{H}_2$)$_2$), 1.28 (3H, t, J=7.3 Hz, CO$_2$CH$_2$C$\underline{H}_3$), 0.89 (9H, s, C(C$\underline{H}_3$)$_3$), 0.05 (6H, s, Si(C$\underline{H}_3$)$_2$).

DIBAL (1.0 M in hexane, 25 ml, 25 mmol) was added dropwise to a solution of the unsaturated ester (1.441 g, 4.795 mmol) in the form of (E)-isomer in toluene (50 ml) under Ar at −80° C., and the mixture was stirred at −65° C. for 2.5 hours. To the reaction solution was added slowly EtOAc, followed by $H_2O$ and a 2 M aqueous HCl solution. The mixture was allowed to warm to room temperature with stirring for 15 minutes. After filtration through celite, the organic layer in the filtrate was separated. The aqueous layer was further extracted with EtOAc twice. The combined organic layer was washed with a saturated aqueous $NaHCO_3$ solution then with a saturated aqueous NaCl solution, and was dried over $Na_2SO_4$. After evaporation of the solvent, the residue was loaded on column chromatography on silica gel (Hexane:EtOAc=1:1) to yield the corresponding crude allyl alcohol (1.458 g).

The entire crude allyl alcohol was dissolved in pyridine (12 ml), and $Ac_2O$ (6 ml) was added to the solution at room temperature followed by stirring for 5 hours. The reaction solution was diluted with EtOAc, and $H_2O$ and a 2 M aqueous HCl solution were added to the diluted solution followed by stirring for 5 minutes. The organic layer was separated, and the aqueous layer was then extracted with EtOAc twice. The combined organic layer was washed with a saturated aqueous $NaHCO_3$ solution then with a saturated aqueous NaCl solution, and was dried over $Na_2SO_4$. After evaporation of the solvent, the residue was purified by column chromatography on silica gel (Hexane:EtOAc=7:1) to yield the corresponding acetate 54 (1.259 g, 87% for 2 steps).

[Formula 119]
$^1$H-NMR (400 MHz, $CDCl_3$) δ 5.34 (1H, dt, J=1.1, 7.0 Hz, C=C$\underline{H}$), 4.57 (2H, d, J=7.0 Hz, C$\underline{H}_2$OAc), 3.61 (2H, t, J=6.0 Hz, C$\underline{H}_2$OTBS), 2.13-2.05 (5H, m, C$\underline{H}_3$OC=O & CH=C(CH$_3$)C$\underline{H}_2$), 1.69 (3H, s, CH=C(C$\underline{H}_3$)CH$_2$), 1.53-1.43 (4H, m, C$\underline{H}_2$CH$_2$), 0.89 (9H, s, C(C$\underline{H}_3$)$_3$), 0.05 (6H, s, Si(C$\underline{H}_3$)$_2$).

TBAF (1.0 M in THF, 5.0 ml, 5.0 mmol) was added to a solution of Compound 54 (1.26 g, 4.19 mmol) in THF (30 ml) at 0° C., and the mixture was allowed to warm to room temperature followed by stirring for 6 hours. Additional TBAF (0.5 ml, 0.5 mmol) was added to the mixture, which was stirred for 2 hours. $H_2O$ was then added to the reaction solution to quench the reaction. After extraction with EtOAc, the combined organic layer was washed with a saturated aqueous $NaHCO_3$ solution then with a saturated aqueous NaCl solution, and was dried over $Na_2SO_4$. After evaporation of the solvent, the residue was purified by column chromatography on silica gel (Hexane:EtOAc=2:1 to 1:1) to yield the corresponding primary alcohol (0.741 g, 95%).

[Formula 120]
$^1$H-NMR (400 MHz, $CDCl_3$) δ 5.35 (1H, dt, J=1.1, 7.0 Hz, C=C$\underline{H}$), 4.58 (2H, d, J=7.0 Hz, C$\underline{H}_2$OAc), 3.65 (2H, t, J=6.2 Hz, C$\underline{H}_2$OH), 2.08-2.05 (5H, m, C$\underline{H}_3$OC=O & CH=C(CH$_3$)C$\underline{H}_2$), 1.70 (3H, s, CH=C(C$\underline{H}_3$)CH$_2$), 1.59-1.46 (4H, m, C$\underline{H}_2$CH$_2$).

$Et_3N$ (0.65 ml, 4.7 mmol), DMAP (a catalytic amount), and Piv-Cl (0.55 ml, 4.5 mmol) were added to a solution of this primary alcohol (0.741 g, 3.98 mmol) in $CHCl_3$ (30 ml) at 0° C., and the mixture was stirred at room temperature for 16 hours. $H_2O$ was added to the reaction solution, which was stirred for 5 minutes. The organic layer was then separated, and the aqueous layer was extracted with EtOAc twice. The combined organic layer was washed with a saturated aqueous $NaHCO_3$ solution then with saturated brine, and was dried over $Na_2SO_4$. After evaporation of the solvent, the residue was purified by column chromatography on silica gel (Hexane:EtOAc=5:1 to 1:1) to yield pivalate 55 (0.471 g, 44%).

[Formula 121]
$^1$H-NMR (400 MHz, $CDCl_3$) δ 5.35 (1H, t, J=7.1 Hz, C=C$\underline{H}$), 4.58 (2H, d, J=7.0 Hz, C$\underline{H}_2$OAc), 4.06 (2H, t, J=6.4 Hz, C$\underline{H}_2$OPiv), 2.09-2.03 (5H, m, C$\underline{H}_3$OC=O & C H̲=C(CH₃)CH̲₂), 1.69 (3H, s, CH=C(CH₃)CH₂), 1.63-1.57 (2H, m, CH̲₂), 1.53-1.46 (2H, m, CH̲₂), 1.20 (9H, s, C(CH̲₃)₃).

The unreacted raw material was recovered (0.392 g, 53%).

Guanidine hydrochloride (0.184 g, 1.926 mmol) and NaOMe (0.024 g, 0.44 mmol) were added to a mixed solvent of MeOH (13.5 ml) and CHCl₃ (1.5 ml) under Ar at room temperature, and the mixture was stirred for 10 minutes. This solution was added dropwise to a mixed solution of Compound 55 (0.471 g, 1.74 mmol) in MeOH (4.5 ml) and CHCl₃ (0.5 ml), and the mixture was stirred at room temperature for 5 hours. After evaporation of the solvent, EtOAc and H₂O were added to the residue, and the organic layer was separated. The aqueous layer was further extracted with EtOAc, and the combined organic layer was washed with a saturated aqueous NaHCO₃ solution then with a saturated aqueous NaCl solution, and was dried over Na₂SO₄. After evaporation of the solvent, the residue was purified by column chromatography on silica gel (Hexane:EtOAc=2:1) to yield the corresponding allyl alcohol (0.376 g, 95%).

[Formula 122]

¹H NMR (400 MHz, CDCl₃) δ 5.42 (1H, ddt, J=1.5, 2.6, 7.0 Hz, C=CH̲), 4.16 (2H, d, J=6.6 Hz, CH̲₂OH), 4.06 (2H, t, J=6.2 Hz, CH̲₂OPiv), 2.05 (2H, t, J=7.3 Hz, CH=C(CH₃)CH̲₂), 1.67 (3H, s, CH=C(CH̲₃)CH₂), 1.63-1.58 (2H, m, CH̲₂), 1.53-1.46 (2H, m, CH̲₂), 1.28 (1H, br, OH̲), 1.19 (9H, s, C(CH̲₃)₃).

Ph₃P (0.952 g, 3.63 mmol) and CBr₄ (1.205 g, 3.633 mmol) were added to a solution of this allyl alcohol (0.376 g, 1.65 mmol) in CHCl₃ (20 ml) at 0° C., and the mixture was stirred for one hour. After evaporation of the solvent, the residue was purified by column chromatography on silica gel (Hexane:EtOAc=2:1) to yield the corresponding bromide. The bromide was used directly in the next reaction without further purification.

That is, KOH (1.0 M in MeOH, 11.0 ml, 11.0 mmol) was added to a solution of Compound 112 (1.358 g, 7.278 mmol) in MeOH (10 ml), and the mixture was cooled to 0° C. A solution of the bromide (crude, 0.736 g) in MeOH (10 ml), and CaCl₂.2H₂O (0.749 g, 5.09 mmol) were added to the cooled mixture, which was stirred at room temperature for one day. The reaction solution was filtered through celite, and the filtrate was then concentrated. The residue was diluted with EtOAc and a 0.1 M aqueous KOH solution. The organic layer was separated, and the aqueous layer was extracted with Et₂O twice then with EtOAc once. The combined organic layer was washed with a saturated aqueous NaCl solution, and was dried over Na₂SO₄. After evaporation of the solvent, the residue was purified by column chromatography on silica gel (Hexane:EtOAc=4:1), followed by recrystallization from hexane twice to yield the target product (0.188 g, 28%).

[Formula 123]

Mp 74-75° C.
¹H-NMR (400 MHz, CDCl₃) δ 12.69 (1H, s, Ar—OH̲), 10.14 (1H, s, Ar—CHO), 6.42 (1H, s, Ar—OH̲), 5.22 (1H, dt, J=1.5, 7.3 Hz, CH̲=C), 4.03 (2H, t, J=6.4 Hz, CH̲₂OPiv), 3.40 (2H, d, J=7.3 Hz, Ar—CH̲₂), 2.61 (3H, s, Ar—CH̲₃), 2.00 (2H, t, J=7.5 Hz, CH=C(CH₃)CH̲₂), 1.77 (3H, s, CH=C(CH̲₃)CH₂), 1.58-1.53 (2H, m, CH̲₂), 1.49-1.43 (2H, m, CH̲₂), 1.18 (9H, s, C(CH̲₃)₃).

IR (KBr) 3188, 2964, 2874, 1728, 1607, 1477, 1456, 1421, 1377, 1283, 1231, 1161, 1111, 1031, 910, 868, 770, 712, 631, 592 cm⁻¹.

Anal. Found: C, 63.53; H, 7.41; Cl, 8.72%. Calcd for C₂₁H₂₉ClO₅: C, 63.55; H, 7.36; Cl, 8.93%.

In addition, the aqueous layer was acidified with a 2 M hydrochloric acid, and was extracted with EtOAc to recover unreacted Compound 112.

7-(3-Chloro-2,6-dihydroxy-5-formyl-4-methylphenyl)-5-methylheptyl pivalate (Compound 265-11-OPiv)

Pd—C (a catalytic amount) was added to a solution of Compound 264-11-OPiv (0.130 g, 0.328 mmol) in EtOAc (10 ml) at 0° C., and the mixture was stirred under H₂ atmosphere for 5 hours. The Pd—C was filtered out, and the solvent was then evaporated. The residue was purified by column chromatography on silica gel (Hexane:EtOAc=7:1) to yield the target product (0.108 g, 83%).

[Formula 124]

¹H-NMR (400 MHz, CDCl₃) δ 12.65 (1H, s, Ar—OH̲), 10.14 (1H, s, Ar—CHO), 6.35 (1H, br, Ar—OH̲), 4.05 (2H, t, J=6.6 Hz, CH̲₂OPiv), 2.70-2.63 (2H, m, Ar—CH̲₂), 2.60 (3H, s, Ar—CH̲₃), 1.64-1.57 (2H, m, CH̲₂), 1.55-1.30 (5H, m, CH̲CH₃ & CH̲₂CH₂), 1.23-1.17 (2H, m, CH̲₂), 1.19 (9H, s, C(CH̲₃)₃), 0.95 (3H, d, J=6.2 Hz, CH(CH̲₃)CH₂).

IR (KBr) 3391, 2957, 2874, 1720, 1628, 1481, 1468, 1421, 1373, 1292, 1248, 1165, 1126, 1094, 1036, 972, 937, 802, 708, 631, 590, 523 cm⁻¹.

HRMS (EI) Found: 398.1865. Calcd. for C₂₁H₃₁ClO₅: 398.1860.

17. Compounds 264-8, 265-8, (Z)-264-8, 268-8, 270-8, and 269-8

Scheme 17.

[Formula 125]

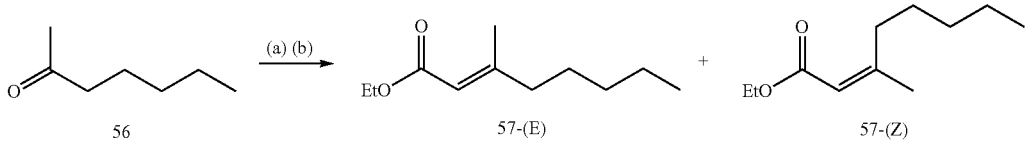

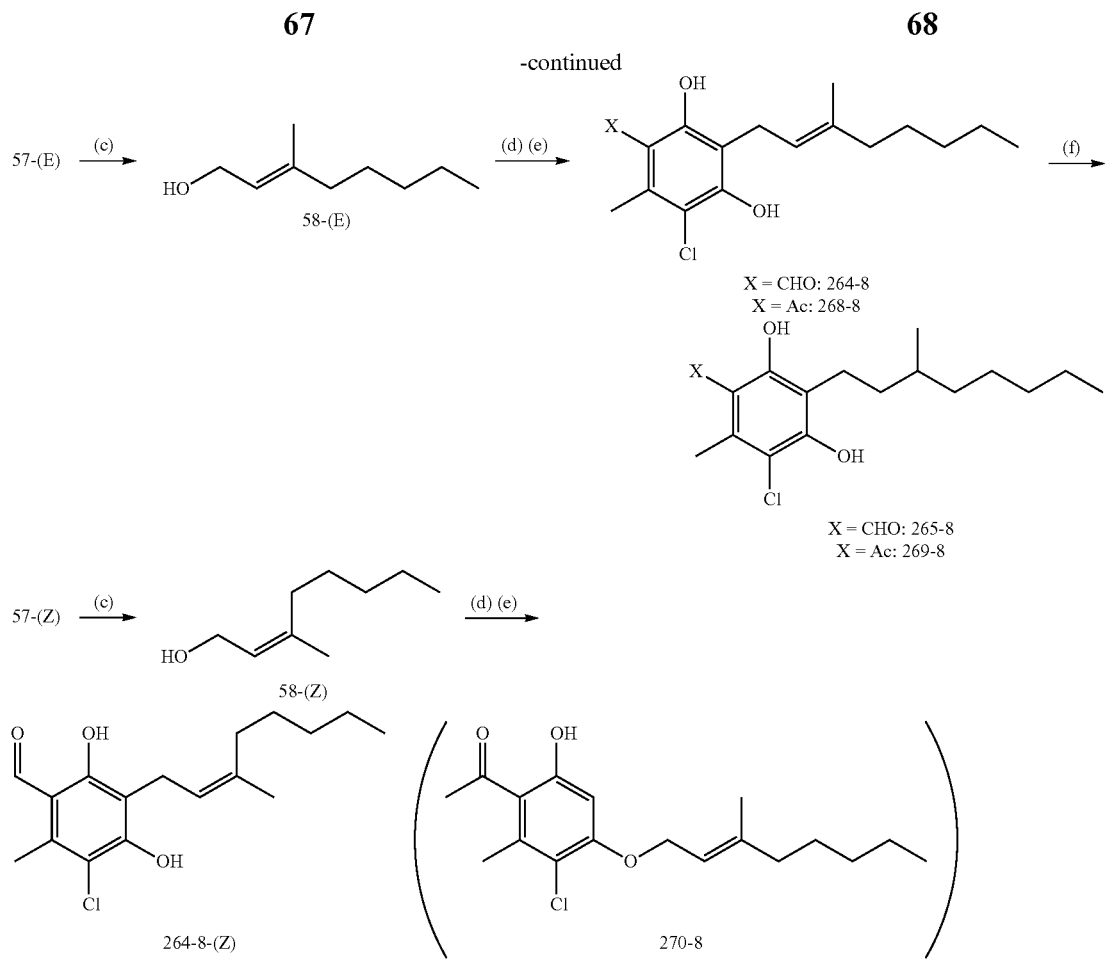

Reagents & conditions: (a) (EtO)₂P(O)CH₂CO₂Et, NaH, THF (b) Silica gel column chromatography (c) DIBAL, toluene (d) CBr₄, Ph₃P, CHCl₃ (e) 112 or 111, KOH, CaCl₂, MeOH (f) H₂, Pd—C, EtOAc (E)-3-Chloro-4,6-dihydroxy-2-methyl-5-(3-methyl-2-octenyl)benzaldehyde (Compound 264-8)

Triethyl phosphonoacetate (2.4 ml, 11 mmol) was added to a suspension of NaH (60% in oil, 0.511 g, 12.8 mmol) in THF (20 ml) at 0° C., and the mixture was allowed to warm to room temperature with stirring for 1.5 hours. The mixture was cooled to −65° C., and 2-hetanone (Compound 56, 1.3 ml, 9.3 mmol) was added dropwise to the cooled mixture, which was allowed to warm to room temperature with stirring for one day. Addition of H₂O quenched the reaction, and the stirring was continued for 5 minutes. The organic layer was separated, and the aqueous layer was extracted with Et₂O once then with EtOAc once. The combined organic layer was washed with a saturated aqueous NH₄Cl solution then with a saturated aqueous NaCl solution, and was dried over Na₂SO₄. After evaporation of the solvent, the residue was purified by column chromatography on silica gel (Hexane:EtOAc=30:1) to yield unsaturated ester 57 in the form of (E)-isomer, (Z)-isomer or a mixture thereof. (total 1.102 g, 64%).

[Formula 126]

(E)-isomer: $^1$H NMR (400 MHz, CDCl₃) δ 5.66 (1H, dd, J=1.6, 2.4 Hz, C=CHCO₂Et), 4.14 (2H, q, J=7.0 Hz, CO₂C$\underline{H}_2$CH₃), 2.15-2.10 (5H, m, CH=C(C$\underline{H}_3$)C$\underline{H}_2$), 1.51-1.43 (2H, m, CH₂CH₂CH₂C$\underline{H}_2$CH₃), 1.33-1.23 (7H, m, CO₂CH₂C$\underline{H}_3$& CH₂C$\underline{H}_2$C$\underline{H}_2$CH₂CH₃), 0.89 {3H, t, J=7.0 Hz, (CH₂)₄C$\underline{H}_3$}.

(Z)-isomer: $^1$H NMR (400 MHz, CDCl₃) δ 5.64 (1H, d, J=1.4 Hz, C=C$\underline{H}$CO₂Et), 4.14 (2H, q, J=7.3 Hz, CO₂C$\underline{H}_2$CH₃), 2.61 (2H, t, J=7.8 Hz, CH=C(CH₃)C$\underline{H}_2$), 1.88 (3H, d, J=1.4 Hz, CH=C(C$\underline{H}_3$)CH₂), 1.50-1.42 {2H, m, CH₂CH₂CH₂C$\underline{H}_2$CH₃}, 1.34-1.23 (7H, m, CO₂CH₂C$\underline{H}_3$& CH₂C$\underline{H}_2$C$\underline{H}_2$CH₂CH₃), 0.89 (3H, t, J=7.3 Hz, (CH₂)₄C$\underline{H}_3$).

DIBAL (1.0 M in hexane, 30 ml, 30 mmol) was added dropwise to a solution of Compound (E)-57 (1.030 g, 5.589 mmol) in toluene (70 ml) under Ar at −85° C., and the mixture was stirred at −65° C. for 2 hours. A 1 M aqueous HCl solution was added slowly to the reaction solution, and the mixture was allowed to warm to room temperature with stirring for 10 minutes. The organic layer was then separated, and was extracted with EtOAc twice. The combined organic layer was washed with a saturated aqueous NaCl solution, and was dried over Na₂SO₄. After evaporation of the solvent, the residue was purified by column chromatography on silica gel (Hexane:EtOAc=1:1) to yield allyl alcohol (E)-58 (0.738 g, 64%).

[Formula 127]

$^1$H-NMR (400 MHz, CDCl₃) δ 5.40 (1H, dt, J=1.1, 7.0 Hz, C$\underline{H}$=C), 4.15 (2H, d, J=7.0 Hz, C$\underline{H}_2$OH), 2.01 (2H, t, J=7.7 Hz, CH=C(CH₃)C$\underline{H}_2$), 1.67 (3H, s, CH=C(C$\underline{H}_3$)CH₂), 1.45-1.38 (2H, m, CH₂CH₂CH₂C$\underline{H}_2$CH₃), 1.36-1.21 (5H, m, CH₂O$\underline{H}$ & CH₂C$\underline{H}_2$C$\underline{H}_2$CH₂CH₃), 0.89 (3H, t, J=7.0 Hz, (CH₂)₄C$\underline{H}_3$).

Ph₃P (3.067 g, 11.69 mmol) and CBr₄ (3.788 g, 11.42 mmol) were added to a solution of allyl alcohol (E)-58

(0.738 g, 5.19 mmol) in CHCl$_3$ (30 ml) at 0° C., and the mixture was stirred for one hour. H$_2$O was added to the reaction solution, and the organic layer was separated followed by extraction of the aqueous layer with EtOAc twice. The combined organic layer was washed with saturated saline, and was dried over Na$_2$SO$_4$. After evaporation of the solvent, the residue was purified by column chromatography on silica gel (Hexane:EtOAc=4:1) to yield the corresponding bromide (1.20 g). The bromide was used directly in the next reaction without further purification.

That is, KOH (0.99 M in MeOH, 16.0 ml, 15.8 mmol) was added to a solution of Compound 112 (2.121 g, 11.37 mmol) in MeOH (4.0 ml), and the mixture was cooled to 0° C. CaCl$_2$.2H$_2$O (1.176 g, 7.999 mmol) and a solution of the bromide (crude, 1.20 g) in MeOH (10 ml) were added to this cooled mixture, which was stirred at room temperature for 15 hours. The reaction solution was filtered through celite, and the filtrate was then concentrated. The residue was diluted with EtOAc and poured into a 0.1 M aqueous KOH solution. The organic layer was separated, and the aqueous layer was extracted with Et$_2$O and EtOAc. The combined organic layer was washed with saturated brine, and was dried over Na$_2$SO$_4$. After evaporation of the solvent, the residue was purified by column chromatography on silica gel (Hexane:EtOAc=2:1), followed by recrystallization from mixed solvent of hexane and CHCl$_3$ (5:1) twice to yield target product 264-8 (0.371 g, 23%).

[Formula 128]

Mp 99-101° C.

$^1$H-NMR (400 MHz, CDCl$_3$) δ 12.70 (1H, s, Ar—OH), 10.14 (1H, s, Ar—CHO), 6.42 (1H, s, Ar—OH), 5.21 (1H, tq, J=1.1, 7.0 Hz, CH=C), 3.40 (2H, d, J=7.0 Hz, Ar—CH$_2$), 2.60 (3H, s, Ar—CH$_3$), 1.96 {2H, t, J=7.5 Hz, CH=C(CH$_3$)CH$_2$}, 1.78 {3H, s, CH=C(CH$_3$)CH$_2$}, 1.41-1.34 {2H, m, CH$_2$(CH$_2$)$_2$CH$_2$CH$_3$}, 1.31-1.18 {4H, m, CH$_2$(CH$_2$)$_2$CH$_2$CH$_3$}, 0.86 {3H, t, J=7.1 Hz, CH$_2$(CH$_2$)$_3$CH$_3$}.

IR (KBr) 3341, 2922, 2860, 1620, 1525, 1464, 1421, 1373, 1330, 1279, 1234, 1165, 1111, 955, 907, 876, 787, 715, 625, 592, 561 cm$^{-1}$.

Anal. Found: C, 65.43; H, 7.44; Cl, 11.43%. Calcd for C$_{17}$H$_{23}$ClO$_3$: C, 65.69; H, 7.46; Cl, 11.41%.

In addition, the aqueous layer was acidified with a 2 M aqueous HCl solution, and was extracted with EtOAc to recover unreacted Compound 112.

3-Chloro-4,6-dihydroxy-2-methyl-5-(3-methyloctyl)benzaldehyde (Compound 265-8)

Pd—C (a catalytic amount) was added to a solution of Compound 264-8 (0.185 g, 0.595 mmol) in EtOH (10 ml) at 0° C., and the mixture was stirred under H$_2$ atmosphere at 0° C. for 2 hours and at room temperature for 3 hours. The Pd—C was filtered out, and the solvent was then evaporated. The residue was purified by column chromatography on silica gel (Hexane:EtOAc=12:1), followed by recrystallization from hexane twice to yield target product 265-8 (0.071 g, 38%).

[Formula 129]

Mp 65-67° C.

$^1$H-NMR (400 MHz, CDCl$_3$) δ 12.65 (1H, s, Ar—OH), 10.14 (1H, s, Ar—CHO), 6.30 (1H, s, Ar—OH), 2.69-2.64 (2H, m, Ar—CH$_2$), 2.60 (3H, s, Ar—CH$_3$), 1.53-1.41 (2H, m, CH$_2$), 1.38-1.20 {8H, m, (CH$_2$)$_4$}, 1.19-1.10 (1H, m, CHCH$_3$), 0.95 {3H, d, J=6.6 Hz, CH(CH$_3$)CH$_2$}, 0.88 {3H, t, J=7.0 Hz, CH$_2$(CH$_2$)$_3$CH$_3$}.

IR (KBr) 3258, 2922, 2860, 1603, 1464, 1418, 1373, 1290, 1240, 1128, 924, 799, 764, 708, 631, 592, 530 cm$^{-1}$.

HRMS (EI) Found: 312.1479. Calcd for C$_{17}$H$_{25}$ClO$_3$: 312.1492.

(Z)-3-Chloro-4,6-dihydroxy-2-methyl-5-(3-methyl-2-octenyl)benzaldehyde (Compound (Z)-264-8)

The target product was obtained from Compound (Z)-57 in a similar manner.

[Formula 130]

Mp 157-158° C.

$^1$H-NMR (400 MHz, CDCl$_3$) δ 12.69 (1H, s, Ar—OH), 10.14 (1H, s, Ar—CHO), 6.42 (1H, br, Ar—OH), 5.23 (1H, t, J=7.3 Hz, CH=C), 3.40 (2H, d, J=7.3 Hz, Ar—CH$_2$), 2.60 (3H, s, Ar—CH$_3$), 2.21 (2H, t, J=7.5 Hz, CH=C(CH$_3$)CH$_2$), 1.68 (3H, s, CH=C(CH$_3$)CH$_2$), 1.47-1.39 (2H, m, CH$_2$(CH$_2$)$_2$CH$_2$CH$_3$), 1.37-1.30 (4H, m, CH$_2$(CH$_2$)$_2$CH$_2$CH$_3$), 0.91 (3H, t, J=6.8 Hz, CH$_2$(CH$_2$)$_3$CH$_3$).

IR (KBr) 3279, 2964, 2916, 2860, 1616, 1516, 1452, 1421, 1373, 1334, 1279, 1231, 1192, 1157, 1109, 959, 899, 868, 787, 718, 621, 592, 527 cm$^{-1}$.

HRMS (EI) Found: 310.1337. Calcd for C$_{17}$H$_{23}$ClO$_3$: 310.1336.

(E/Z)-3-Chloro-4,6-dihydroxy-2-methyl-5-(3-methyl-2-octenyl)acetophenone (Compound 268-8)

The target product was obtained from an alcohol (Compound 58, (E)/(Z) mixture) in a similar manner.

[Formula 131]

(E): (Z)=5:1.

Mp 42-46° C.

$^1$H NMR (400 MHz, CDCl$_3$) δ 12.55 {⅙H, s, Ar—OH, (Z)}, 12.53 {⅚H, s, Ar—OH, (E)}, 6.25 (1H, s, Ar—OH), 5.21 (1H, t, J=6.8 Hz, CH=C), 3.41 (2H, d, J=6.8 Hz, Ar—CH$_2$), 2.60 (3H, s, Ar—CH$_3$), 2.58 (3H, s, CH$_3$C=O), 2.21 {⅓H, t, J=7.5 Hz, CH=C(CH$_3$)CH$_2$, (Z)}, 1.96 {5/3H, t, J=7.7 Hz, CH=C(CH$_3$)CH$_2$, (E)}, 1.77 {5/2H, s, CH=C(CH$_3$)CH$_2$, (E)}, 1.68 {½H, s, CH=C(CH$_3$)CH$_2$, (Z)}, 1.41-1.18 {6H, m, CH$_2$(CH$_2$)$_3$CH$_3$}, 0.91 (½H, t, J=7.0 Hz, CH$_2$(CH$_2$)$_3$CH$_3$, (4), 0.86 {5/2H, t, J=7.1 Hz, CH$_2$(CH$_2$)$_3$CH$_3$, (E)}.

(E)-3-Chloro-6-hydroxy-2-methyl-(3-methyl-2-octenoxy)acetophenone (Compound 270-8).

Compound 270-8 was obtained as a by-product of Compound 268-8.

[Formula 132]

$^1$H-NMR (400 MHz, CDCl$_3$) δ 12.65 (1H, s, Ar—OH), 6.38 (1H, s, Ar—H), 5.46 (1H, t, J=6.2 Hz, CH=C), 4.63 (2H, d, J=6.2 Hz, ArOCH$_2$), 2.61 (3H, s, Ar—CH$_3$), 2.57 (3H, s, CH$_3$C=O), 2.06 {2H, t, J=7.5 Hz, CH=C(CH$_3$)CH$_2$}, 1.73 {3H, s, CH=C(CH$_3$)CH$_2$}, 1.43 {2H, m, (CH$_2$)$_3$CH$_2$CH$_3$}, 1.34-1.23 {4H, m, CH$_2$(CH$_2$)$_2$CH$_2$CH$_3$}, 0.88 {3H, t, J=7.0 Hz, CH$_2$(CH$_2$)$_3$CH$_3$}.

IR (KBr) 2978, 2916, 1607, 1460, 1408, 1360, 1273, 1249, 1202, 1094, 1040, 1011, 824, 752, 638, 625 cm$^{-1}$.

3-Chloro-4,6-dihydroxy-2-methyl-5-(3-methyloctyl)acetophenone (Compound 269-8)

[Formula 133]

$^1$H NMR (400 MHz, CDCl$_3$) δ 12.53 (1H, s, Ar—OH), 6.08 (1H, s, Ar—OH), 2.64-2.56 (2H, m, Ar—CH$_2$), 2.53 (3H, s, Ar—CH$_3$), 2.51 (3H, s, CH$_3$C=O), 1.48-1.35 (2H, m, CH$_2$), 1.33-1.13 {8H, m, (CH$_2$)$_4$}, 1.12-1.03 (1H, m, CHCH$_3$), 0.87 {3H, d, J=6.8 Hz, CH(CH$_3$)CH$_2$}, 0.81 {3H, t, J=7.0 Hz, CH$_2$(CH$_2$)$_3$CH$_3$}.

$^{13}$C-NMR (100 MHz, CDCl$_3$) δ 204.58, 160.76, 153.88, 134.47, 117.14, 116.16, 113.86, 36.81, 35.57, 33.08, 32.85, 32.27, 26.64, 22.72, 21.25, 20.76, 19.61, 14.23.

IR (KBr) 3391, 2922, 2860, 1610, 1468, 1404, 1356, 1269, 1192, 1119, 1092, 997, 951, 868, 785, 742, 603 cm$^{-1}$.

HRMS (EI) Found: 326.1659. Calcd. for C$_{18}$H$_{27}$ClO$_3$: 326.1649.

18. Compound 206-12-Opiv

Scheme 18.

[Formula 134]

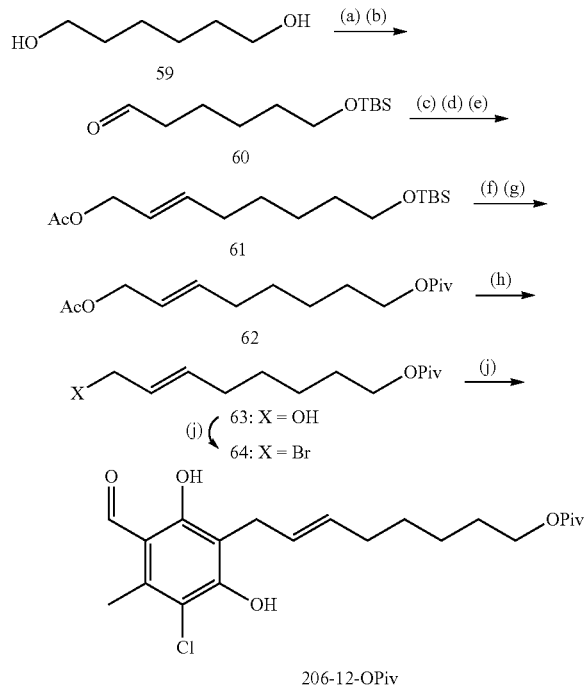

206-12-OPiv

Reagents & conditions: (a) TBS—Cl, imidazole, DMAP, DMF (b) Swen Oxidation
(c) (EtO)$_2$P(O)CH$_2$CO$_2$Et, MeLi, THF (d) DIBAL, toluene (e) Ac$_2$O, pyridine
(f) TBAF, THF (g) Piv-Cl, Et$_3$N, DMAP, CHCl$_3$
(h) (NH$_2$)$_2$C=NH HCl, NaOMe, MeOH/CHCl$_3$ (i) CBr$_4$, Ph$_3$P, CHCl$_3$
(j) 112, KOH, CaCl$_2$, MeOH.

(E)-8-(3-Chloro-5-formyl-2,6-dihydroxy-4-methylphenyl)-6-octenyl pivalate (Compound 206-12-OPiv)

Imidazole (1.724 g, 25.32 mmol), DMAP (a catalytic amount), and TBS-Cl (50% in toluene, 3.50 ml, 10.1 mmol) were added to a solution of 1,6-hexanediol (Compound 59, 3.369 g, 28.51 mmol) in DMF (30 ml) at 0° C., and the mixture was allowed to warm to room temperature with stirring for 15 hours. H$_2$O was added to the reaction solution, the organic layer was then separated, and the aqueous layer was extracted with Et$_2$O twice. The combined organic layer was washed with a saturated aqueous NaHCO$_3$ solution then with a saturated aqueous NaCl solution, and was dried over Na$_2$SO$_4$. After evaporation of the solvent, the residue was purified by column chromatography on silica gel (Hexane:EtOAc=3:1) to yield the corresponding silyl ether (1.671 g, 71%).

[Formula 135]

$^1$H-NMR (400 MHz, CDCl$_3$) δ 3.66-3.59 (4H, m, CH$_2$OH & CH$_2$OTBS), 1.60-1.51 (4H, m, CH$_2$CH$_2$OH & CH$_2$CH$_2$OTBS), 1.43-1.36 (5H, m, CH$_2$CH$_2$ & OH), 0.89 {9H, s, C(CH$_3$)$_3$}, 0.05 {6H, s, Si(CH$_3$)$_2$}.

DMSO (2.2 ml, 31 mmol) was added dropwise to a solution of oxalyl chloride (1.25 ml, 14.6 mmol) in CHCl$_3$ (50 ml) at −60° C., and the mixture was stirred for 10 minutes. A solution of the alcohol (1.671 g, 7.189 mmol) in CHCl$_3$ (15 ml) was added dropwise to this mixture, which was stirred at the same temperature for 2 hours. Et$_3$N (6.0 ml, 43 mmol) was further added dropwise to the mixture, which was stirred at the same temperature for one hour. Then, addition of H$_2$O quenched the reaction. The organic layer was separated, and the aqueous layer was then extracted with Et$_2$O twice. The combined organic layer was washed with a saturated aqueous NH$_4$Cl solution then with a saturated aqueous NaCl solution, and was dried over Na$_2$SO$_4$. After evaporation of the solvent, the residue was purified by column chromatography on silica gel (Hexane:EtOAc=4:1) to yield aldehyde 60 (1.400 g, 85%).

MeLi (1.60 M in Et2O, 6.5 ml, 10.4 mmol) was added dropwise to a solution of ethyl diethylphosphonoacetate (1.8 ml, 9.1 mmol) in THF (50 ml) at −15° C., and the mixture was allowed to warm to room temperature with stirring over one hour. The mixture was again cooled to −15° C., and a solution of Compound 60 (1.460 g, 6.336 mmol) in THF (10 ml) was added dropwise to the cooled mixture, which was allowed to warm to room temperature with stirring for 20 hours. H$_2$O was added to the reaction solution, the organic layer was then separated, and the aqueous layer was extracted with EtOAc twice. The combined organic layer was washed with a saturated aqueous NaHCO$_3$ solution then with a saturated aqueous NaCl solution, and was dried over Na$_2$SO$_4$. After evaporation of the solvent, the residue was purified by column chromatography on silica gel (Hexane:EtOAc=15:1) to yield the corresponding unsaturated ester (1.305 g, 69%).

DIBAL (1.0 M in hexane, 22 ml, 22 mmol) was added dropwise to a solution of this unsaturated ester (1.305 g, 4.343 mmol) in toluene (50 ml) at −80° C., and the mixture was allowed to warm to −65° C. with stirring for 3 hours. H$_2$O was added to the reaction solution, the organic layer was then separated, and the aqueous layer was extracted with Et$_2$O. The combined organic layer was washed with a 2 M aqueous HCl solution then with a saturated aqueous NaCl solution, and was dried over Na2SO$_4$. After evaporation of the solvent, the residue was subjected to column chromatography on silica gel (Hexane:EtOAc=3:1) to yield the corresponding allyl alcohol. This allyl alcohol was used directly in the next reaction without further purification.

The entire allyl alcohol obtained was dissolved in pyridine (10 ml), and Ac$_2$O (5 ml) was added to the solution at room temperature followed by stirring for 16 hours. The reaction solution was diluted with EtOAc, and then poured into H$_2$O. The organic layer was separated, and the aqueous layer was then extracted with EtOAc. The combined organic layer was washed with a 2 M aqueous HCl solution twice, with a saturated aqueous NaCO$_3$ solution once, then with a saturated aqueous NaCl solution once, and was dried over Na$_2$SO$_4$. After evaporation of the solvent, the residue was purified by column chromatography on silica gel (Hexane:EtOAc=7:1) to yield acetate 61 (1.178 g, 90% for 2 steps).

[Formula 136]

$^1$H-NMR (400 MHz, CDCl$_3$) δ 5.77 (1H, dt, J=6.6, 15.4 Hz, AcOCH$_2$CH=CH), 5.56 (1H, dt, J=6.6, 15.4 Hz, AcOCH$_2$CH=CH), 4.50 (2H, d, J=6.2 Hz, AcOCH$_2$CH=CH), 3.60 (2H, t, J=6.6 Hz, CH$_2$OTBS), 2.06 (5H, br, CH$_3$C=O & CH=CHCH$_2$), 1.55-1.48 (2H, m, C

H̲CH₂OTBS), 1.44-1.30 (4H, m, 2×CH̲₂), 0.89 {9H, s, C(CH̲₃)₃}, 0.05 {6H, s, Si(CH̲₃)₂}.

TBAF (1.0 M in THF, 4.2 ml, 4.2 mmol) was added to a solution of Compound 61 (1.178 g, 3.919 mmol) in THF (15 ml) at room temperature, and the mixture was stirred for 18 hours. H₂O was added to the reaction solution, the organic layer was then separated, and the aqueous layer was extracted with EtOAc twice. The combined organic layer was washed with a saturated aqueous NaCl solution, and was dried over Na₂SO₄. After evaporation of the solvent, the residue was purified by column chromatography on silica gel (Hexane:EtOAc=3:1 to 1:1) to yield the corresponding primary alcohol (0.640 g, 88%).

Et₃N (0.55 ml, 3.9 mmol), Piv-Cl (0.50 ml, 4.1 mmol), and DMAP (a catalytic amount) were added to a solution of this primary alcohol (0.640 g, 3.436 mmol) in CH₃Cl (15 ml) at 0° C., and the mixture was allowed to warm to room temperature with stirring for 20 hours. H₂O was added to the reaction solution, the organic layer was then separated, and the aqueous layer was extracted with EtOAc twice. The combined organic layer was washed with a saturated aqueous NaCl solution, and was dried over Na₂SO₄. After evaporation of the solvent, the residue was purified by column chromatography on silica gel (Hexane:EtOAc=5:1) to yield the corresponding pivalate (Compound 62) (0.359 g, 39%).

Guanidine hydrochloride (0.151 g, 1.58 mmol) and NaOMe (19 mg, 0.35 mmol) were added to a mixed solvent of MeOH (13.5 ml) and CHCl₃ (1.5 ml) under Ar at room temperature, and the mixture was stirred for 10 minutes. This solution was added dropwise to a mixed solution of the pivalate (0.359 g, 1.33 mmol) in MeOH (4.5 ml) and CHCl₃ (0.5 ml), and the mixture was stirred at room temperature for 5 hours. After evaporation of the solvent, EtOAc and H₂O were added to the residue, and the organic layer was separated. The aqueous layer was extracted with EtOAc, and the combined organic layer was washed with a saturated aqueous NaCl solution, and was dried over Na₂SO₄. After evaporation of the solvent, the residue was purified by column chromatography on silica gel (Hexane:EtOAc=2:1) to yield corresponding allyl alcohol 63 (0.294 g, 97%).

Ph₃P (0.756 g, 2.88 mmol) and CBr₄ (0.965 g, 2.91 mmol) were added to a solution of this allyl alcohol 63 (0.294 g, 1.288 mmol) in CHCl₃ (20 ml) at 0° C., and the mixture was stirred at the same temperature for 1.5 hours. After evaporation of the solvent, the residue was subjected to column chromatography on silica gel (Hexane:EtOAc=2:1) to yield corresponding bromide 64. This bromide was used directly in the next reaction without further purification.

That is, KOH (1.0 M in MeOH, 3.5 ml, 3.5 mmol) was added to a solution of Compound 112 (0.419 g, 2.25 mmol) in MeOH (3.0 ml), and the mixture was cooled to 0° C. A solution of the bromide (crude 64) above in MeOH (3.0 ml) and CaCl₂.2H₂O (0.294 g, 2.00 mmol) were added to this cooled mixture, which was allowed to warm to room temperature with stirring for 18 hours. The reaction solution was diluted with Et₂O, the organic layer was then separated, and the aqueous layer was extracted with Et₂O once then with EtOAc once. The combined organic layer was washed with a 0.1 M aqueous KOH solution then with a saturated aqueous NaCl solution, and was dried over Na₂SO4. After evaporation of the solvent, the residue was purified by column chromatography on silica gel (Hexane:EtOAc=4:1), followed by further purification through recrystallization from hexane to yield target product 206-12-OPiv (35 mg 7% for 2 steps).

[Formula 137]

Mp 89-90° C.

¹H-NMR (400 MHz, CDCl₃) δ 12.68 (1H, s, Ar—OH̲), 10.15 (1H, s, CH̲O), 6.38 (1H, br, Ar—OH̲), 5.54-5.51 (2H, m, CH̲=CH), 4.02 (2H, t, J=6.6 Hz, CH̲₂OPiv), 3.38 (2H, d, J=4.0 Hz, ArCH̲₂CH=CH), 2.61 (3H, s, Ar—CH̲₃), 2.03-1.95 (2H, m, CH̲₂), 1.63-1.57 (2H, m, CH̲₂), 1.40-1.29 {4H, m, (CH̲₂)₂}, 1.18 {9H, s, C(CH̲₃)₃}.

IR (KBr), 3300, 2970, 2916, 1724, 1620, 1481, 1452, 1429, 1286, 1248, 1223, 1175, 1123, 980, 895, 787, 592 cm⁻¹.

HRMS (EI) Found: 396.1684. Calcd. for C₂₁H₂₉ClO₅: 396.1704.

19. Compounds 278-8 and 279-8

Scheme 19.

[Formula 138]

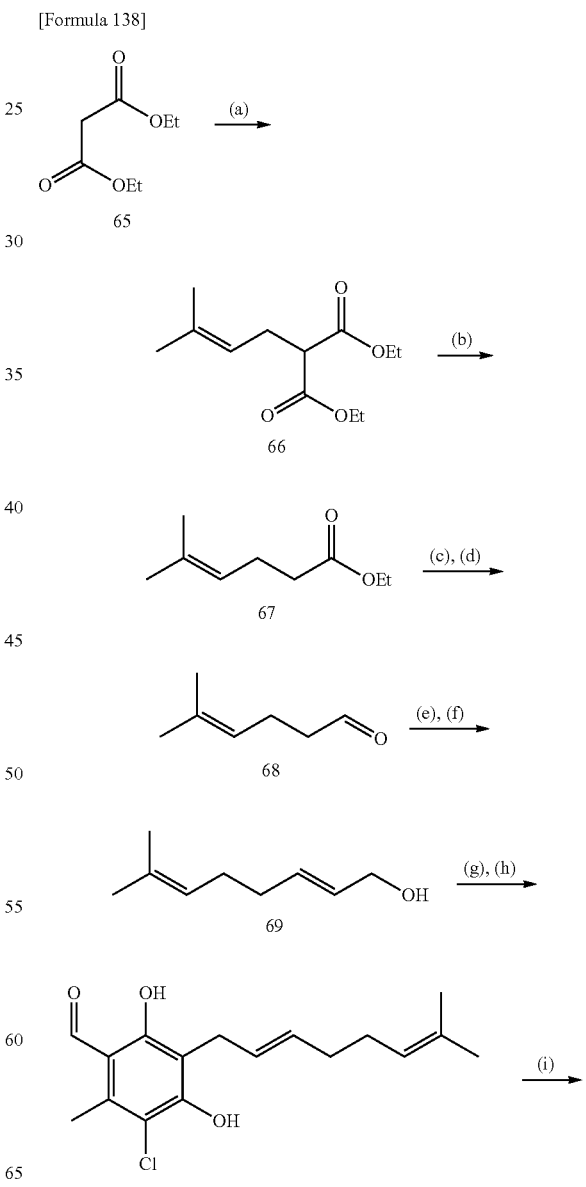

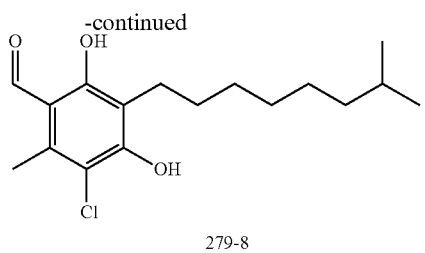

279-8

Reagents & conditions: (a) Prenyl bromide, NaH, toluene (b) DMSO, NaCl, H₂O (c) LAH, THF (d) Swern ox. (e) (EtO)₂P(O)CH₂CO₂Et, NaH, THF (f) DIBAL, toluene (g) CBr₄, (ⁿC₈H₁₇)₃P, Et₂O (h) 112, KOH, CaCl₂, MeOH, (i) H₂, Pd—C, EtOAc.

(E)-3-Chloro-4,6-dihydroxy-2-methyl-5-(7-methyl-2,6-octadienyl)benzaldehyde (Compound 278-8)

Diethyl malonate 65 was prenylated to yield Compound 66 according to the conventional method (Tetrahedron, 2003, 59, 2991-2998) (84% yield). A solution of Compound 66 (10.00 g, 43.8 mmol) in DMSO (60 ml) was then added to a mixture of NaCl (4.10 g, 70.1 mmol) and water (3.5 ml), and the reaction mixture was stirred at 150° C. for 18 hours. The mixture was cooled to room temperature, and was extracted with ethyl acetate, and the extract was dried over Na₂SO₄. The crude product obtained by concentration under reduced pressure was subjected to column chromatography on silica gel (Hexane:EtOAc=20:1) to yield corresponding monoester 67 (5.69 g, 83% yield).

A solution of this monoester 67 (2.30 g, 14.7 mmol) in THF (30 ml) was added to a suspension of lithium aluminium hydride (528 mg, 12.8 mmol) in THF (30 ml) at 0° C., and the mixture was stirred for 10 minutes. Ice (30 g) and 1 M hydrochloric acid (30 ml) were added to the mixture, followed by extraction with ethyl acetate. The extract was dried over Na₂SO₄. Concentration of the extract under reduced pressure gave an alcohol product (1.39 g, 83% yield). This alcohol product was oxidized to the corresponding aldehyde 68 as in (b) in Scheme 18 (51% yield).

Aldehyde 68 was converted to alcohol 69 of which the chain is extended by two-carbon atoms as in (c) and (d) in Scheme 18 (54% yield for 2 steps).

Alcohol 69 was converted to the corresponding bromide as in (f) and (g) in Scheme 13, followed by a reaction with Compound 112 to yield target product 278-8 (20% yield for 2 steps).

[Formula 139]

Mp 131-132° C.

¹H-NMR (400 MHz, CDCl₃) δ 12.69 (1H, s, Ar—O$\underline{H}$), 10.15 (1H, s, Ar—C$\underline{H}$O), 6.37 (1H, s, Ar—O$\underline{H}$), 5.55 (2H, m, C$\underline{H}$=C$\underline{H}$), 5.08 {1H, t, J=1.3 Hz, C$\underline{H}$=C(CH₃)₂}, 3.38 (2H, d, J=3.7 Hz, Ar—C$\underline{H}_2$), 2.61 (3H, s, Ar—C$\underline{H}_3$), 2.01 (4H, br, C$\underline{H}_2$C$\underline{H}_2$), 1.66 (3H, s, C$\underline{H}_3$), 1.57 (3H, s, C$\underline{H}_3$).

IR (KBr) 3433, 2908, 1624, 1425, 1219, 1111, 781, 529.

HRMS (EI) Found: 308.1169. Calcd. for C₁₇H₂₁ClO₃: 308.1179.

3-Chloro-4,6-dihydroxy-2-methyl-5-(7-methyloctyl)benzaldehyde (Compound 279-8)

Reduction of Compound 278-8 was conducted as in synthesis of 265-8 (f) in Scheme 17 to yield Compound 279-8 (97% yield).

[Formula 140]

Mp 93-94° C.

¹H-NMR (400 MHz, CDCl₃) δ 12.65 (1H, s, Ar—O$\underline{H}$), 10.14 (1H, s, Ar—C$\underline{H}$O), 6.30 (1H, s, Ar—O$\underline{H}$), 2.66 (2H, d, J=7.6 Hz, Ar—C$\underline{H}_2$), 2.61 (3H, s, Ar—C$\underline{H}_3$), 1.60-1.46 {3H, m, C$\underline{H}$(CH₃)₂ & C$\underline{H}_2$}, 1.40-1.23 {6H, m, (C$\underline{H}_2$)₃}, 1.18-1.11 (2H, m, C$\underline{H}_2$), 0.85 {6H, d, J=6.8 Hz, CH(C$\underline{H}_3$)₂}.

IR (KBr) 3260, 2916, 2847, 1607, 1470, 1421, 1248, 1132, 871, 762, 710, 596, 529 cm⁻¹.

HRMS (EI) Found: 312.1484. Calcd. for C₁₇H₂₅ClO₃: 312.1492.

20. Compounds 278-12-OPiv, and 279-12-Opiv

Scheme 20

[Formula 141]

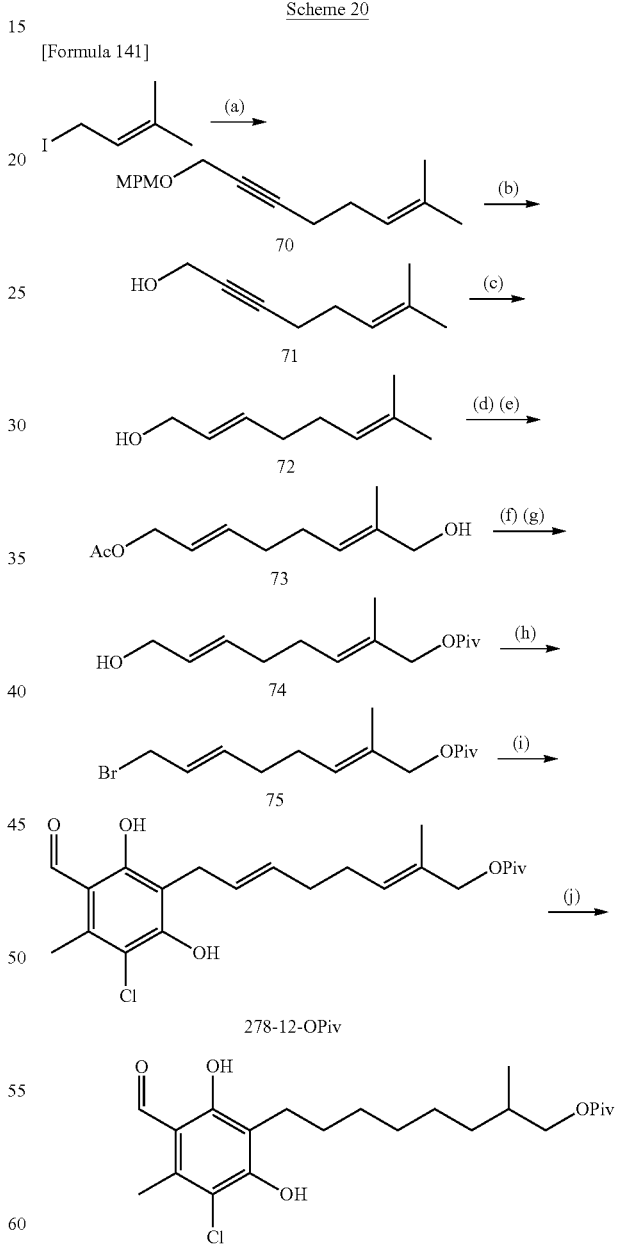

278-12-OPiv 279-12-OPiv (a) MPM-OCH₂CCH, BuLi, THF/DMPU; (b) DDQ, CHCl₃/H₂O; (c) RedAl, THF; (d) Ac₂O, Et₃N, DMAP; (e) SeO₂, TBHP, 4-hydroxybenzoic acid, CHCl₃; (f) pivaloyl chloride, pyridine, DMAP, CHCl₃; (g) HN=C(NH₂)₂HCl, NaOMe, MeOH/CHCl₃; (h) CBr₄, (octyl)₃P, Et₂O; (i) 112, KOH/CaCl₂, MeOH; (j) H₂, Pd/C, EtOAc.

(2E,6E)-8-(3-Chloro-5-formyl-2,6-dihydroxy-4-methylphenyl)-2-methyl-2,6-octadienyl pivalate (Compound 278-12-OPiv)

A solution of prenyl iodide (220 mg, 1.05 mmol) in DMPU (1.5 ml), which was prepared by treating cyclohexyl methyl ketone by the method described in the document (Synthesis, 1979, 37-38), was added at −20° C. to a reaction mixture prepared by adding a solution of butyl lithium (2.00 mmol, 1.2 ml) in hexane to a solution of 3-(4-methoxybenzyloxy)-1-propyne (282 mg, 1.50 mmol) in THF (1 ml) at −20° C. followed by stirring for 2 hours, and the mixture was allowed to warm to room temperature with stirring for 12 hours. The product extracted with ethyl acetate, and the extract after posttreatment was purified by column chromatography on silica gel (Hexane:EtOAc=25:1) to yield MPM ether product 70 (203 mg, 40% yield). The MPM ether product 70 was converted to 71 by removing its alcohol protecting group in accordance with the conventional method (J. Am. Chem. Soc., 2002, 13670-13671) using 2,3-dichloro-5,6-dicyanobenzoquinone. Subsequently, reduction with Red-Al (Org. Lett., 2004, 1785-1787) was applied to 71 to afford (E)-7-methylocta-2,6-dien-1-ol (72) (88% yield for 2 steps).

Triethyl amine (1.86 g, 18.3 mmol), acetic anhydride (1.57 g, 15.2 mmol), and dimethylaminopyridine (80 mg, 0.61 mmol) were added to a solution of alcohol 72 (855 mg, 6.10 mmol) in chloroform (20 ml), and the mixture was stirred at room temperature for 16 hours. Following the workup through extraction, the mixture was purified by column chromatography on silica gel (Hexane:EtOAc=9:1), to yield an ester of which the hydroxy group was acetylated (1082 mg, 97% yield). The resulting ester was oxidized by the method using selenium dioxide catalyst (Tetrahedron Lett., 2001, 42, 2205-2208) to yield Compound 73 (44% yield).

Compound 73 was converted to diester (91% yield) as in synthesis (c) in Scheme 15. To hydrolyze only acetate ester of two types of ester bond, synthesis (d) in Scheme 15 was used to afford target monoester 74 (86% yield).

Monoester 74 was converted to bromide 75 as in synthesis (e) in Scheme 15. Bromide 75 was allowed to react with aromatic ring moiety 112 as in synthesis (f) in Scheme 15, resulting in Compound 278-12-OPiv (25% yield for 2 steps).

[Formula 142]
Mp 90-91° C.
$^1$H-NMR (400 MHz, CDCl$_3$) δ 12.69 (1H, s, Ar—OH), 10.15 (1H, s, Ar—CHO), 6.44 (1H, s, Ar—OH), 5.55-5.51 (2H, m, CH═CH), 5.40 (1H, m, CH═C(CH$_3$)CH$_2$OPiv), 4.42 (2H, s, CH$_2$OPiv), 3.37 (2H, d, J=4.8 Hz, Ar—CH$_2$), 2.61 (3H, s, Ar—CH$_3$), 2.09-2.04 (4H, m, CH$_2$CH$_2$), 1.60 (3H, s, CH$_3$), 1.21 (9H, s, C(CH$_3$)$_3$).
IR (KBr) 3293, 2972, 1724, 1622, 1622, 1425, 1283, 1227, 1167, 1117, 976, 893, 781, 592 cm$^{-1}$.

8-(3-Chloro-5-formyl-2,6-dihydroxy-4-methylphenyl)-2-methyloctyl pivalate (Compound 279-12-OPiv)

Compound 278-12-OPiv was reduced to Compound 279-12-OPiv (84% yield) as in synthesis (g) in Scheme 15.
[Formula 143]
$^1$H-NMR (400 MHz, CDCl$_3$) δ 12.66 (1H, s, Ar—OH), 10.14 (1H, s, Ar—CHO), 6.36 (1H, br, Ar—OH), 3.94 (1H, dd, J=5.8, 10.6 Hz, CH$_2$OPiv) 3.82 (1H, dd, J=6.6, 10.6 Hz, CH$_2$OPiv) 2.66 (2H, t, J=7.9 Hz, Ar—CH$_2$), 2.61 (3H, s, Ar—CH$_3$), 1.82-1.72 (1H, m, CH), 1.60-1.49 (4H, m, 2×CH$_2$), 1.40-1.28 {6H, br, (CH$_2$)$_3$}, 1.20 {9H, s, C(CH$_3$)$_3$}, 0.91 (3H, d, J=6.6 Hz, CH$_3$).
IR (KBr) 3393, 2961, 2930, 2857, 1724, 1717, 1630, 1460, 1422, 1375, 1288, 1248, 1165, 1128, 1034, 982, 806, 772, 710, 590 cm$^{-1}$.
HRMS (EI) calcd. for C$_{22}$H$_{33}$ClO$_5$ (m/z) 412.2017. found 412.2025.

21. Compounds 287-12-OPiv and 287-12-OCO$^i$Pr

Scheme 21
[Formula 144]

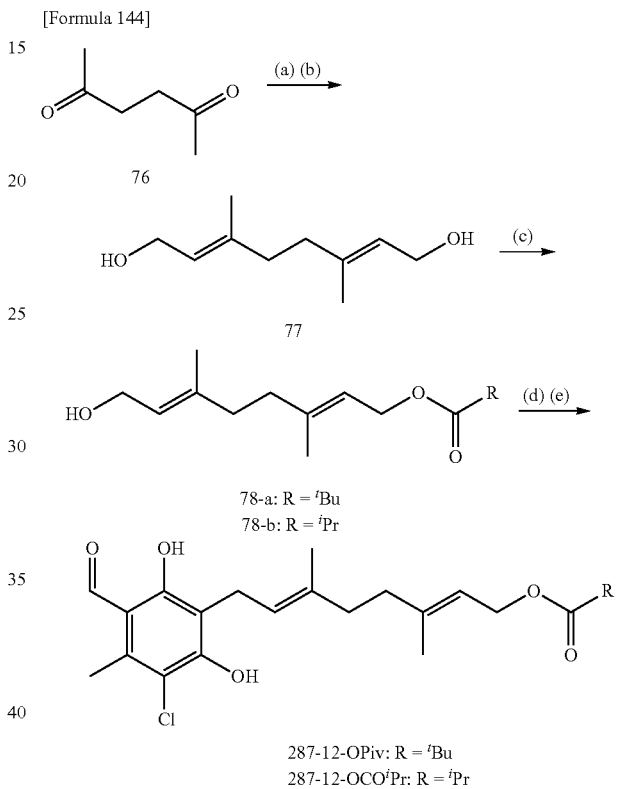

78-a: R = $^t$Bu
78-b: R = $^i$Pr 287-12-OPiv: R = $^t$Bu
287-12-OCO$^i$Pr: R = $^i$Pr

Reagents & conditions: (a) (EtO)$_2$P(O)CH$_2$CO$_2$Et, NaH, THF (b) DIBAL, toluene (c) corresponding acylchloride, Et$_3$N, DMAP, CHCl$_3$ (d) CBr$_4$, ($^n$C$_8$H$_{17}$)$_3$P, Et$_2$O (e) 112, KOH, CaCl$_2$, MeOH.

(2E,6E)-8-(3-Chloro-5-formyl-2,6-dihydroxy-4-methylphenyl)-3,6-dimethyl-2,6-octadienyl pivalate (Compound 287-12-OPiv)

Triethyl phosphonoacetate (3.6 ml, 18 mmol) was added to a suspension of NaH (60% in oil, 0.820 g, 20.5 mmol) in THF (30 ml) at 0° C., and the mixture was allowed to warm to room temperature with stirring for 30 minutes. The reaction solution was again cooled to ° C., and acetonylacetone (Compound 76, 1.0 ml, 8.2 mmol) was added dropwise to the cooled solution. The mixture was allowed to warm to room temperature followed by stirring for 15 hours. Addition of H$_2$O quenched the reaction, and the stirring was continued for 5 minutes. The organic layer was then separated, and the aqueous layer was extracted with EtOAc twice. The combined organic layer was washed with a saturated aqueous NaCl solution, and was dried over Na$_2$SO$_4$. After evaporation of the solvent, the residue was subjected to column chromatography on silica gel (Hexane:

EtOAc=10:1) to separate the corresponding diester into its (E,E)-, (E,Z)-, and (Z,Z)-isomers, and a mixture thereof.

[Formula 145]

(E,E)-isomer; 0.513 g (25% yield).

$^1$H NMR (400 MHz, CDCl$_3$) δ 5.67 (2H, s, 2×C═CHCO$_2$Et), 4.15 (4H, q, J=7.1 Hz, 2×CO$_2$CH$_2$CH$_3$), 2.31 (4H, s, CH$_2$CH$_2$), 2.17 (6H, s, 2×CH═CCH$_3$), 1.28 (6H, t, J=7.1 Hz, ×CO$_2$CH$_2$CH$_3$).

DIBAL (1.0 M in hexane, 12 ml, 12 mmol) was added dropwise to a solution of the diester (0.513 g, 2.017 mmol) in toluene (20 ml) at −70° C., and the mixture was stirred at the same temperature for 3 hours. To the reaction solution was slowly added H$_2$O followed by a 2 M aqueous HCl solution. The mixture was allowed to warm to room temperature with stirring for 10 minutes. The organic layer was separated, and the aqueous layer was extracted with EtOAc twice. The combined organic layer was washed with a saturated aqueous NaHCO$_3$ solution then with a saturated aqueous NaCl solution, and was dried over Na$_2$SO$_4$. After evaporation of the solvent, precipitated crystals were recrystallized from toluene to yield diol (Compound 77) (0.320 g, 93%).

Et$_3$N (0.26 ml, 1.9 mmol), DMAP (cat. amount), and Piv-Cl (0.14 ml, 1.1 mmol) were added to a solution of Compound 77 (0.320 g, 1.88 mol) in CHCl$_3$ (20 ml) at 0° C., and the mixture was allowed to warm to room temperature followed by stirring for 12 hours. A saturated aqueous NaCl solution was added to the reaction solution, the organic layer was separated followed by extraction of the aqueous layer with EtOAc twice. The combined organic layer was dried over Na$_2$SO$_4$. After evaporation of the solvent, the residue was purified by column chromatography on silica gel (Hexane:EtOAc=2:1) to yield the corresponding pivalate (Compound 78-a) (0.163 g, 58%). Unreacted raw material was recovered.

[Formula 146]

$^1$H NMR (400 MHz, CDCl$_3$) δ 5.41 (1H, t, J=7.0 Hz, C═CHCH$_2$OPiv), 5.30 (1H, t, J=7.0 Hz, C═CHCH$_2$OH), 4.56 (2H, d, J=7.0 Hz, CH$_2$OPiv), 4.14 (2H, d, J=7.0 Hz, CH$_2$OH), 2.15 (4H, s, CH$_2$CH$_2$), 1.71 (3H, s, CH$_3$), 1.67 (3H, s, CH$_3$), 1.23 (1H, s, OH), 1.19 {9H, s, C(CH$_3$)$_3$}.

(n-C$_8$H$_{17}$)$_3$P (1.1 ml, 2.5 mmol) and CBr$_4$ (0.853 g, 2.57 mmol) were added to Compound 78-a (0.184 g, 0.723 mmol) in Et$_2$O (15 ml) at 0° C., and the mixture was stirred for 2 hours. The reaction solution was poured into a saturated aqueous NaCl solution, and the organic layer was separated followed by extraction of the aqueous layer with EtOAc. The combined organic layer was dried over Na$_2$SO$_4$. After evaporation of the solvent, the residue was subjected to column chromatography on silica gel (Hexane:EtOAc=7:1) to yield the corresponding bromide. The bromide was used directly in the next reaction without further purification.

CaCl$_2$.2H$_2$O (0.251 g, 1.71 mmol) and a solution of the entire crude bromide above in MeOH (4 ml) was added to a solution of Compound 112 (0.413 g, 2.213 mmol) in KOH (1.0 M in MeOH, 3.3 ml, 3.3 mmol) at 0° C., and the mixture was allowed to warm to room temperature followed by stirring for 14 hours. The reaction solution was diluted with EtOAc, and was filtered through celite. The filtrate was poured into a 0.1 M aqueous KOH solution. The organic layer was separated, and the aqueous layer was then extracted with EtOAc twice. The combined organic layer was washed with a saturated aqueous NaCl solution, and was dried over Na2SO4. After evaporation of the solvent, the residue was purified by column chromatography on silica gel (Hexane:EtOAc=4:1), followed by recrystallization from hexane to yield target product 287-12-OPiv (65 mg, 21% yield for two steps from Compound 78-a).

[Formula 147]

Mp 78-79° C.

$^1$H-NMR (400 MHz, CDCl$_3$) δ 12.69 (1H, s, Ar—OH), 10.14 (1H, s, Ar—CHO), 6.48 (1H, s, Ar—OH), 5.28 (1H, t, J=7.0 Hz, C═CHCH$_2$OPiv), 5.22 (1H, t, J=7.1 Hz, ArCH$_2$CH═C), 4.52 (2H, d, J=7.0 Hz, C═CHCH$_2$OPiv), 3.39 (2H, d, J=7.0 Hz, ArCH$_2$CH═C), 2.61 (3H, s, Ar—CH$_3$), 2.10 (4H, br, CH$_2$CH$_2$), 1.78 (3H, s, CH$_3$), 1.66 (3H, s, CH$_3$), 1.19 {9H, s, C(CH$_3$)$_3$}.

IR (KBr) 3356, 2970, 2932, 1728, 1620, 1526, 1479, 1460, 1424, 1373, 1281, 1231, 1207, 1153, 1113, 1033, 964, 903, 868, 789, 594, 581 cm$^{-1}$.

The aqueous layer was acidified with a 2 M aqueous HCl solution, and was extracted with EtOAc to recover unreacted Compound 112.

(2E,6E)-8-(3-Chloro-5-formyl-2,6-dihydroxy-4-methylphenyl)-3,6-dimethyl-2,6-octadienyl isobutylate (Compound 287-12-OCO$^i$Pr)

[Formula 148]

Mp 62-63° C.

$^1$H-NMR (400 MHz, CDCl$_3$) δ 12.69 (1H, s, Ar—OH), 10.14 (1H, s, Ar—CHO), 6.48 (1H, s, Ar—OH), 5.28 (1H, t, J=6.8 Hz, C═CHCH$_2$O), 5.22 (1H, t, J=7.3 Hz, ArCH$_2$CH═C), 4.53 (2H, d, J=6.8 Hz, C═CHCH$_2$O), 3.39 (2H, d, J=7.3 Hz, ArCH$_2$CH═C), 2.61 (3H, s, Ar—CH$_3$), 2.57-2.50 {1H, m, CH(CH$_3$)$_2$}, 2.10 (4H, br, CH$_2$CH$_2$), 1.78 (3H, s, CH$_3$), 1.66 (3H, s, CH$_3$), 1.16 {6H, d, J=7.3 Hz, CH(CH$_3$)$_2$}.

IR (KBr) 3273, 2974, 2934, 1732, 1620, 1526, 1470, 1452, 1425, 1376, 1283, 1256, 1231, 1209, 1153, 1109, 1065, 961, 889, 791, 716, 629, 586 cm$^{-1}$.

22. Compounds 284-8 and 285-8

Scheme 22

[Formula 149]

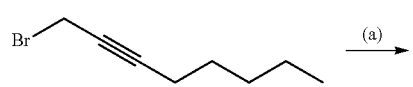

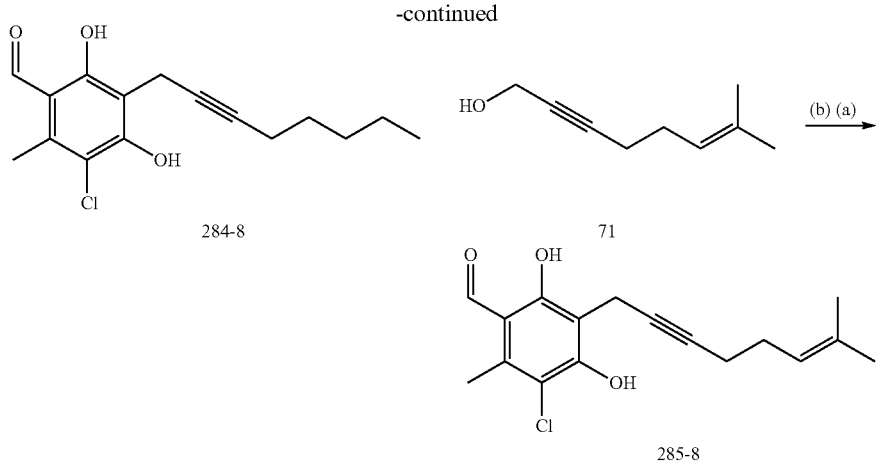

(a) 112, KOH, MgCl$_2$, MeOH; (b) CBr$_4$, (octyl)$_3$P, Et$_2$O

3-Chloro-4,6-dihydroxy-5-(2-octynyl)-2-methylbenzaldehyde (Compound 284-8)

Aromatic ring moiety 112 and commercially available 1-bromo-2-octyne (Compound 79) as raw material were allowed to react as in synthesis (f) in Scheme 15 using magnesium chloride as an additive, resulting in target product 284-8 (21% yield).

[Formula 150]

Mp 135-136° C.

$^1$H-NMR (400 MHz, CDCl$_3$) δ 12.81 (1H, s, Ar—OH), 10.15 (1H, s, Ar—CHO), 7.03 (1H, s, Ar—OH), 3.59 (2H, d, J=2.6 Hz, Ar—CH$_2$), 2.62 (3H, s, Ar—CH$_3$), 2.16-2.13 (2H, m, CCCH$_2$), 1.49 (2H, m, CH$_2$), 1.35-1.25 (4H, m, CH$_2$CH$_2$), 0.88 (3H, t, J=7.0 Hz, CH$_2$CH$_3$).

IR (KBr) 3200, 2963, 2930, 1610, 1460, 1425, 1285, 1227, 1194, 1132, 1119, 887, 759, 713, 637, 584, 536 cm$^{-1}$.

3-Chloro-4,6-dihydroxy-2-methyl-5-(7-methyl-6-octen-2-ynyl)benzaldehyde (Compound 285-8)

Alcohol 71 prepared by Scheme 20 was used as a side-chain raw material to yield target product 285-8 as in (h) and (i) in Scheme 20.

[Formula 151]

Mp 138° C.

$^1$H-NMR (400 MHz, CDCl$_3$) δ 12.81 (1H, s, Ar—OH), 10.15 (1H, s, Ar—CHO), 7.04 (1H, s, Ar—OH), 5.12 {1H, m, CH=C(CH$_3$)$_2$}, 3.59 (2H, s, Ar—CH$_2$), 2.62 (3H, s, Ar—CH$_3$), 2.16 (4H, br, CH$_2$CH$_2$), 1.68 (3H, s, CH$_3$), 1.59 (3H, s, CH$_3$).

IR (KBr) 3198, 2967, 2924, 1618, 1452, 1429, 1285, 1229, 1186, 1113, 893, 791, 588, 538 cm$^{-1}$.

HRMS (EI) calcd. for C$_{17}$H$_{19}$ClO$_3$ (m/z) 306.1023. found 306.1049.

23. Compounds 288-12-Piv and 215-12-Piv

Scheme 23

[Formula 152]

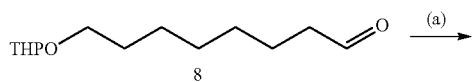

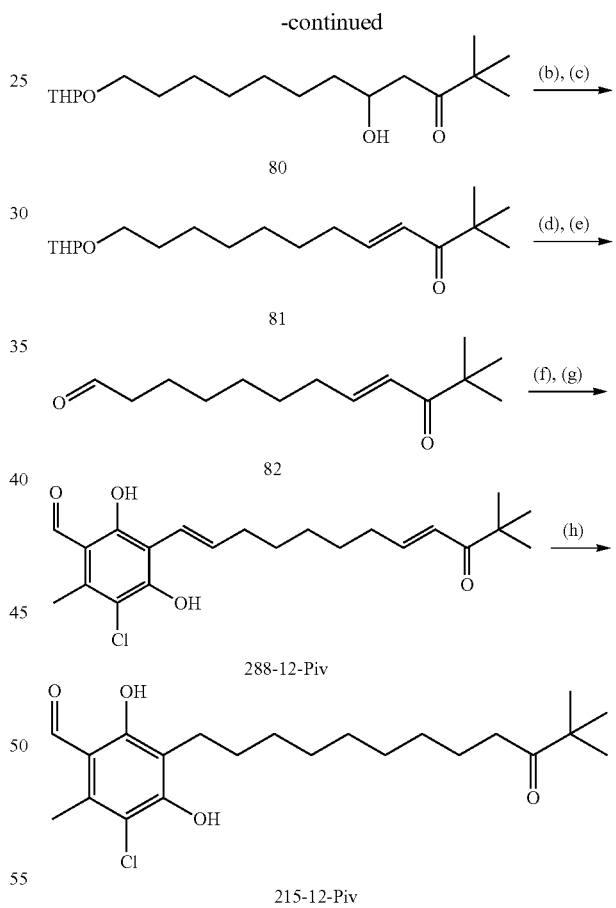

Reagents & conditions: (a) pinacolon, LHMDS, THF (b) Ac$_2$O, DMAP, pyridine (c) DBU, CHCl$_3$ (d) PPTS, EtOH (e) Swernoxidation (f) 112, KOH, CaCl$_2$ 2H$_2$O, MeOH (g) H$_3$PO$_4$, AcOH (h) H$_2$, Pd—C, EtOAc

3-Chloro-4,6-dihydroxy-5-((E,E)-11,11-dimethyl-10-oxo-2,8-dodecadienyl)-2-methylbenzaldehyde (Compound 288-12-Piv)

Aldehyde 8 was allowed to react with 3,3-dimethyl-2-butanone to yield adduct 80 (59% yield) by the known method described in the document (K. Mori and S. Takechi, Tetrahedron, 1985, 41, 3049-3062).

Then, acetylation of a secondary hydroxy group as in (e) in Scheme 20 followed by treatment with DBU produced Compound 81 (98% yield for 2 steps).

Then, deprotection of a primary hydroxy group as in (d) in Scheme 2, followed by oxidation of the primary hydroxy group as in (d) in Scheme 1 produced aldehyde 82 (91% yield for 2 steps).

Subsequently, a side chain was introduced into aromatic ring raw material 112 to yield target product 288-12-Piv as in (e) and (f) in Scheme 1 (36% yield for 2 steps).

[Formula 153]

$^1$H-NMR (400 MHz, CDCl$_3$) δ 13.06 (1H, s, Ar—O$\underline{H}$), 10.15 (1H, s, Ar—C$\underline{H}$O), 6.95 (1H, dt, J=15.0, 7.3 Hz), 6.68 (1H, s, Ar—O$\underline{H}$), 6.64 (1H, dt, J=16.1, 6.8 Hz), 6.52 (1H, d, J=16.1 Hz), 6.50 (1H, d, J=15.0 Hz), 2.62 (3H, s, Ar—C$\underline{H}_3$), 2.19-2.30 (4H, m, allylic C$\underline{H}_2$), 1.60-1.35 (6H, m, —(C$\underline{H}_2$)$_3$—), 1.15 (9H, s, C(C$\underline{H}_3$)$_3$).

3-Chloro-4,6-dihydroxy-5-(11,11-dimethyl-10-oxo-dodecyl)-2-methylbenzaldehyde (Compound 215-12-Piv)

Compound 288-12-Piv was reduced to yield target product 215-12-Piv as in (g) in Scheme 1 (79% yield).

[Formula 154]

$^1$H-NMR (400 MHz, CDCl$_3$) δ 12.65 (1H, s, Ar—O$\underline{H}$), 10.14 (1H, s, Ar—C$\underline{H}$O), 6.40 (1H, br s, Ar—O$\underline{H}$), 2.71-2.57 (6H, m+s (δ 2.60)), 2.49-2.35 (1H, m), 1.61-1.20 (14H, —(C$\underline{H}_2$)$_7$—), 1.13 (9H, s, C(C$\underline{H}_3$)$_3$).

24. Compounds 289-12-OPiv and 290-12-Opiv

Scheme 24

[Formula 155]

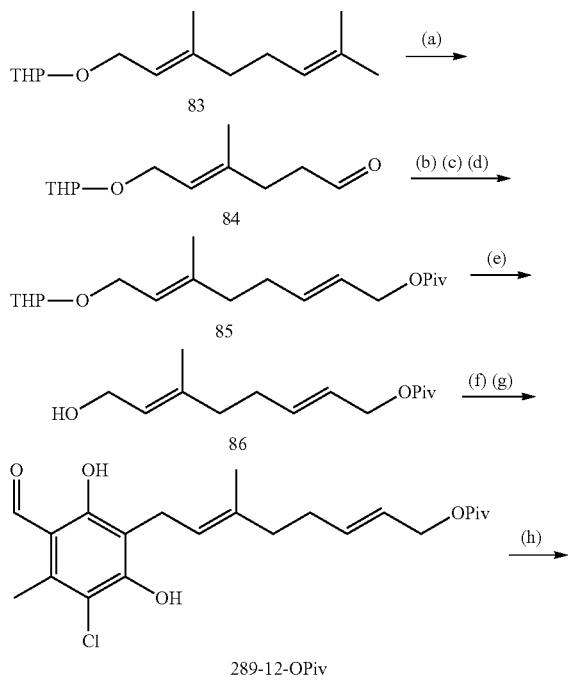

289-12-OPiv

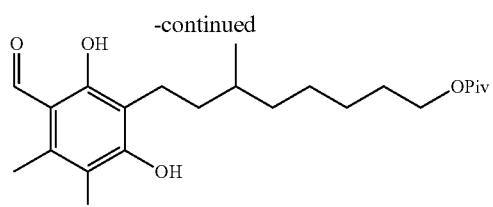

290-12-OPiv (a) O$_3$, Ph$_3$P, CHCl$_3$; (b) (EtO)$_2$P(O)CH$_2$CO$_2$Et, NaH, THF; (c) DIBAL, toluene; (d) Pivaloyl chloride, pyridine, CHCl$_3$; (e) PPTS, EtOH; (f) CBr$_4$, (octyl)$_3$P, Et$_2$O; (g) 112, KOH/CaCl$_2$, MeOH; (h) H$_2$, Pd/C, EtOAc.

(2E,6E)-8-(3-Chloro-5-formyl-2,6-dihydroxy-4-methylphenyl)-6-methyl-2,6-octadienyl pivalate (Compound 289-12-OPiv)

THP ether 83 known in the document (Tetrahedron Lett., 2001, 42, 2205-2208)(5.56 g, 21.2 mmol) was dissolved in CH$_2$Cl$_2$ (115 ml), and pyridine (5.1 ml, 63.6 mmol) was added to the solution, which was cooled to −80° C. Ozone was bubbled through the solution under intensive stirring for 5 hours. The reaction vessel was purged with argon, and Ph$_3$P (16.603 g, 63.6 mmol, 3.0 eq.) was added to the solution. The solution was allowed to warm to room temperature followed by stirring for 12 hours. The residue obtained after the workup was purified by column chromatography on silica gel (hexane:EtOAc=10:1) to yield aldehyde 84 (1.96 g, 44% yield).

Aldehyde 84 was converted to pivalate ester 85 in accordance with methods (b) and (c) (the same as syntheses (c) and (d) in Scheme 18) followed by method (d) (the same as synthesis (c) in Scheme 15) (87% yield for three steps).

Pivalate ester 85 was then deprotected to alcohol 86 in accordance with method (e) (the same as synthesis (d) in Scheme 2) (95% yield). Alcohol 86 was converted to target product 289-12-OPiv in accordance with methods (f) and (g) (the same as syntheses (e) and (f) in Scheme 15) (25% yield for 2 steps).

[Formula 156]

$^1$H-NMR (400 MHz, CDCl$_3$) δ 12.70 (1H, s, Ar—O$\underline{H}$), 10.14 (1H, s, Ar—C$\underline{H}$O), 6.46 (1H, s, Ar—O$\underline{H}$), 5.69 (1H, dt, J=6.0, 15.4 Hz), 5.22 (1H, dt, J=5.8, 15.4 Hz, C$\underline{H}$=C), 5.22 (1H, t, J=7.0 Hz, ArCH$_2$C$\underline{H}$=C), 4.46 (2H, d, J=5.9 Hz, CH$_2$OPiv), 3.39 (2H, d, J=7.3 Hz, Ar—C$\underline{H}_2$), 2.61 (3H, s, Ar—C$\underline{H}_3$), 2.18-2.12 (2H, m, C$\underline{H}_2$), 2.07-2.03 (2H, m, C$\underline{H}_2$), 1.78 (3H, s, C$\underline{H}_3$), 1.56 (3H, s, C$\underline{H}_3$), 1.19 {9H, s, C(C$\underline{H}_3$)$_3$}.

IR (KBr) 3273, 2974, 2932, 1728, 1618, 1479, 1452, 1424, 1281, 1229, 1159, 1107, 963, 905, 783, 714, 592, 538 cm$^{-1}$.

8-(3-Chloro-5-formyl-2,6-dihydroxy-4-methylphenyl)-6-methyloctyl pivalate (Compound 290-12-OPiv)

289-12-OPiv was reduced to target product 290-12-OPiv in accordance with method (h) (the same as synthesis (g) in Scheme 15) (63% yield).

[Formula 157]

$^1$H-NMR (400 MHz, CDCl$_3$) δ 12.65 (1H, s, Ar—O$\underline{H}$), 10.14 (1H, s, Ar—C$\underline{H}$O), 6.38 (1H, s, Ar—O$\underline{H}$), 4.05 (2H, t, J=6.6 Hz, C$\underline{H}_2$OPiv), 2.67-2.63 (2H, m, Ar—C$\underline{H}_2$), 2.61 (3H, s, Ar—C$\underline{H}_3$), 1.64-1.61 (2H, m, C$\underline{H}_2$), 1.55-1.30 (7H, m, C<u>H</u>CH₃ & C<u>H</u>₂C<u>H</u>₂), 1.23-1.17 (2H, m, C<u>H</u>₂), 1.19 {9H, s, C(C<u>H</u>₃)₃}, 0.95 {3H, d, J=6.6 Hz, CH(C<u>H</u>₃)CH₂}.

IR (KBr) 3380, 2932, 2868, 1717, 1630, 1460, 142, 1375, 1327, 1290, 1248, 1163, 1126, 802, 709, 629, 592 cm⁻¹.

HRMS (EI) calcd. for C₂₂H₃₃ClO₅ (m/z) 412.2017. found 412.2041.

25. Compound 231-9-OMe

Scheme 25

[Formula 158]

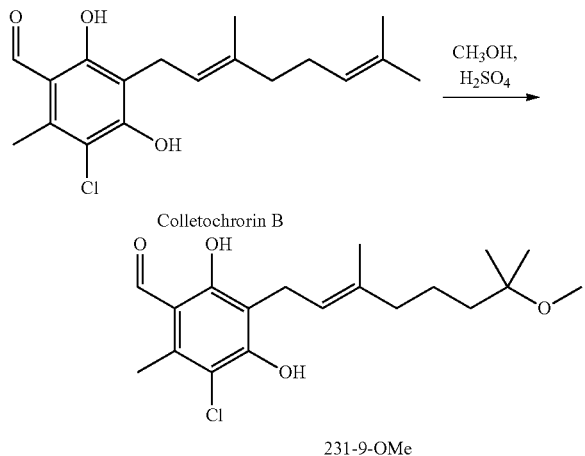

3-Chloro-4,6-dihydroxy-5-[(E)-7-methoxy-3,7-dimethyl-2-octeny]-2-methylbenzaldehyde (Compound 231-9-OMe)

A concentrated sulfuric acid (23 mg, 0.23 mmol) was added to a solution of 216 prepared by Scheme 6 (Colletochlorin B, 74 mg, 0.23 mmol) in methanol (5 ml). The mixture was stirred at 30° C. for 15 hours, and was neutralized with a saturated sodium bicarbonate solution. The product was extracted with ethyl acetate and was posttreated to produce a crude product (109 mg). The crude product was purified by preparative TLC (hexane:EtOAc=3/1) to yield target product 231-9-OMe (39 mg, 48% yield).

[Formula 159]

¹H-NMR (400 MHz, CDCl₃) δ 1.11 (s, 6H, C(OCH₃)(C<u>H</u>₃)₂), 1.34-1.43 (m, 4H, —CH═C(CH₃)C<u>H</u>₂C<u>H</u>₂—), 1.78 (s, 3H, —CH═C(C<u>H</u>₃)—), 1.91-2.00 (m, 2H, —CH═C(CH₃)C<u>H</u>₂—), 2.60 (s, 3H, Ar—C<u>H</u>₃), 3.14 (s, 3H, C(OC<u>H</u>₃)(CH₃)₂), 3.40 (d, J=7.0 Hz, 2H, Ar—C<u>H</u>CH═C(CH₃)—), 5.22 (t, J=7.0 Hz, 1H, ArCH₂C<u>H</u>═C(C<u>H</u>₃)—), 6.39 (br s, 1H, Ar—O<u>H</u>), 10.14 (s, 1H, Ar—C<u>H</u>O), 12.69 (s, 1H, Ar—O<u>H</u>).

26. Compounds 236-13-OTHP, 236-9-OH, 236-12-OTHF, 236-12-OMOM, and 274-9, 281-12

Scheme 26

[Formula 160]

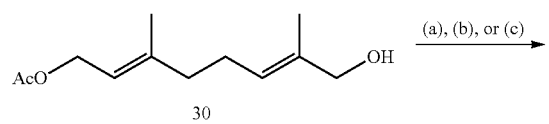

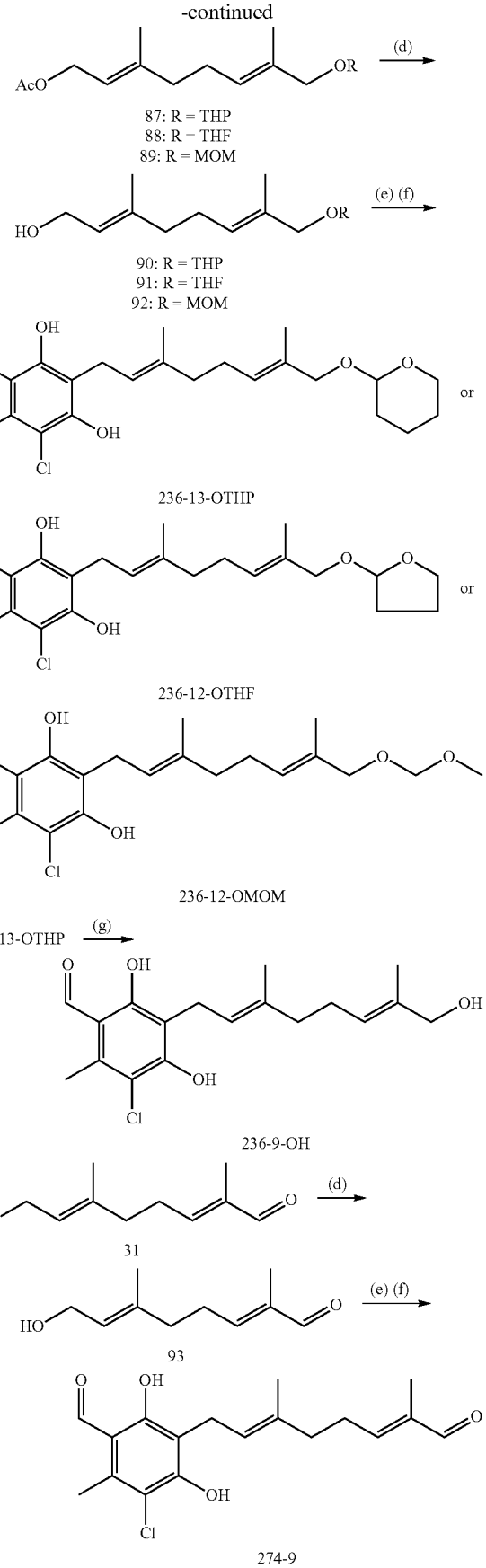

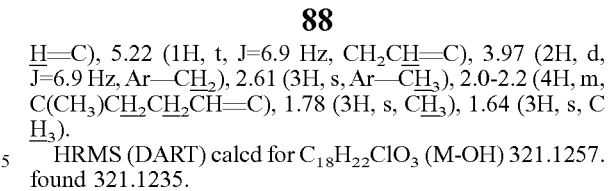

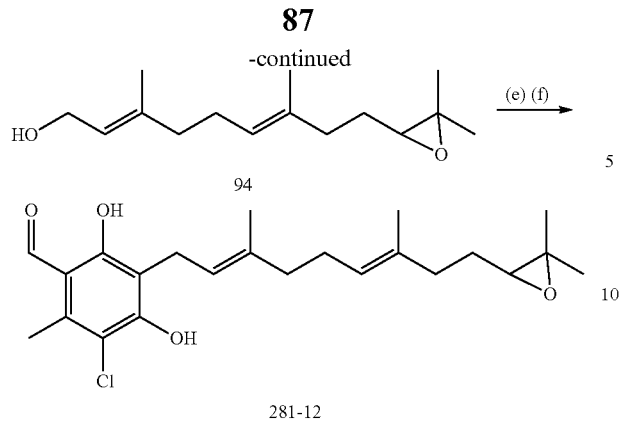

(a) DHP, PPTS, CHCl₃; (b) DHF, PPTS, CHCl₃; (c) MOM-Cl, (i-Pr)₂NEt;
(d) K₂CO₃, MeOH, H₂O; (e) CBr₄, (octyl)₃P, Et₂O; (f) 112, KOH/CaCl₂, MeOH;
(g) PPTS, MeOH

3-Chloro-5-[(2E,6E)-3,7-dimethyl-8-(tetrahydropyran-2-yloxy)-2,6-octadienyl]-4,6-dihydroxy-2-methylbenzaldehyde (Compound 236-13-OTHP)

Alcohol 30 known in the document (J. Braz. Chem. Soc. 2003, 14, 975-981) was converted to Compound 87 by protecting alcohol 30 by the conventional method (a) (the same as (a) in Scheme 2 described above) (96% yield). H₂O (10 ml) and K₂CO₃ (1.24 g, 8.92 mmol) were added to a solution of Compound 87 (1.32 g, 4.46 mmol) in MeOH (8 ml), and the mixture was stirred for 16 hours. After the product was extracted with ether and was posttreated, the resulting crude product was purified by column chromatography (n-hexane/EtOAc=1/1) to yield alcohol 90 (664 mg, 60% yield).

Alcohol 90 was converted to target product 236-13-OTHP in accordance with methods (e) and (f) (the same as syntheses (e) and (f) in Scheme 15) (30% yield for 2 steps).

[Formula 161]
Mp 44-45° C.
$^1$H-NMR (400 MHz, CDCl₃) δ 12.70 (1H, s, Ar—O$\underline{H}$), 10.14 (1H, s, Ar—C$\underline{H}$O), 6.66 (1H, s, Ar—O$\underline{H}$), 5.37 (1H, t, J=6.8 Hz, CH₂C$\underline{H}$=C), 5.22 (1H, t, J=7.1 Hz, CH₂C$\underline{H}$=C), 4.61 (1H, t, J=3.5 Hz, THP(2)-$\underline{H}$), 4.05 (1H, d, J=11.9 Hz, C(C$\underline{H}$₃)CH₂O), 3.83-3.90 (1H, m, THP(6)-H), 3.83 (1H, d, J=11.9 Hz, C(CH₃)C$\underline{H}$₂O), 3.48-3.54 (1H, m, THP(6)-$\underline{H}$), 3.37-3.41 (2H, m, Ar—C$\underline{H}$₂), 2.61 (3H, s, Ar—C$\underline{H}$₃), 2.0-2.2 (4H, m, C(CH₃)C$\underline{H}$₂C$\underline{H}$₂CH=C), 1.6-1.9 (12H, m+s (δ 1.77, C$\underline{H}$₃)+s (δ 1.62, C$\underline{H}$₃), THP(3,4,5)-$\underline{H}$₂).

IR (KBr) 3200-3500, 1613, 1424, 1281, 1250, 1233, 1111 cm⁻¹.

Calcd for C₂₃H₃₁ClO₅: C, 65.32; H, 7.39; Cl, 8.38%. Found: C, 65.18; H, 7.36; Cl, 8.41%.

3-Chloro-4,6-dihydroxy-5-[(2E,6E)-8-hydroxy-3,7-dimethyl-2,6-octadienyl]-2-methylbenzaldehyde (Compound 236-9-OH)

Compound 236-13-OTHP prepared above was de-tetrahydropyranylated to target product 236-9-OH in accordance with the method (g) (the same as (d) in Scheme 2) (90% yield).

[Formula 162]
Mp 99.0-99.7° C.
$^1$H-NMR (400 MHz, CDCl₃) δ 12.72 (1H, s, Ar—O$\underline{H}$), 10.14 (1H, s, Ar—C$\underline{H}$O), 5.34 (1H, t, J=6.6 Hz, CH₂C$\underline{H}$=C), 5.22 (1H, t, J=6.9 Hz, CH₂C$\underline{H}$=C), 3.97 (2H, d, J=6.9 Hz, Ar—C$\underline{H}$₂), 2.61 (3H, s, Ar—C$\underline{H}$₃), 2.0-2.2 (4H, m, C(CH₃)C$\underline{H}$₂C$\underline{H}$₂CH=C), 1.78 (3H, s, C$\underline{H}$₃), 1.64 (3H, s, C$\underline{H}$₃).

HRMS (DART) calcd for C₁₈H₂₂ClO₃ (M-OH) 321.1257. found 321.1235.

3-Chloro-5-[(2E,6E)-3,7-dimethyl-8-(tetrahydrofuran-2-yloxy)-2,6-octadienyl]-4,6-dihydroxy-2-methylbenzaldehyde (Compound 236-12-OTHF)

Alcohol 30 was tetrahydrofuranylated by the conventional method (b) (the same as (a) in Scheme 2 except that dihydropyran (DHP) was replaced by dihydrofuran (DHF)) to yield Compound 88 (97% yield). Subsequently, Compound 88 was similarly converted to alcohol 91 in accordance with the method (d) described above (60% yield). Alcohol 91 was then converted to target product 236-12-OTHF in accordance with methods (e) and (f) (the same as syntheses (e) and (f) in Scheme 15). (13% yield for 2 steps).

[Formula 163]
Mp 35-36° C.
$^1$H-NMR (400 MHz, CDCl₃) δ 12.70 (1H, s, Ar—O$\underline{H}$), 10.14 (1H, s, Ar—C$\underline{H}$O), 6.71 (1H, s, Ar—O$\underline{H}$), 5.36 (1H, t, J=7.0 Hz, CH₂C$\underline{H}$=C), 5.22 (1H, t, J=7.0 Hz, CH₂C$\underline{H}$=C), 5.11 (1H, dd, J=2.6, 4.0 Hz, THF(2)-$\underline{H}$), 3.98 (1H, d, J=11.7 Hz, C(CH₃)C$\underline{H}$₂O), 3.85-3.94 (2H, m, THF(5)-$\underline{H}$₂), 3.81 (1H, d, J=11.7 Hz, C(CH₃)C$\underline{H}$₂O), 3.34-3.44 (2H, m, Ar—C$\underline{H}$₂), 2.61 (3H, s, Ar—C$\underline{H}$₃), 1.8-2.2 (8H, m, C(CH₃)C$\underline{H}$₂C$\underline{H}$₂CH=C and THF(3,4)-$\underline{H}$₂), 1.77 (s, C$\underline{H}$₃), 1.60 (s, C$\underline{H}$₃).

IR (KBr) 3150-3350, 1613, 1422, 1283, 1250, 1234, 1109, 1024 cm⁻¹.

HRMS (DART) calcd for C₂₂H₃₀ClO₅ (MH⁺) 409.1782. found: 409.1758.

3-Chloro-5-[(2E,6E)-3,7-dimethyl-8-(methoxymethoxy)-2,6-octadienyl)-4,6-dihydroxy-2-methylbenzaldehyde (236-12-OMOM)

Alcohol 30 described above was methoxymethylated to Compound 89 in accordance with the conventional method (c) (J. Am. Chem. Soc. 1977, 99, 1275-1276) (71% yield). Subsequently, Compound 89 was converted to alcohol 92 in accordance with the method (d) described above (80% yield). Alcohol 92 was then treated in accordance with the methods (e) and (f) (the same as syntheses (e) and (f) in Scheme 15) to yield target product 236-12-OMOM (12% yield for 2 steps).

[Formula 164]
Mp 49-50° C.
$^1$H-NMR (400 MHz, CDCl₃) δ 12.70 (1H, s, Ar—O$\underline{H}$), 10.14 (1H, s, Ar—C$\underline{H}$O), 6.65 (1H, s, Ar—O$\underline{H}$), 5.37 (1H, t, J=6.4 Hz, CH₂C$\underline{H}$=C), 5.24 (1H, t, J=6.4 Hz, CH₂C$\underline{H}$=C), 4.59 (2H, s, OC$\underline{H}$₂O), 3.89 (2H, s, C(CH₃)C$\underline{H}$₂O), 3.39 (2H, d, J=6.4 Hz, Ar—C$\underline{H}$₂), 3.38 (3H, s, OC$\underline{H}$₃), 2.61 (3H, s, Ar—C$\underline{H}$₃), 2.11-2.17 (2H, m, C(C$\underline{H}$₃)C$\underline{H}$₂CH=C), 2.01-2.06 (2H, m, C(CH₃)C$\underline{H}$₂C$\underline{H}$₂CH=C), 1.77 (s, C$\underline{H}$₃), 1.63 (s, C$\underline{H}$₃).

IR (KBr) 3200-3400, 1631, 1422, 1288, 1254, 1022, 903 cm⁻¹.

Calcd for C₂₀H₂₇ClO₅: C, 62.74; H, 7.11; Cl, 9.26%. Found: C, 62.64; H, 7.09; Cl, 9.22%.

3-Chloro-5-[(2E,6E)-3,7-dimethyl-8-oxo-2,6-octadienyl]-4,6-dihydroxy-2-methylbenzaldehyde (Compound 274-9)

Aldehyde 31 known in the document (Tetrahedron 1974, 30, 715-718) was de-acetylated to compound 93 in accordance with the method (d) described above (90% yield). Compound 93 was treated in accordance with the methods (e) and (f) (the same as syntheses (e) and (f) in Scheme 15) to yield target product 274-9 (27% yield for 2 steps).

[Formula 165]

Mp 111.2-111.4° C.

$^1$H-NMR (400 MHz, CDCl$_3$) δ 12.70 (1H, s, Ar—O$\underline{H}$), 10.15 (1H, s, Ar—C$\underline{H}$O), 9.31 (1H, s, C(CH$_3$)—C$\underline{H}$O), 6.41 (1H, t, J=7.4 Hz, C$\underline{H}_2$CH=C), 6.35 (1H, s, Ar—O$\underline{H}$), 5.26 (1H, t, J=6.8 Hz, CH$_2$C$\underline{H}$=C), 3.40 (2H, d, J=7.4 Hz, Ar—C$\underline{H}_2$), 2.61 (3H, s, Ar—C$\underline{H}_3$), 2.4-2.5 (2H, m, C(CH$_3$)CH$_2$C$\underline{H}_2$CH=C), 2.1-2.2 (2H, m, C(CH$_3$)C$\underline{H}_2$CH$_2$CH=C), 1.81 (3H, s, C$\underline{H}_3$), 1.70 (3H, s, C$\underline{H}_3$).

MS (EI) m/z 338 (5, M+2), 336 (13, M$^+$).

3-Chloro-5-[(2E,6E)-3,7-dimethyl-9-(3,3-dimethyl-oxiran-2-yl)-2,6-nonadienyl]-4,6-dihydroxy-2-methylbenzaldehyde (Compound 281-12)

Alcohol 94 known in the document (Org. Lett. 2006, 8, 5649-5652) was treated in accordance with methods (e) and (f) (the same as syntheses (e) and (f) in Scheme 15) to yield target product 281-12 (4% yield for 2 steps).

[Formula 166]

Mp 36-37° C.

$^1$H-NMR (400 MHz, CDCl$_3$) δ 12.70 (1H, s, Ar—O$\underline{H}$), 10.14 (1H, s, Ar—C$\underline{H}$O), 6.57 (1H, s, Ar—O$\underline{H}$), 5.21 (1H, t, J=7.1 Hz, CH$_2$C$\underline{H}$=C), 5.11 (1H, t, J=6.2 Hz, CH$_2$C$\underline{H}$=C), 3.39 (2H, d, J=7.1 Hz, Ar—C$\underline{H}_2$), 2.69 (1H, t, J=6.2 Hz, oxiran(2)-H), 2.61 (3H, s, Ar—C$\underline{H}_3$), 1.96-2.12 (6H, m, C(CH$_3$)C$\underline{H}_2$C$\underline{H}_2$CH=C(CH$_3$)C$\underline{H}_2$), 1.78 (s, C$\underline{H}_3$), 1.56-1.64 (5H, m+s (δ 1.59), nonadienyl(9)-$\underline{H}_2$ and C$\underline{H}_3$), 1.30 (s, C$\underline{H}_3$), 1.25 (s, C$\underline{H}_3$).

IR (KBr) 3300-3500, 1614, 1418, 1281, 1250, 1233, 1109 cm$^{-1}$.

27. Compound 509-11

Scheme 27

[Formula 167]

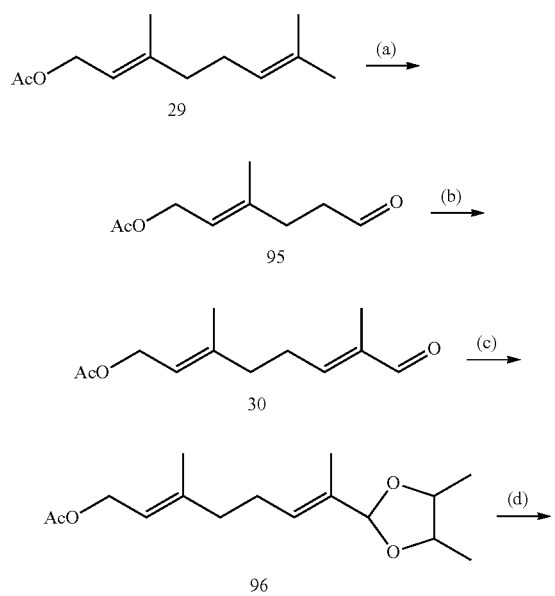

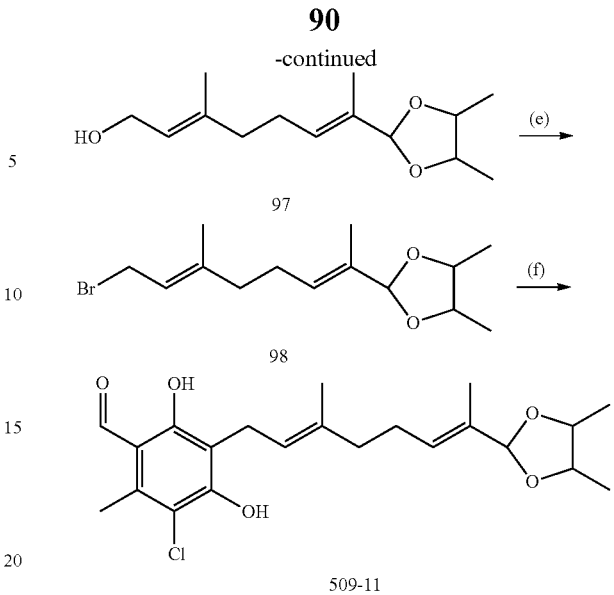

509-11

(a) O$_3$, Ph$_3$P, CH$_2$Cl$_2$; (b) Ph$_2$P=C(CH$_3$)C=O, toluene;
(c) 2,3-dimethylbutane, PPTS; (d) K$_2$CO$_3$, MeOH, H$_2$O; (e) n-BuLi, LiBr, p-TsOH;
(f) 112, KOH/CaCl$_2$, MeOH.

3-Chloro-5-((2E,6E)-7-(4,5-dimethyl-1,3-dioxolane-2-yl)-3-methyl-2,6-octadienyl)-4,6-dihydroxy-2-methylbenzaldehyde (Compound 509-11)

Aldehyde 95 known in the document (J. Am. Chem. Soc. 2005, 127, 7014-7024) which was prepared from a commercially available product 29 in accordance with the method (a) was converted to Compound 30 of which the chain is extended in accordance with the method (b) (Org. Lett. 2007, 9, 1461-1464) (55% yield for 2 steps).

Compound 30 was then acetalized with 2,3-butandiol to yield Compound 96 in accordance with the conventional method (c) (J. Am. Chem. Soc. 2005, 127, 7014-7024, id.). Subsequently, Compound 96 was de-acetylated to yield alcohol 97 in accordance with the method (d) (the same as method (d) in Scheme 26) (56% yield for 2 steps).

Alcohol 97 was converted to bromide 98 in accordance with the method (e) (an application of the method in the document described above: Tetrahedron 1984, 40, 2711-2720) and treated in accordance with the method (f) (the same as synthesis (f) in Scheme 15) to yield target product 509-11 (18% yield for 2 steps).

[Formula 168]

Mp. 91.5-92.3° C.

$^1$H-NMR (400 MHz, CDCl$_3$) δ 12.70 (1H, s, Ar—O$\underline{H}$), 10.14 (1H, s, C$\underline{H}$O), 6.67 (1H, s, Ar—O$\underline{H}$), 5.54 (1H, t, J=7.3 Hz, C$\underline{H}$=C), 5.23 (1H, s, dioxolan(2)-$\underline{H}$), 5.19 (1H, t, J=7.2 Hz, C$\underline{H}$=C), 3.51-3.71 (2H, m, dioxolan(4,5)-$\underline{H}$), 3.33-3.44 (2H, m, Ar—C$\underline{H}_2$), 2.60 (3H, s, Ar—C$\underline{H}_3$), 2.14-2.20 (2H, m, C$\underline{H}_2$), 2.01-2.07 (2H, m, C$\underline{H}_2$), 1.76 (3H, s, C$\underline{H}_3$), 1.61 (3H, s, C$\underline{H}_3$), 1.31-1.33 (3H, m, C$\underline{H}_3$), 1.25-1.27 (3H, m, C$\underline{H}_3$).

IR (KBr) 3100-3400, 1618, 1424, 1279, 1250, 1231, 1109, 1086, 667 cm$^{-1}$.

HRMS (DART) calcd for C$_{22}$H$_{30}$ClO$_5$ (MH$^+$) 409.1782. found 409.1757.

28. Compound 503-12-OPiv

Scheme 28

[Formula 169]

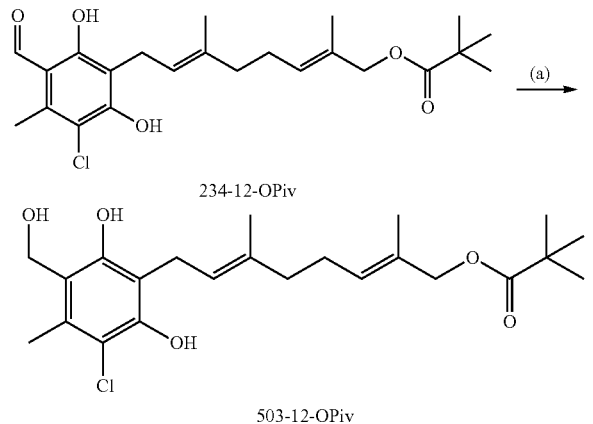

(a) NaBH$_4$, EtOH (2E,6E)-8-(3-Chloro-2,6-dihydroxy-5-hydroxymethyl-4-methylphenyl)-2,6-dimethyl-2,6-octadienyl pivalate (Compound 503-12-OPiv)

Compound 234-12-OPiv prepared by Scheme 15 was treated in accordance with the method (a) (the same as synthesis (b) in Scheme 15) to yield target product 503-12-OPiv (40% yield).

[Formula 170]

$^1$H-NMR (400 MHz, CDCl$_3$) δ 7.54 (1H, s, ArOH), 5.72 (1H, s, ArOH), 5.34 (1H, t, J=7.0 Hz, CH$_2$CH=C), 5.23 (1H, t, J=7.0 Hz, ArCH$_2$CH=C), 4.86 (2H, s, ArCH$_2$OH), 4.32 (2H, s, CH$_2$OPiv), 3.41 (2H, d, J=7.0 Hz, ArCH$_2$), 2.74 (1H, br s, ArCH$_2$OH), 2.31 (3H, s, ArCH$_3$), 2.12-2.18 (2H, m, CH$_2$), 2.03-2.08 (2H, m, CH$_2$), 1.79 (3H, s, CH$_3$), 1.57 (3H, s, CH$_3$), 1.19 (9H, s, C(CH$_3$)$_3$).

IR (KBr) 3300-3500, 1715, 1614, 1456, 1285, 1231, 1159, 1096 cm$^{-1}$.

HRMS (DART) calcd for C$_{23}$H$_{32}$ClO$_5$ (M-H) 423.1938. found 423.1912.

24. Compounds 289-12-OPiv and 290-12-Opiv

Scheme 29

[Formula 171]

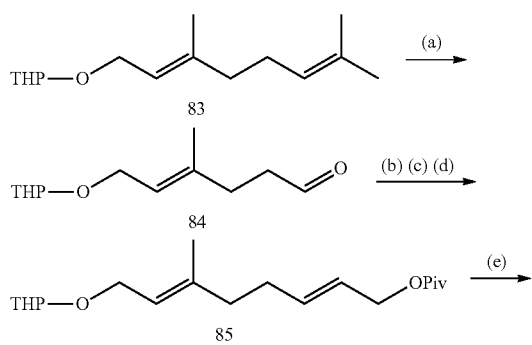

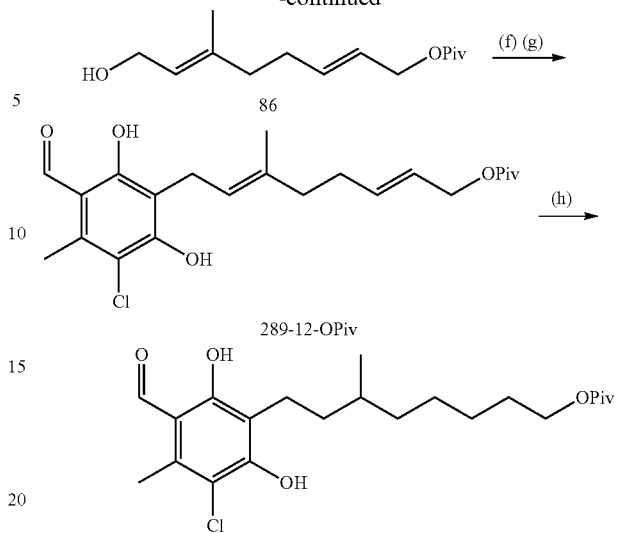

(a) O$_3$, Ph$_3$P, CHCl$_3$; (b) (EtO)$_2$P(O)CH$_2$CO$_2$Et, NaH, THF; (c) DIBAL, toluene; (d) Pivaloyl chloride, pyridine, CHCl$_3$; (e) PPTS, EtOH; (f) CBr$_4$, (octyl)$_3$P, Et$_2$O; (g) 112, KOH/CaCl$_2$, MeOH; (h) H$_2$, Pd/C, EtOAc.

(2E,6E)-8-(3-Chloro-5-formyl-2,6-dihydroxy-4-methylphenyl)-6-methyl-2,6-octadienyl pivalate (Compound 289-12-OPiv)

THP ether 83 known in the document (Tetrahedron Lett., 2001, 42, 2205-2208)(5.56 g, 21.2 mmol) was dissolved in CH$_2$Cl$_2$ (115 ml), and pyridine (5.1 ml, 63.6 mmol) was added to the solution, which was cooled to −80° C. Ozone was bubbled through the solution under intensive stirring for 5 hours. The reaction vessel was purged with argon, and Ph$_3$P (16.603 g, 63.6 mmol, 3.0 eq.) was added to the solution. The solution was allowed to warm to room temperature followed by stirring for 12 hours. The residue obtained after the posttreatment was purified by column chromatography on silica gel (hexane:EtOAc=10:1) to yield aldehyde 84 (1.96 g, 44% yield).

Aldehyde 84 was converted to pivalate ester 85 in accordance with methods (b) and (c) (the same as syntheses (c) and (d) in Scheme 18) followed by method (d) (the same as synthesis (c) in Scheme 15) (87% yield for three steps).

Pivalate ester 85 was deprotected to 86 in accordance with method (e) (the same as synthesis (d) in Scheme 2) (95% yield). Alcohol 86 was converted to target product 289-12-OPiv in accordance with methods (f) and (g) (the same as syntheses (e) and (f) in Scheme 15) (25% yield for 2 steps).

[Formula 172]

$^1$H-NMR (400 MHz, CDCl$_3$) δ 12.70 (1H, s, Ar—OH), 10.14 (1H, s, Ar—CHO), 6.46 (1H, s, Ar—OH), 5.69 (1H, dt, J=6.0, 15.4 Hz, CH=C), 5.22 (1H, dt, J=5.8, 15.4 Hz, CH=C), 5.22 (1H, t, J=7.0 Hz, ArCH$_2$CH=C), 4.46 (2H, d, J=5.9 Hz, CH$_2$OPiv), 3.39 (2H, d, J=7.3 Hz, Ar—CH$_2$), 2.61 (3H, s, Ar—CH$_3$), 2.18-2.12 (2H, m, CH$_2$), 2.07-2.03 (2H, m, CH$_2$), 1.78 (3H, s, CH$_3$), 1.56 (3H, s, CH$_3$), 1.19 {9H, s, C(CH$_3$)$_3$}.

IR (KBr) 3273, 2974, 2932, 1728, 1618, 1479, 1452, 1424, 1281, 1229, 1159, 1107, 963, 905, 783, 714, 592, 538 cm$^{-1}$.

8-(3-Chloro-5-formyl-2,6-dihydroxy-4-methylphenyl)-6-methyloctyl pivalate (Compound 290-12-OPiv)

289-12-OPiv was reduced to target product 290-12-OPiv in accordance with method (h) (the same as synthesis (g) in Scheme 15) (63% yield).

[Formula 173]
$^1$H-NMR (400 MHz, CDCl$_3$) δ 12.65 (1H, s, Ar—O$\underline{H}$), 10.14 (1H, s, Ar—C$\underline{H}$O), 6.38 (1H, s, Ar—O$\underline{H}$), 4.05 (2H, t, J=6.6 Hz, C$\underline{H}_2$OPiv), 2.67-2.63 (2H, m, Ar—C$\underline{H}_2$), 2.61 (3H, s, Ar—C$\underline{H}_3$), 1.64-1.61 (2H, m, C$\underline{H}_2$), 1.55-1.30 (7H, m, C$\underline{H}$CH$_3$ & C$\underline{H}_2$C$\underline{H}_2$), 1.23-1.17 (2H, m, C$\underline{H}_2$), 1.19 {9H, s, C(C$\underline{H}_3$)$_3$}, 0.95 {3H, d, J=6.6 Hz, CH(C$\underline{H}_3$)CH$_2$}.

IR (KBr) 3380, 2932, 2868, 1717, 1630, 1460, 142, 1375, 1327, 1290, 1248, 1163, 1126, 802, 709, 629, 592 cm$^{-1}$.

HRMS (EI) calcd. for C$_{22}$H$_{33}$ClO$_5$ (m/z) 412.2017. found 412.2041.

25. Compound 231-9-Ome

Scheme 30

[Formula 174]

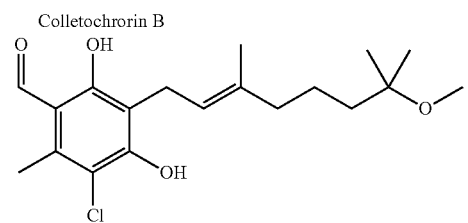

3-Chloro-4,6-dihydroxy-5-[(E)-7-methoxy-3,7-dimethyl-2-octenyl]-2-methylbenzaldehyde (Compound 231-9-OMe)

A concentrated sulfuric acid (23 mg, 0.23 mmol) was added to a solution of Compound 216 prepared by Scheme 6 (Colletochlorin B, 74 mg, 0.23 mmol) in methanol (5 ml). The mixture was stirred at 30° C. for 15 hours, and was neutralized with a saturated sodium bicarbonate solution. The workup through extraction with ethyl acetate produced a crude product (109 mg). The crude product was purified by preparative TLC (hexane:EtOAc=3/1) to yield target product 231-9-OMe (39 mg, 48% yield).

[Formula 175]
$^1$H-NMR (400 MHz, CDCl$_3$) δ 1.11 (s, 6H, C(OCH$_3$)(C$\underline{H}_3$)$_2$), 1.34-1.43 (m, 4H, —CH=C(CH$_3$)CH$_2$C$\underline{H}_2$C$\underline{H}_2$—), 1.78 (s, 3H, —CH=C(C$\underline{H}_3$)—), 1.91-2.00 (m, 2H, —CH=C(CH$_3$)C$\underline{H}_2$—), 2.60 (s, 3H, Ar—C$\underline{H}_3$), 3.14 (s, 3H, C(OC$\underline{H}_3$)(CH$_3$)$_2$), 3.40 (d, J=7.0 Hz, 2H, Ar—C$\underline{H}$CH=C(CH$_3$)—), 5.22 (t, J=7.0 Hz, 1H, ArCH$_2$C$\underline{H}$=C(CH$_3$)—), 6.39 (br s, 1H, Ar—O$\underline{H}$), 10.14 (s, 1H, Ar—C$\underline{H}$O), 12.69 (s, 1H, Ar—O$\underline{H}$).

26. Compounds 236-13-OTHP, 236-9-OH, 236-12-OTHF, 236-12-OMOM, 274-9, and 281-12

Scheme 31

[Formula 176]

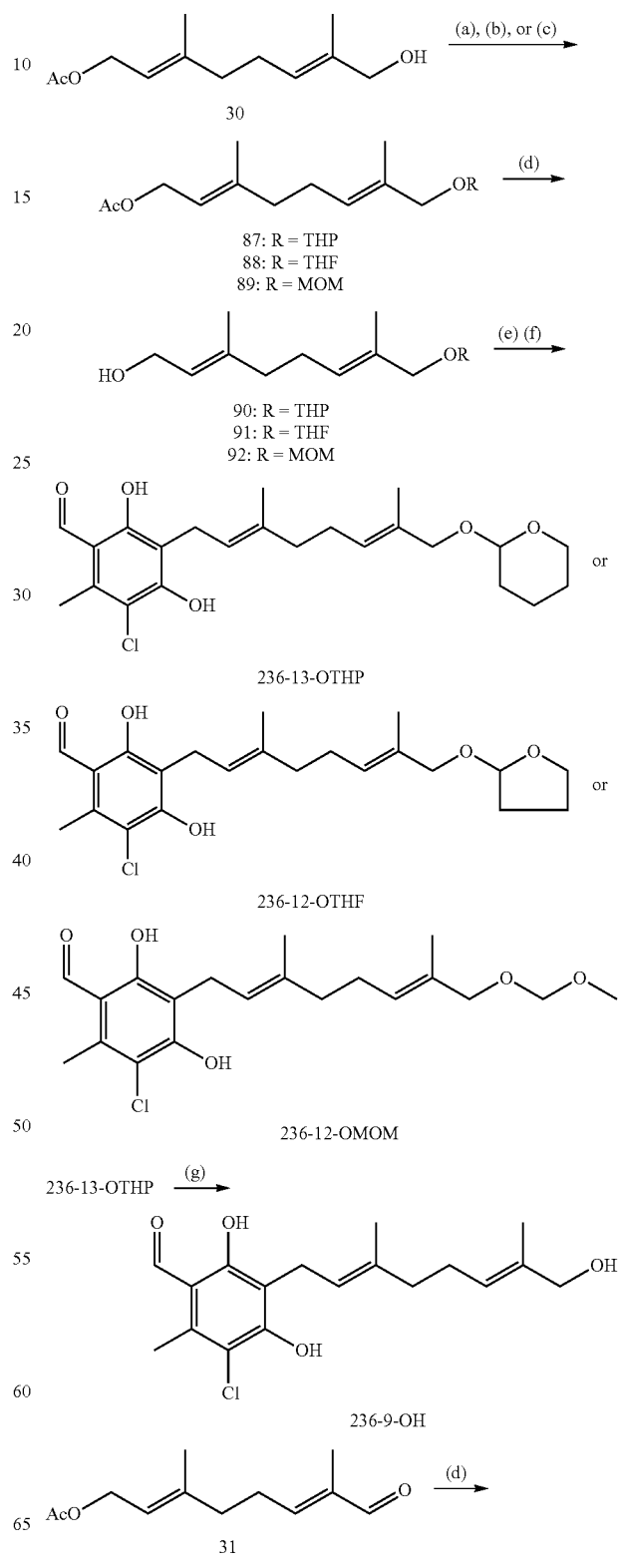

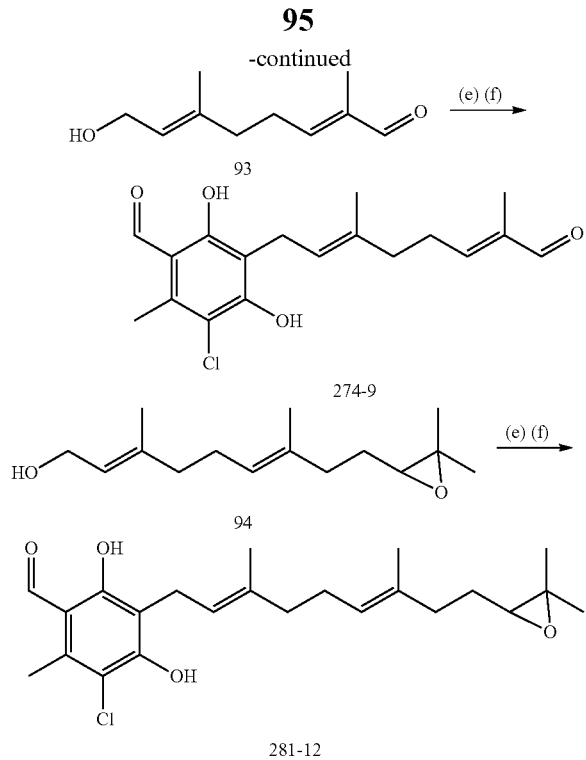

(a) DHP, PPTS, CHCl₃; (b) DHF, PPTS, CHCl₃; (c) MOM-Cl, (i-Pr)₂NEt;
(d) K₂CO₃, MeOH, H₂O; (e) CBr₄, (octyl)₃P, Et₂O; (f) 112, KOH/CaCl₂, MeOH;
(g) PPTS, MeOH

3-Chloro-5-[(2E,6E)-3,7-dimethyl-8-(tetrahydropyran-2-yloxy)-2,6-octadienyl]-4,6-dihydroxy-2-methylbenzaldehyde (Compound 236-13-OTHP)

Alcohol 30 known in the document (J. Braz. Chem. Soc. 2003, 14, 975-981) was converted to Compound 87 by protecting alcohol 30 by the conventional method (a) (the same as (a) in Scheme 2 described above) (96% yield). H₂O (10 ml) and K₂CO₃ (1.24 g, 8.92 mmol) were added to a solution of Compound 87 (1.32 g, 4.46 mmol) in MeOH (8 ml), and the mixture was stirred for 16 hours. After the posttreatment through extraction with ether, the crude product was purified by column chromatography (n-hexane/EtOAc=1/1) to yield alcohol 90 (664 mg, 60% yield).

Alcohol 90 was converted to target product 236-13-OTHP in accordance with methods (e) and (f) (the same as syntheses (e) and (f) in Scheme 15) (30% yield for 2 steps).

[Formula 177]

Mp 44-45° C.

¹H-NMR (400 MHz, CDCl₃) δ 12.70 (1H, s, Ar—OH), 10.14 (1H, s, Ar—CHO), 6.66 (1H, s, Ar—OH), 5.37 (1H, t, J=6.8 Hz, CH₂CH=C), 5.22 (1H, t, J=7.1 Hz, CH₂CH=C), 4.61 (1H, t, J=3.5 Hz, THP(2)-H), 4.05 (1H, d, J=11.9 Hz, C(CH₃)CH₂O), 3.83-3.90 (1H, m, THP(6)-H), 3.83 (1H, d, J=11.9 Hz, C(CH₃)CH₂O), 3.48-3.54 (1H, m, THP(6)-H), 3.37-3.41 (2H, m, Ar—CH₂), 2.61 (3H, s, Ar—CH₃), 2.0-2.2 (4H, m, C(CH₃)CH₂CH₂CH=C), 1.6-1.9 (12H, m+s (δ 1.77, CH₃)+s (δ 1.62, CH₃), THP(3,4,5)-H₂).

IR (KBr) 3200-3500, 1613, 1424, 1281, 1250, 1233, 1111 cm⁻¹.

Calcd for C₂₃H₃₁ClO₅: C, 65.32; H, 7.39; Cl, 8.38%. Found: C, 65.18; H, 7.36; Cl, 8.41%.

3-Chloro-4,6-dihydroxy-5-[(2E,6E)-8-hydroxy-3,7-dimethyl-2,6-octadienyl]-2-methylbenzaldehyde (Compound 236-9-OH)

Compound 236-13-OTHP prepared above was de-tetrahydropyranylated to yield target product 236-9-OH in accordance with the method (g)(the same as (d) in Scheme 2) (90% yield).

[Formula 178]

Mp 99.0-99.7° C.

¹H-NMR (400 MHz, CDCl₃) δ 12.72 (1H, s, Ar—OH), 10.14 (1H, s, Ar—CHO), 5.34 (1H, t, J=6.6 Hz, CH₂CH=C), 5.22 (1H, t, J=6.9 Hz, CH₂CH=C), 3.97 (2H, d, J=6.9 Hz, Ar—CH₂), 2.61 (3H, s, Ar—CH₃), 2.0-2.2 (4H, m, C(CH₃)CH₂CH₂CH=C), 1.78 (3H, s, CH₃), 1.64 (3H, s, CH₃).

HRMS (DART) calcd for C₁₈H₂₂ClO₃ (M-OH) 321.1257. found 321.1235.

3-Chloro-5-[(2E,6E)-3,7-dimethyl-8-(tetrahydrofuran-2-yloxy)-2,6-octadienyl]-4,6-dihydroxy-2-methylbenzaldehyde (Compound 236-12-OTHF)

Alcohol 30 was tetrahydrofuranylated by the conventional method (b) (the same as (a) in Scheme 2 except that dihydropyran (DHP) was replaced by dihydrofuran (DHF)) to yield Compound 88 (97% yield). Subsequently, Compound 88 was similarly converted to alcohol 91 in accordance with the method (d) described above (60% yield). Alcohol 91 was then converted to target product 236-12-OTHF in accordance with methods (e) and (f) (the same as syntheses (e) and (f) in Scheme 15) (13% yield for 2 steps).

[Formula 179]

Mp 35-36° C.

¹H-NMR (400 MHz, CDCl₃) δ 12.70 (1H, s, Ar—OH), 10.14 (1H, s, Ar—CHO), 6.71 (1H, s, Ar—OH), 5.36 (1H, t, J=7.0 Hz, CH₂CH=C), 5.22 (1H, t, J=7.0 Hz, CH₂CH=C), 5.11 (1H, dd, J=2.6, 4.0 Hz, THF(2)-H), 3.98 (1H, d, J=11.7 Hz, C(CH₃)CH₂O), 3.85-3.94 (2H, m, THF(5)-H₂), 3.81 (1H, d, J=11.7 Hz, C(CH₃)CH₂O), 3.34-3.44 (2H, m, Ar—CH₂), 2.61 (3H, s, Ar—CH₃), 1.8-2.2 (8H, m, C(CH₃)CH₂CH₂CH=C and THF(3,4)-H₂), 1.77 (s, CH₃), 1.60 (s, CH₃).

IR (KBr) 3150-3350, 1613, 1422, 1283, 1250, 1234, 1109, 1024 cm⁻¹.

HRMS (DART) calcd for C₂₂H₃₀ClO₅ (MH⁺) 409.1782. found: 409.1758.

3-Chloro-5-[(2E,6E)-3,7-dimethyl-8-(methoxymethoxy)-2,6-octadienyl]-4,6-dihydroxy-2-methylbenzaldehyde (Compound 236-12-OMOM)

Alcohol 30 described above was methoxymethylated to Compound 89 in accordance with the conventional method (c) (J. Am. Chem. Soc. 1977, 99, 1275-1276) (71% yield). Subsequently, Compound 89 was converted to alcohol 92 in accordance with the method (d) described above (80% yield). Alcohol 92 was then treated in accordance with the methods (e) and (f) (the same as syntheses (e) and (f) in Scheme 15) to yield target product 236-12-OMOM (12% yield for 2 steps).

[Formula 180]

Mp 49-50° C.

¹H-NMR (400 MHz, CDCl₃) δ 12.70 (1H, s, Ar—OH), 10.14 (1H, s, Ar—CHO), 6.65 (1H, s, Ar—OH), 5.37 (1H, t, J=6.4 Hz, CH₂CH=C), 5.24 (1H, t, J=6.4 Hz, CH₂CH=C), 4.59 (2H, s, OCH₂O), 3.89 (2H, s, C(CH₃)CH₂O), 3.39 (2H, d, J=6.4 Hz, Ar—C$\underline{H}_2$), 3.38 (3H, s, OC$\underline{H}_3$), 2.61 (3H, s, Ar—C$\underline{H}_3$), 2.11-2.17 (2H, m, C(CH$_3$)C$\underline{H}_2$C$\underline{H}_2$CH=C), 2.01-2.06 (2H, m, C(CH$_3$)C$\underline{H}_2$C$\underline{H}_2$CH=C), 1.77 (s, C$\underline{H}_3$), 1.63 (s, C$\underline{H}_3$).

IR (KBr) 3200-3400, 1631, 1422, 1288, 1254, 1022, 903 cm$^{-1}$.

Calcd for C$_{20}$H$_{27}$ClO$_5$: C, 62.74; H, 7.11; Cl, 9.26%. Found: C, 62.64; H, 7.09; Cl, 9.22%.

3-Chloro-5-[(2E,6E)-3,7-dimethyl-8-oxo-2,6-octadienyl]-4,6-dihydroxy-2-methylbenzaldehyde (Compound 274-9)

Aldehyde 31 known in the document (Tetrahedron 1974, 30, 715-718) was de-acetylated to yield compound 93 in accordance with the method (d) described above (90% yield). Compound 93 was then treated to yield target product 274-9 in accordance with the methods (e) and (f) (the same as syntheses (e) and (f) in Scheme 15) (27% yield for 2 steps).

[Formula 181]
Mp 111.2-111.4° C.
$^1$H-NMR (400 MHz, CDCl$_3$) δ 12.70 (1H, s, Ar—O$\underline{H}$), 10.15 (1H, s, Ar—C$\underline{H}$O), 9.31 (1H, s, C(CH$_3$)—C$\underline{H}$O), 6.41 (1H, t, J=7.4 Hz, CH$_2$C$\underline{H}$=C), 6.35 (1H, s, Ar—O$\underline{H}$), 5.26 (1H, t, J=6.8 Hz, CH$_2$C$\underline{H}$=C), 3.40 (2H, d, J=7.4 Hz, Ar—C$\underline{H}_2$), 2.61 (3H, s, Ar—C$\underline{H}_3$), 2.4-2.5 (2H, m, C(CH$_3$)CH$_2$C$\underline{H}_2$CH=C), 2.1-2.2 (2H, m, C(CH$_3$)C$\underline{H}_2$CH$_2$CH=C), 1.81 (3H, s, C$\underline{H}_3$), 1.70 (3H, s, C$\underline{H}_3$).
MS (EI) m/z 338 (5, M+2), 336 (13, M$^+$).

3-Chloro-5-[(2E,6E)-3,7-dimethyl-9-(3,3-dimethyl-oxiran-2-yl)-2,6-nonadienyl]-4,6-dihydroxy-2-methylbenzaldehyde (Compound 281-12)

Alcohol 94 known in the document (Org. Lett. 2006, 8, 5649-5652) was treated to yield target product 281-12 in accordance with methods (e) and (f) (the same as syntheses (e) and (f) in Scheme 15) (4% yield for 2 steps).

[Formula 182]
Mp 36-37° C.
$^1$H-NMR (400 MHz, CDCl$_3$) δ 12.70 (1H, s, Ar—O$\underline{H}$), 10.14 (1H, s, Ar—C$\underline{H}$O), 6.57 (1H, s, Ar—O$\underline{H}$), 5.21 (1H, t, J=7.1 Hz, CH$_2$C$\underline{H}$=C), 5.11 (1H, t, J=6.2 Hz, CH$_2$C$\underline{H}$=C), 3.39 (2H, d, J=7.1 Hz, Ar—C$\underline{H}_2$), 2.69 (1H, t, J=6.2 Hz, oxiran(2)-$\underline{H}$), 2.61 (3H, s, Ar—C$\underline{H}_3$), 1.96-2.12 (6H, m, C(CH$_3$)C$\underline{H}_2$C$\underline{H}_2$CH=C(CH$_3$)C$\underline{H}_2$), 1.78 (s, CH$_3$), 1.56-1.64 (5H, m+s (δ 1.59), nonadienyl(9)-$\underline{H}_2$ and C$\underline{H}_3$), 1.30 (s, C$\underline{H}_3$), 1.25 (s, C$\underline{H}_3$).

IR (KBr) 3300-3500, 1614, 1418, 1281, 1250, 1233, 1109 cm$^{-1}$.

The pharmacological test will now be described with inventive compounds.

Pharmacological Test Example 1

IC50 Measurement

*Escherichia coli* membrane fractions that express TAO by a plasmid harboring TAO cDNA cloned from *T. brucei brucei* (Fukai, Comparative Biochemistry & Physiology, 124, 141-148, 1999) were used as a recombinant Trypanosome AOX (TAO) enzyme. 50 mM Tris-HCl (pH 7.5), TAO-expressing membrane fraction (0.35 ng), and 1 mL of an inhibitor were mixed in a 1 mL cuvette, and the mixture was incubated at 25° C. for 4 minutes. Ubiquinol-1 as a substrate was then added to the mixture to initiated the reaction, and change in absorbance at 278 nm was monitored (Shimadzu UV-3000, molar absorption coefficient ϵ=15 cm$^{-1}$ mM$^{-1}$). When the quinol oxidase activity is set to 100% in the absence of inhibitor, the concentration at which 50% quinol oxidase activity is inhibited is defined as 50% inhibitory concentration (IC50).

MIC Measurement

T. b. rhodesiense IL1501, the human infectious protozoan that causes acute symptoms, was used as a Trypanosomatid protozoan. The bloodstream forms of protozoan can be cultured in a HMI-9 culture medium (Hirumi, 1989). The protozoan was always cultured at a temperature of 37° C. in the presence of 5% CO$_2$.

In a microtiter plate (96-well, FALCON 3072), HMI-9 culture medium and HMI-9 culture medium plus glycerol added to make a final concentration of 8.33 mM are separately prepared. 89 µL of the preparation are put into only the first well, and a 60 µL aliquot of each the other wells. 1 µL of a solution of AF or a AF derivative dissolved in DMSO was added to the first well, and was then suspended. A 30 µL aliquot of the suspension was then collected, was transferred to the second well, and was suspended. These operations were repeated in this order to prepare a three-fold dilution series of drug. A 40 µL aliquot of a protozoan culture was added to each well to make a final concentration of 5×10$^4$ cells/well (a final concentration of glycerol of 5 mM) followed by 18-hours culturing under conditions of 37° C. and 5% CO$_2$. (For EC50 measurement, a 10 µL aliquot of Alamar Blue was added to each well), culturing was carried out under the same conditions for 6 more hours, surviving protozoans were visually observed with a microscope. The concentration at which no motile surviving protozoan was observed was defined as MIC.

REFERENCE LIST (1) Hirumi H, Hirumi K.
Continuous cultivation of *Trypanosoma brucei* blood stream forms in a medium containing a low concentration of serum protein without feeder cell layers.
J Parasitol. (1989) 75:985-9.
(2) Fukai Y, Nihei C, Kawai K, Yabu Y, Suzuki T, Ohta N, Minagawa N, Nagai K, Kita K. Overproduction of highly active *Trypanosoma* alternative oxidase in *Escherichia coli* heme-deficient mutant. Parasitol Int. (2003) 52:237-41.

The results of the test are shown in Table below.

TABLE 1

| Compound | TAO Enzyme Inhibition (IC50) | Antiprotozoal Effect (MIC:nM) | |
|---|---|---|---|
| | | Glycerol (+) | Glycerol (−) |
| Ascofuranone (control) | 0.13 | 0.0019 | 0.033 |
| 215-15-COOEt | 0.3 | | |
| 215-15-COOiPr | 0.32 | | |
| 215-13-COOH | 4.2 | | |
| 215-13-COOEt | 0.2 | 2 | 24 |
| 200-12-COOMe | 0.5 | 33 | 120 |
| 215-12-COOMe | 0.25 | 5.7 | 38 |
| 215-13-COOiPr | 0.43 | 0.061 | 1.7 |
| 215-11-COOH | 1.5 | 1500 | 4000 |
| 215-13-COOBu | 0.25 | 1.2 | 16 |
| 501-16-G | 0.32 | 1800 | 14000 |
| 502-16-G | 0.3 | 1.2 | 12 |
| 215-11-COOEt | 0.5 | 8.5 | 48 |
| 215-18-Anthra | 0.5 | 3.8 | 6.6 |

TABLE 1-continued

| Compound | TAO Enzyme Inhibition (IC$_{50}$) | Antiprotozoal Effect (MIC:nM) | |
|---|---|---|---|
| | | Glycerol (+) | Glycerol (−) |
| 173 | 0.15 | 800 fM | 1.4 |
| 282-12 | 0.15 | 11 | 19 |
| 200-11-OPiv | 0.53 | 0.8 | 22 |
| 215-11-OPiv | 0.25 | 0.094 | 0.88 |
| 200-12-OPiv | 0.7 | | |
| 215-12-OPiv | 0.32 | 0.49 | 1.9 |
| 200-13-OPiv | 0.32 | | |
| 215-13-OPiv | 0.22 | 0.0081 | 280 |
| 200-12-OCOiPr | 0.75 | | |
| 215-12-OCOiPr | 0.29 | | |
| 215-13-OCOiPr | 0.3 | | |
| 215-12-OCOEt | 0.29 | | |
| 200-13-OCOEt | 0.3 | | |
| 215-13-OCOEt | 0.2 | 7.1 | 125 |
| 172-11-OPiv | 8 | 19 | 540 |
| 193-11-OPiv | 6 | | |
| 215-11-OAc | 0.6 | 7.7 | 68 |
| 214 | 0.3 | | |
| 209 | 0.2 | | |
| 249 | 1 | 18 | 74 |
| 250 | 0.5 | 0.78 | 12 |
| 275-10-COOMe | 0.38 | 1.1 | 8.7 |
| 276-9 | 1.2 | 0.53 | 13 |
| 277-11-OAc | 1.2 | 0.082 | 2.3 |
| 277-9-OH | 0.48 | 0.048 | 74 |
| 286-9-OH | 7.1 | | |
| 273-12 | 0.23 | 1.9 | 3.7 |
| 271-12 | 0.22 | 0.0023 | 0.056 |
| 234-12-OPiv | 0.4 | 0.031 | 0.39 |
| 175-12-OPiv | 0.7 | 1.4 | 10 |
| 264-11-OPiv | 0.22 | | |
| 265-11-OPiv | 0.36 | | |
| 264-8 | 0.06 | 0.002 | 0.18 |
| 265-8 | 0.18 | 0.011 | 0.46 |
| 264-8-z | 0.18 | 0.17 | 0.25 |
| 268-8 | 0.55 | 0.28 | 14.7 |
| 270-8 | 300 | 3700 | 9200 |
| 269-8 | 2.5 | 70 | 500 |
| 206-12-OPiv | 0.27 | 0.006 | 0.024 |
| 278-8 | 0.25 | 7.4 | 14 |
| 279-8 | 0.22 | 7.3 | 12 |
| 278-12-OPiv | 0.26 | | |
| 279-12-OPiv | 0.41 | | |
| 287-12-OPiv | 0.36 | | |
| 287-12-OCOiPr | 0.26 | | |
| 284-8 | 0.3 | 9.6 | 92 |
| 285-8 | 0.3 | | |
| 288-12-Piv | 0.74 | | |
| 215-12-Piv | 0.4 | | |
| 289-12-OPiv | 0.2 | | |
| 290-12-OPiv | 0.3 | | |
| 231-9-OMe | 0.29 | | |
| 236-13-OTHP | 0.2 | | |
| 236-9-OH | 0.3 | | |
| 236-12-OTHF | 0.12 | | |
| 236-12-OMOM | 0.12 | | |
| 274-9 | 0.3 | | |
| 281-12 | 0.21 | | |
| 509-11 | 0.3 | | |
| 503-OPiv | 0.3 | | |

Note:
(1) "fM" means femtomole.

The results evidently demonstrate that the compounds of the present invention have a TAO enzyme inhibition effect comparable to that of ascofuranone, and have excellent antiprotozoal activity.

Pharmacological Test Example 2

Mice were infected with T. b. rhodesiense, a protozoan that causes acute symptoms at 1×10$^3$ cells/mouse, administration of medication in mice was started 24 hours after the infection, and the mice received five doses of each drug at the dosing interval of 6 hours. Mice were all infected and treated intraperitoneally (i.p). Mice that have no Trypanosomatid protozoan in the blood and survive even 60 days or more after the end of treatment were determined to be cured. Survival days represents an average survival time after treatment in mice that died from infection; therefore, survival days for the group of cured mice are not described in Table 2.

The results of the test are shown in Table below.

TABLE 2

| Compound | Glycerol dose | Cured/Infected | Survival days |
|---|---|---|---|
| Control | 0 | 0/5 | 11 |
| AF | 0 | 0/5 | 12 |
| AF | 50 mg/kg | 0/5 | 12 |
| AF | 750 mg/kg | 2/3 | 21 |
| AF | 1.25 g/kg | 5/5 | — |
| 234-12-OPiv | 1.25 g/kg | 5/5 | — |
| 277-9-OH | 1.25 g/kg | 4/4 | — |
| 277-11-OAc | 1.25 g/kg | 4/4 | — |

Note:
(1) "Glycerol dose" means a content of glycerol in a drug to be administered.
(2) "Cured/infected" means "the number of cured mice/the number of infected mice."
(2) "AF" means "ascofuranone."

The results evidently demonstrate that the compounds of the present invention have antiprotozoal activity comparable to that of ascofuranone.

Pharmacological Test Example 3

*Cryptosporidium* has found to have cyanide insensitive oxidase (AOX), and its inhibitory activity was observed using its recombinant protein (cCpAOX) produced in *E. coli*.

The results of the test are shown in Table below.

TABLE 3

| Compound | CpAOX enzyme inhibition (IC$_{50}$:nM) |
|---|---|
| 215-15-COOEt | 1.8 |
| 215-15-COOiPr | 2.5 |
| 215-15-COOMe | 1.5 |
| 215-13-COOiPr | 2.2 |
| 215-11-COOH | 2.1 |
| 215-13-COOBu | 0.92 |
| 502-16-G | 2.3 |
| 215-18-Anthra | 2.6 |

TABLE 4

| Compound | CpAOX enzyme inhibition (IC$_{50}$:nM) |
|---|---|
| 215-11-OPiv | 1.4 |
| 215-12-OPiv | 2.7 |
| 200-13-OPiv | 2.2 |
| 215-12-OCOiPr | 3.7 |
| 215-12-OCOEt | 2.2 |
| 215-13-OCOEt | 2.1 |
| 215-11-OAc | 2.7 |
| 275-10-COOMe | 1.2 |
| 276-9 | 2.1 |
| 277-11-OAc | 1.5 |
| 277-9-OH | 2.5 |
| 273-12 | 2.2 |
| 271-12 | 1.6 |

TABLE 4-continued

| Compound | CpAOX enzyme inhibition (IC$_{50}$:nM) |
|---|---|
| 235-12-OPiv | 2.3 |
| 265-11-OPiv | 2.3 |
| 264-8-z | 1.4 |
| 206-12-OPiv | 2.1 |
| 278-8 | 1.2 |
| 279-8 | 2.1 |
| 284-8 | 1.9 |

The results evidently demonstrate that the compounds of the present invention have excellent CpAOX enzyme inhibition action.

Formulation Example

At least one of the compounds of the invention can be used to produce a pharmaceutical composition containing one or more pharmaceutically acceptable carriers. Such a composition can be administered in any suitable dosage form in accordance with administration route of interest. The administration route may be parenteral or oral. For use in the dosage form of tablet, the following exemplary recipe is employed:

Exemplary Recipe for Tablet

| | |
|---|---|
| Inventive Compound | 50 mg |
| Magnesium Oxide | 30 mg |
| Hydroxypropyl Cellulose | 10 mg |
| Carmellose Calcium | 10 mg |
| Microcrystalline Cellulose | 25 mg |
| Talc | 1 mg |
| Titanium Oxide | 1 mg |
| Polyvinyl Pyrrolidone | 20 mg |
| Magnesium Stearate | 1 mg |

Ascofuranone, magnesium oxide, hydroxypropyl cellulose, carmellose calcium, and microcrystalline cellulose were mixed and sieved. The mixture was wet granulated, dried, and sieved. Granules that had passed a sieve were mixed with magnesium stearate to form tablets.

INDUSTRIAL APPLICABILITY

A dihydroxybenzene derivative represented by Formula (I) has excellent antiprotozoal activity, and therefore provides significantly high clinical utility as a drug for preventing and treating diseases caused by protozoans, such as Trypanosomiasis and cryptosporidiosis. The dihydroxybenzene derivative can be more readily synthesized than ascofuranone, and therefore also have outstanding commercial benefit.

The invention claimed is:

1. A compound represented by Formula (I), an optical isomer thereof, or a pharmaceutically acceptable salt thereof:

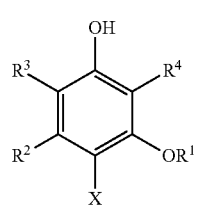

wherein,
X represents a hydrogen atom or a halogen atom;
R$^1$ represents a hydrogen atom;
R$^2$ represents a C$_{1-7}$ alkyl group;
R$^3$ represents —CHO; and
R$^4$ represents a C$_{1-16}$ alkyl group having one or more substituents on a terminal carbon atom and/or non-terminal carbon atom(s), or a C$_{2-16}$ alkenyl group having one or more substituents on a terminal carbon atom and/or non-terminal carbon atom(s),
wherein the one or more substituents of R$^4$ is each any one of —COORa, wherein Ra represents a C$_{1-7}$ alkyl group; —O—CO-Rc, wherein Rc represents a C$_{1-7}$ alkyl group; —O-Rd, wherein Rd represents a C$_{1-7}$ alkyl group; or, —O—CH$_2$—O—CH$_3$, and —O-HET, wherein HET represents a group formed by removing one hydrogen atom on a carbon or nitrogen atom of heterocyclic compounds.

2. A pharmaceutical composition comprising: as an active ingredient, at least one of a compound represented by Formula (I), an optical isomer thereof, or a pharmaceutically acceptable salt thereof, and a pharmaceutically acceptable carrier

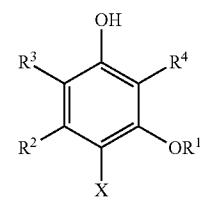

where,
R$^2$ represents a C$_{1-7}$ alkyl group;
R$^3$ represents —CHO; and
R$^4$ represents a C$_{1-16}$ alkyl group having one or more substituents on a terminal carbon atom and/or non-terminal carbon atom(s), or a C$_{2-16}$ alkenyl group having one or more substituents on a terminal carbon atom and/or non-terminal carbon atom(s),
wherein the one or more substituents of R$^4$ is each any one of —COORa, wherein Ra represents a C$_{1-7}$ alkyl group; —O—CO-Rc, wherein Rc represents a C$_{1-7}$ alkyl group; —O-Rd, wherein Rd represents a C$_{1-7}$ alkyl group; or, —O—CH$_2$—O—CH$_3$, and —O-HET, wherein HET represents a group formed by removing one hydrogen atom on a carbon or nitrogen atom of heterocyclic compounds.

3. The pharmaceutical composition of claim 2, further comprising glycerol.

4. A kit comprising: as an active ingredient, at least one of a compound represented by Formula (I), an optical isomer thereof, and a pharmaceutically acceptable salt thereof, and instructions for use

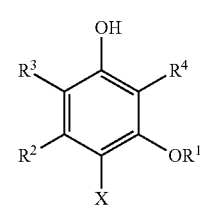

wherein, $R^2$ represents a $C_{1-7}$ alkyl group;

$R^3$ represents —CHO; and $R^4$ represents a $C_{1-16}$ alkyl group having one or more substituents on a terminal carbon atom and/or non-terminal carbon atom(s), or a $C_{2-16}$ alkenyl group having one or more substituents on a terminal carbon atom and/or non-terminal carbon atom(s), wherein the one or more substituents of $R^4$ is each any one of —COORa, wherein Ra represents a $C_{1-7}$ alkyl group; —O—CO-Rc, wherein Rc represents a $C_{1-7}$ alkyl group; —O-Rd, wherein Rd represents a $C_{1-7}$ alkyl group; or, —O—CH$_2$—O—CH$_3$, and —O-HET, wherein HET represents a group formed by removing one hydrogen atom on a carbon or nitrogen atom of heterocyclic compounds.

5. The kit of claim 4, further comprising glycerol.

6. The compound of claim 1, an optical isomer thereof, or a pharmaceutically acceptable salt thereof, wherein the compound represented by Formula (I) is selected from the group consisting of (E)-8-(3-Chloro-5-formyl-2,6-dihydroxy-4-methylphenyl)-6-octenyl pivalate, 9-(3-Chloro-5-formyl-2,6-dihydroxy-4-methylphenyl) nonyl pivalate, (2E,6E)-8-(3-Chloro-5-formyl-2,6-dihydroxy-4-methylphenyl)-2,6-dimethyl-2,6-octadienyl pivalate, 7-(3-Chloro-2,6-dihydroxy-5-formyl-4-methylphenyl)-5-methylheptyl pivalate, (2E,6E)-8-(3-Chloro-5-formyl-2,6-dihydroxy-4-methylphenyl)-2-methyl-2,6-octadienyl pivalate, (2E,6E)-8-(3-Chloro-5-formyl-2,6-dihydroxy-4-methylphenyl)-3,6-dimethyl-2,6-octadienyl isobutylate, and (2E,6E)-8-(3-Chloro-5-formyl-2,6-dihydroxy-4-methylphenyl)-3,6-dimethyl-2,6-octadienyl pivalate.

7. The pharmaceutical composition of claim 2, wherein the compound represented by Formula (I) is selected from the group consisting of (E)-8-(3-Chloro-5-formyl-2,6-dihydroxy-4-methylphenyl)-6-octenyl pivalate, 9-(3-Chloro-5-formyl-2,6-dihydroxy-4-methylphenyl) nonyl pivalate, (2E,6E)-8-(3-Chloro-5-formyl-2,6-dihydroxy-4-methylphenyl)-2,6-dimethyl-2,6-octadienyl pivalate, 7-(3-Chloro-2,6-dihydroxy-5-formyl-4-methylphenyl)-5-methylheptyl pivalate, (2E,6E)-8-(3-Chloro-5-formyl-2,6-dihydroxy-4-methylphenyl)-2-methyl-2,6-octadienyl pivalate, (2E,6E)-8-(3-Chloro-5-formyl-2,6-dihydroxy-4-methylphenyl)-3,6-dimethyl-2,6-octadienyl isobutylate, and (2E,6E)-8-(3-Chloro-5-formyl-2,6-dihydroxy-4-methylphenyl)-3,6-dimethyl-2,6-octadienyl pivalate.

8. A method for treating a disease caused by *Trypanosoma* or *Cryptosporidium* comprising administering to a subject in need thereof an effective amount a composition of the compound of claim 1.

9. The method of claim 8, wherein the composition further comprises glycerol.

\* \* \* \* \*